United States Patent [19]
Shibata et al.

[11] Patent Number: 5,750,696
[45] Date of Patent: May 12, 1998

[54] DIOXACYCLOALKANE COMPOUND HAVING RENIN-INHIBITORY ACTIVITY

[75] Inventors: Saizo Shibata; Yasuki Yamada; Koji Ando; Kiyoshi Fukui, all of Takatsuki; Ikuro Nakamura, Iruma; Itsuo Uchida, Takatsuki, all of Japan

[73] Assignee: Japan Tobacco Inc., Tokyo, Japan

[21] Appl. No.: 387,808

[22] PCT Filed: Aug. 19, 1993

[86] PCT No.: PCT/JP93/01156

§ 371 Date: Feb. 21, 1995

§ 102(e) Date: Feb. 21, 1995

[87] PCT Pub. No.: WO94/04523

PCT Pub. Date: Mar. 3, 1994

[30] Foreign Application Priority Data

Aug. 21, 1992 [JP] Japan ................... 4-244037

[51] Int. Cl.$^6$ ............ C07D 317/28; C07D 233/64; A61K 31/335; C07C 215/26
[52] U.S. Cl. ............ 544/374; 549/448; 548/215; 548/229; 548/232; 548/311.1; 548/314; 514/336; 514/252; 514/397; 560/32; 560/115; 556/420
[58] Field of Search ............ 549/448; 548/314.7, 548/465, 215, 229, 232, 311.1; 546/210, 207; 544/374; 556/420; 560/32, 115; 514/326, 252, 397

[56] References Cited

U.S. PATENT DOCUMENTS

| | | | |
|---|---|---|---|
| 4,680,284 | 7/1987 | Luly | 514/18 |
| 4,761,491 | 8/1988 | Heistand | 549/435 |
| 4,853,383 | 8/1989 | Baldwin | 514/235.8 |
| 4,861,764 | 8/1989 | Samour | 514/177 |
| 4,987,132 | 1/1991 | Mase | 514/252 |
| 5,112,819 | 5/1992 | Ross | 514/212 |
| 5,242,903 | 9/1993 | Bender | 514/18 |
| 5,322,963 | 6/1994 | Shibata | 564/343 |
| 5,484,780 | 1/1996 | Boyd | 514/94 |

OTHER PUBLICATIONS

S. Ishibuchi et al., *Tetrahedron Letters*, 32(29), 3523–3526 (1991).

W. Patt et al., *J. Med. Chem.*, 35(14), 2562–2572 (1992).

*Primary Examiner*—Irina S. Zemel
*Attorney, Agent, or Firm*—Wenderoth, Lind & Ponack

[57] ABSTRACT

Dioxacycloalkane compounds of the formula [1]

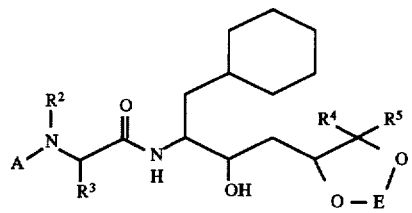

wherein A is

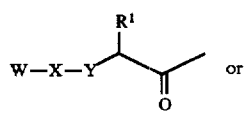

or

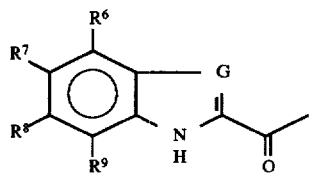

wherein W is

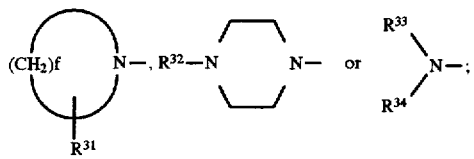

X is —CO— or —SO$_2$—; Y is —CH$_2$—, —O— or —NR$^{25}$—; and R$^1$ is an aralkyl which may be substituted by lower alkoxy;
R$^2$ is a hydrogen atom or a lower alkyl;
R$^3$ is —(CH$_2$)d-SR$^{26}$ or

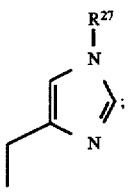

R$^4$ and R$^5$ are each a hydrogen atom or a lower alkyl; and E is —C(R$^{29}$)(R$^{30}$)— or —CH$_2$CH$_2$—, pharmaceutically acceptable salts thereof, intermediates for producing said compounds, and methods for producing said intermediates. The compounds of the formula [1] have a strong inhibitory activity against renin and show continuous hypotensive action by oral administration. They are useful as hypotensive agents or therapeutic agents for heart failure.

17 Claims, No Drawings

DIOXACYCLOALKANE COMPOUND HAVING RENIN-INHIBITORY ACTIVITY

TECHNICAL FIELD

The present invention relates to novel dioxacycloalkane compounds having renin-inhibitory activity, which are usable in the pharmaceutical field as a therapeutic agent for hypertension and the like.

BACKGROUND ART

A renin-angiotensin system is one of the vasopressor systems in the body and an important blood pressure-humoral electrolyte adjusting system. Renin is a protease consisting of 340 amino acids, which specifically cleaves angiotensinogen in plasma. It acts on angiotensinogen in plasma to cleave same into angiotensin I (AI) consisting of 10 amino acid residues. AI is further cleaved by an angiotensin converting enzyme (ACE) into angiotensin II (AII) consisting of 8 amino acid residues. AII has a strong pressor activity and renin is a rate limiting enzyme for this system and important factor for blood pressure control. The physiological activity of AII includes, besides the above-mentioned pressor activity, stimulation of secretion of aldosterone, which is a kind of adrenocortical hormones, and AII promotes storage of $Na^+$ and $Cl^-$, and discharge of $K^+$ and $H^+$ in the body. Accordingly, a renin inhibitor is useful as a therapeutic agent for hypertension due to renin excess and a diagnostic for identification of patients with hypertension caused by renin excess, and various studies have been done in recent years. As to the peptide compounds having renin-inhibitory activity, there are WO90/07521, Japanese Patent Unexamined Publication Nos. 19071/1989, 221357/1989, 204860/1991 and 503802/1992 and many other reports.

It has been also reported that the compounds having renin-inhibitory activity are effective as therapeutic agents for HIV-infected diseases (Japanese Patent Unexamined Publication No. 47196/1991).

However, the conventionally-known peptide derivatives having renin-inhibitory action cannot fully exert their pharmacological effects by oral administration.

DISCLOSURE OF THE INVENTION

An object of the present invention is to provide a novel compound which has superior renin-inhibitory activity and can be administered orally.

The present inventors have conducted intensive studies in an attempt to solve the aforementioned problems and found that the C terminal structure of the formula

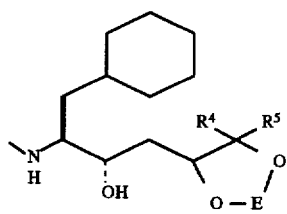

wherein
R⁴ and R⁵ are the same or different and each is a hydrogen atom or a lower alkyl; and
E is —C(R²⁹)(R³⁰)— or —CH₂CH₂— wherein R²⁹ and R³⁰ are the same or different and each is a hydrogen atom, a lower alkyl or a phenyl, or R²⁹ and R³⁰ may combinedly form a ring having 5 to 7 carbon atoms contributes to an extremely improved absorption by oral administration, which in turn results in its high level in blood to continuously exhibit strong hypotensive action, and completed the invention.

Accordingly, the present invention is as follows.

(1) A dioxacycloalkane compound of the formula [1]

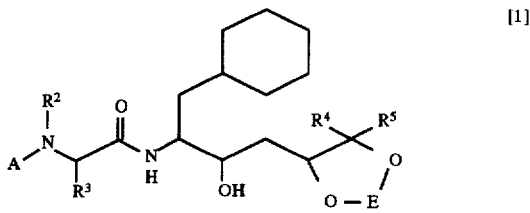

wherein A is

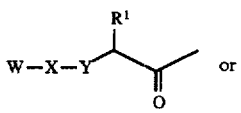

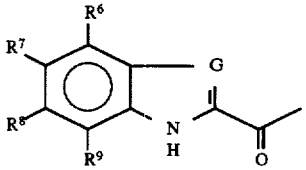

wherein W is

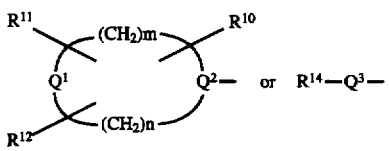

wherein $R^{10}$, $R^{11}$ and $R^{12}$ are the same or different and each is a hydrogen atom, a lower alkyl, a halogen atom, amino, a lower alkylamino, a lower dialkylamino or —O—$R^{15}$ wherein $R^{15}$ is a hydrogen atom, a lower alkyl, a lower alkanoyl or an acyl group of amino acid, m and n are each independently an integer of 0–5, the total of which is 1 to 5, $Q^1$ is

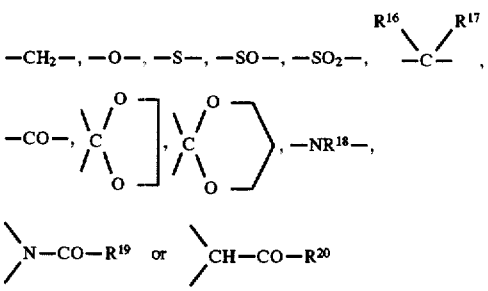

wherein $R^{16}$ and $R^{17}$ are the same or different and each is a lower alkyl or a halogen atom, $R^{18}$ is a hydrogen atom or a lower alkyl, $R^{19}$ and $R^{20}$ are each a lower alkyl or

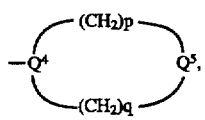

wherein $Q^4$ is —CH< or —N<, and $Q^5$ is —$CH_2$—, —O—, —S—, —SO—, —$SO_2$—, —CO—,

—CHF—, —$CF_2$—, —$NR^{21}$—, >CH—O—$R^{22}$,

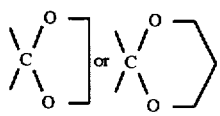

wherein $R^{21}$ and $R^{22}$ are each a hydrogen atom or a lower alkyl, p and q are each independently an integer of 1–4, the total of which does not exceed 5, $Q^2$ is >CH— or >N—, $Q^3$ is —N($R^{13}$)—, —O— or —C($R^{13}$)($R^{23}$)— wherein $R^{13}$ is a hydrogen atom or a lower alkyl, $R^{23}$ is a hydrogen atom or a lower alkyl, and $R^{14}$ is a hydrogen atom, amino, a lower alkylamino, a lower dialkylamino, hydroxy, a lower alkoxy, methoxymethoxy, methoxyethoxymethoxy, a lower alkyl optionally substituted by a group of the formula

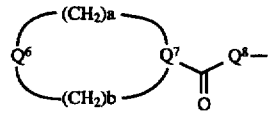

wherein $Q^6$ is the same as the above-mentioned $Q^5$, $Q^7$ is the same as the above-mentioned $Q^4$, $Q^8$ is —$CH^2$— or —$NR^{24}$— wherein $R^{24}$ is a hydrogen atom or a lower alkyl, and a and b are each independently an integer of 1–4, the total of which does not exceed 5, or a benzyl optionally substituted by a lower alkoxy, X is —CO— or —$SO_2$—, Y is —$CH_2$—, —O— or —$NR^{25}$— wherein $R^{25}$ is a hydrogen atom or a lower alkyl, $R^1$ is an aralkyl optionally substituted by a lower alkoxy, $R^6$, $R^7$, $R^8$ and $R^9$ are the same or different and each is a hydrogen atom, a halogen atom, hydroxy or a lower alkoxy, and G is —N= or —CH=;

$R^2$ is a hydrogen atom or a lower alkyl;

$R^3$ is —$(CH_2)_d$—$SR^{26}$ wherein d is an integer of 1–5 and $R^{26}$ is a hydrogen atom or a lower alkyl, a lower alkyl,

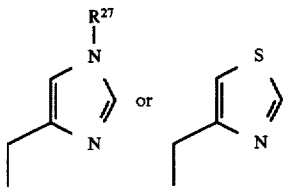

wherein $R^{27}$ is a hydrogen atom, a lower alkyl or —$CH_2O$—CO—$R^{28}$ wherein $R^{28}$ is a lower alkyl or a lower alkoxy;

$R^4$ and $R^5$ are the same or different and each is a hydrogen atom or a lower alkyl; and E is —C($R^{29}$)($R^{30}$) or —$CH_2CH_2$— wherein $R^{29}$ and $R^{30}$ are the same or different and each is a hydrogen atom, a lower alkyl or a phenyl, or $R^{29}$ and $R^{30}$ may combinedly form a ring having 5 to 7 carbon atoms, and a pharmaceutically acceptable salt thereof.

(2) The dioxacycloalkane compound of above (1) of the formula

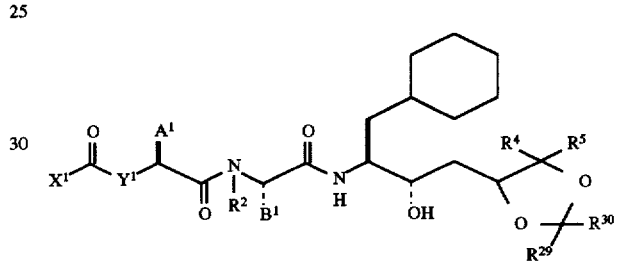

wherein $X^1$ is

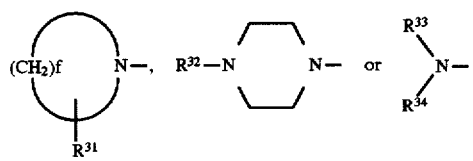

wherein $R^{31}$ is a hydrogen atom or a lower alkyl, $R^{32}$ is a hydrogen atom or a lower alkyl, $R^{33}$ and $R^{34}$ are the same or different and each is a hydrogen atom or a lower alkyl, and f is an integer of 4–6;

$Y^1$ is —$CH_2$—, —O— or —NH—;

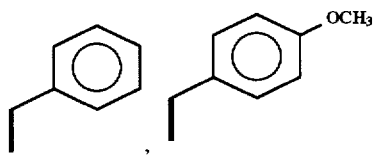

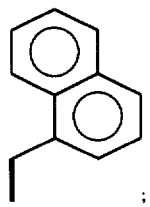

;

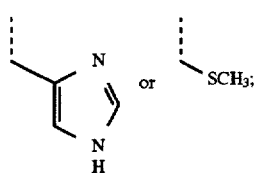

and $R^2$, $R^4$, $R^5$, $R^{29}$ and $R^{30}$ are as defined in the above (1), and a pharmaceutically acceptable salt thereof.

(3) The dioxacycloalkane compound of the above-mentioned (1), which is selected from the group consisting of (1) (4S)-4-[(2S,3S)-4-cyclohexyl-2-hydroxy-3-[[Nα-methyl-Nα-(N-piperidinocarbonyl-L-phenylalanyl)-L-histidyl]amino]-butyl]-5,5-dimethyl-1,3-dioxolane, (2) (4R)-4-[(2S,3S)-4-cyclohexyl-2-hydroxy-3-[[Nα-methyl- Nα-(N-piperidinocarbonyl-L-phenylalanyl)-L-histidyl]amino ]-butyl]-5,5-dimethyl-1,3-dioxolane, (3) (4S)-4-[(2S,3S)-4-cyclohexyl-2-hydroxy-3-[[Nα-[(2S)-3-phenyl-2-piperidinocarbonyloxypropionyl]-L-histidyl] amino ]-butyl]-5,5-dimethyl-1,3-dioxolane, (4) (4S)-4-[(2S,3S)-4-cyclohexyl-2-hydroxy-3-[[Nα-(N-piperidino-carbonyl-L-phenylalanyl)-L-histidyl]amino] butyl]-5,5-dimethyl-1,3-dioxolane, (5) (4S)-4-[(2S,3S)-4-cyclohexyl-2-hydroxy-3-[[S-methyl-N-[(2S)-3-phenyl-2-(4-methylpiperazinyl) carbonyloxypropionyl]-L-cysteinyl [amino[butyl[-5,5-dimethyl-1,3-dioxolane, (6) (4S)-4-[(2S,3S)-4-cyclohexyl-2-hydroxy-3-[[Nα-methyl-Nα-(N-piperidinosulfonyl-L-phenylalanyl)-L-histidyl]amino]-butyl]-5,5-dimethyl-1,3-dioxolane, (7) (4S)-4-[(2S,3S)-4-cyclohexyl-2-hydroxy-3-[[Nα-(indole-2-carbonyl)-L-histidyl]amino]butyl]-5,5-dimethyl-1,3-dioxolane, (8) (4S)-4-[(2S,3S)-4-cyclohexyl-2-hydroxy-3-[[Nα-methyl-Nα-(N-cyclohexylcarbonyl-L-phenylalanyl)-L-histidyl]amino]-butyl]-5,5-dimethyl-1,3-dioxolane, (9) (4S)-4-[(2S,3S)-4-cyclohexyl-2-hydroxy-3-[[Nα-methyl-Nα-[N-(4-methylpiperidino)carbonyl-L-phenylalanyl]-L-histidyl]-amino ]butyl]-5,5-dimethyl-1,3-dioxolane,

(10) (4S)-4-[(2S,3S)-4-cyclohexyl-2-hydroxy-3-[[Nα-methyl-Nα-[N-(diethylamino)carbonyl-L-phenylalanyl]-L-histidyl]amino]-butyl]-5,5-dimethyl-1,3-dioxolane,

(11) (4S)-4-[(2S,3S)-4-cyclohexyl-2-hydroxy-3-[[Nα-methyl-Nα-(N-piperidinocarbonyl-L-phenylalanyl)-L-histidyl]amino]-butyl]-2,2,5,5-tetramethyl-1,3-dioxolane, and

(12) (4S)-4-[(2S,3S)-4-cyclohexyl-2-hydroxy-3-[[Nα-methyl-Nα-(N-piperidinocarbonyl-L-phenylalanyl)-L-histidyl]amino]-butyl]-5,5-dimethyl-2-phenyl-1,3-dioxolane, and a pharmaceutically acceptable salt thereof.

(4) A composition for inhibiting renin, comprising a pharmaceutically suitable carrier and the dioxacycloalkane compound of the above (1) or a pharmaceutically acceptable salt thereof in an amount effective for inhibiting renin.

(5) A composition for inhibiting renin, comprising a pharmaceutically suitable carrier and the dioxacycloalkane compound of the above (2) or a pharmaceutically acceptable salt thereof in an amount effective for inhibiting renin.

(6) A composition for inhibiting renin, comprising a pharmaceutically suitable carrier and the dioxacycloalkane compound of the above (3) or a pharmaceutically acceptable salt thereof in an amount effective for inhibiting renin.

(7) A compound of the formula

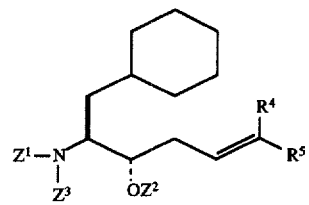

[II]

wherein $Z^1$ is a hydrogen atom or an N-protecting group, $Z^2$ is a hydrogen atom or a hydroxyl-protecting group, $Z^3$ is a hydrogen atom or may form, together with $Z^2$, an optionally substituted oxazolidine ring or an oxazolidinone ring, and $R^4$ and $R^5$ are the same or different and each is a hydrogen atom or a lower alkyl.

(8) A method for stereoselectively producing the compound of the above (7), which is represented by the formula

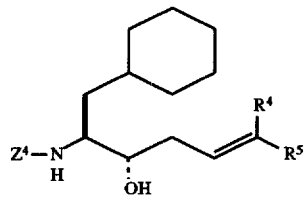

wherein $Z^4$ is an N-protecting group and $R^4$ and $R^5$ are the same or different and each is a hydrogen atom or a lower alkyl, comprising reacting an aldehyde of the formula

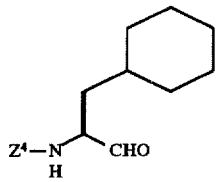

wherein $Z^4$ is as defined above, with an allylsilane compound of the formula

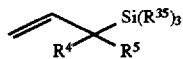

wherein $R^{35}$ is a lower alkyl and $R^4$ and $R^5$ are as defined above, in the presence of a Lewis acid.

(9) A compound of the formula

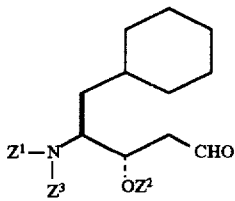

[III]

wherein $Z^1$, $Z^2$ and $Z^3$ are as defined in the above (7).

(10) A compound of the formula

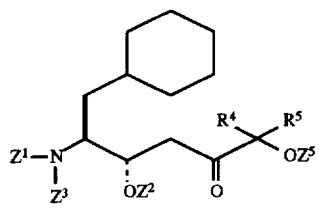

[IV]

wherein $Z^1$, $Z^2$, $Z^3$, $R^4$ and $R^5$ are as defined in the above (7), and $Z^5$ is a hydrogen atom or a hydroxyl-protecting group.

(11) A method for stereoselectively producing the compound of the above (10), which is represented by the formula

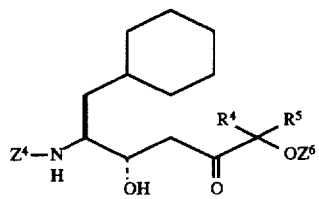

wherein $R^4$ and $R^5$ are the same or different and each is a hydrogen atom or a lower alkyl, $Z^4$ is an N-protecting group and $Z^6$ is a hydroxyl-protecting group, comprising reacting an aldehyde of the formula

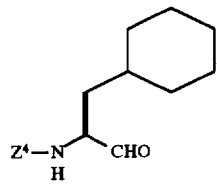

wherein $Z^4$ is as defined above, with a silylenol ether compound of the formula

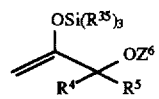

wherein $R^{35}$ is a lower alkyl, and $R^4$, $R^5$ and $Z^6$ are as defined above, in the presence of a Lewis acid.

(12) A compound of the formula

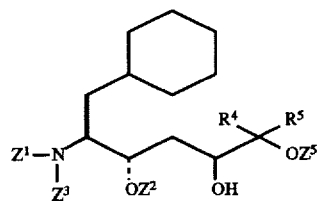

[V]

wherein $Z^1$, $Z^2$, $Z^3$, $R^4$ and $R^5$ are as defined in the above (7), and $Z^5$ is a hydrogen atom or a hydroxyl-protecting group.

(13) A compound of the formula

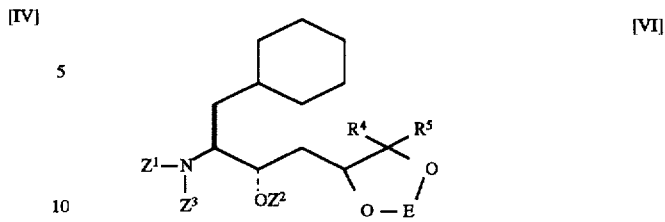

[VI]

wherein $Z^1$, $Z^2$, $Z^3$, $R^4$ and $R^5$ are as defined in above (7), E is —C($R^{29}$)($R^{30}$)— or —CH$_2$CH$_2$— wherein $R^{29}$ and $R^{30}$ are the same or different and each is a hydrogen atom, a lower alkyl or a phenyl, or $R^{29}$ and $R^{30}$ may combinedly form a ring having 5 to 7 carbon atoms.

(14) A method for stereoselectively producing a compound of the formula

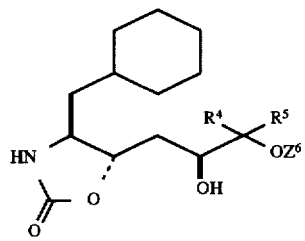

wherein $R^4$ and $R^5$ are the same or different and each is a hydrogen atom or a lower alkyl, and $Z^6$ is a hydroxyl-protecting group, comprising reducing a compound of the formula

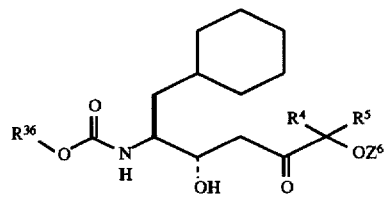

wherein $R^4$, $R^5$ and $Z^6$ are as defined above, and $R^{36}$ is a lower alkyl or a benzyl, using a boron hydride compound in the presence of a lower alkylcarboxylic acid to give a compound of the formula

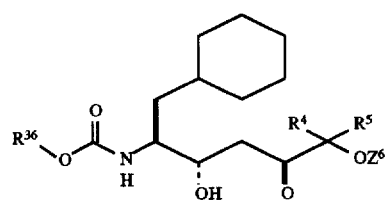

wherein $R^4$, $R^5$, $R^{36}$ and $Z^6$ are as defined above, followed by cyclocondensation in the presence of a base.

(15) A method for producing a compound of the formula

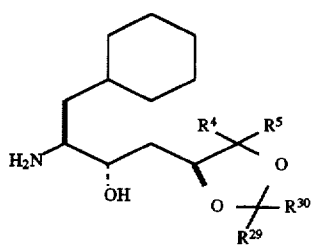

wherein $R^4$ and $R^5$ are the same or different and each is a hydrogen atom or a lower alkyl, and $R^{29}$ and $R^{30}$ are the same or different and each is a hydrogen atom, a lower alkyl or a phenyl, or $R^{29}$ and $R^{30}$ may combinedly form a ring having 5 to 7 carbon atoms, comprising acetalization of a compound of the formula

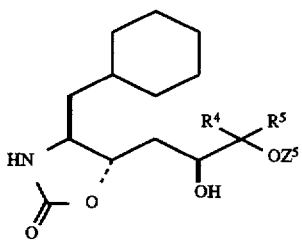

wherein $R^4$ and $R^5$ are as defined above, and $Z^5$ is a hydrogen atom or a hydroxyl-protecting group, using an acid including a Lewis acid as a catalyst to give a compound of the formula

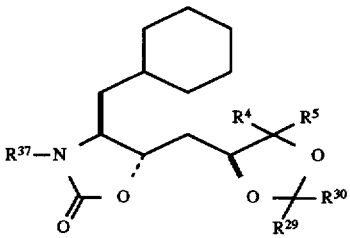

wherein $R^4$, $R^5$, $R^{29}$ and $R^{30}$ are as defined above, and $R^{37}$ is a hydrogen atom or methoxymethyl, followed by hydrolysis under the basic conditions.

(16) A method for producing a compound of the formula

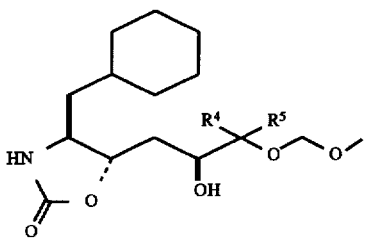

wherein $R^4$ and $R^5$ are the same or different and each is a hydrogen atom or a lower alkyl, comprising reacting an aldehyde of the formula

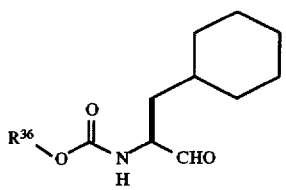

wherein $R^{36}$ is a lower alkyl or a benzyl, with a silylenol ether, compound of the formula

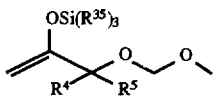

wherein $R^4$ and $R^5$ are as defined above, and $R^{35}$ is a lower alkyl, in the presence of a Lewis acid to stereoselectively produce a compound of the formula

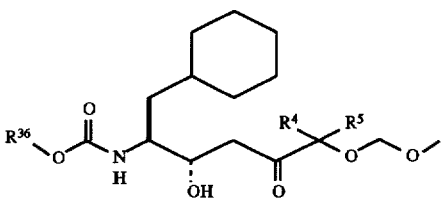

wherein $R^4$, $R^5$ and $R^{36}$ are as defined above, and reducing the obtained compound using a boron hydride compound in the presence of a lower alkylcarboxylic acid to stereoselectively produce a compound of the formula

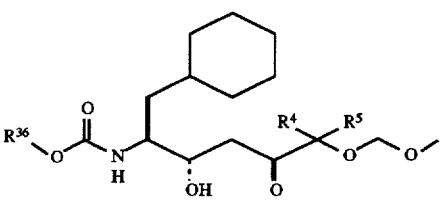

wherein $R^4$, $R^5$ and $R^{36}$ are as defined above, followed by cyclocondensation in the presence of a base.

(17) A method for producing a compound of the formula

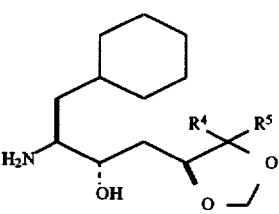

wherein $R^4$ and $R^5$ are the same or different and each is a hydrogen atom or a lower alkyl, comprising cyclocondensation of a compound of the formula

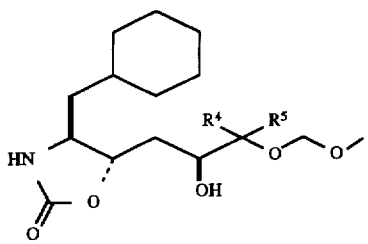

wherein $R^4$ and $R^5$ are as defined above, in the presence of an acid or diphosphorus pentaoxide, or reacting the compound with dimethoxymethane using an acid as a catalyst to give a compound of the formula

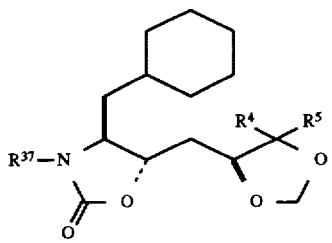

wherein $R^4$ and $R^5$ are as defined above, and $R^{37}$ is a hydrogen atom or methoxymethyl, followed by hydrolysis under the basic conditions.

(18) A compound of the formula

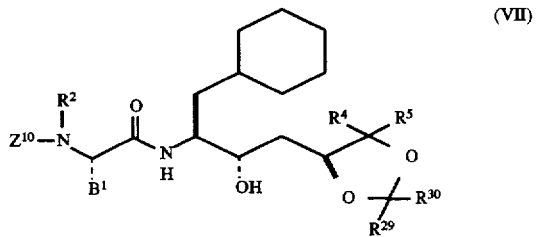

(VII)

wherein $Z^{10}$ is a hydrogen atom or an N-protecting group, and $R^2$, $R^4$, $R^5$, $R^{29}$, $R^{30}$ and $B^1$ are as defined in the above (2).

In the present Specification, the terms used for various definitions mean the following.

Lower alkyl means a straight or branched alkyl having 1 to 7 carbon atoms, such as methyl, ethyl, n-propyl, isopropyl, n-butyl, isobutyl, sec-butyl, tert-butyl, n-pentyl, 1-methylbutyl, 2,2-dimethylpropyl, 2,2-dimethylbutyl, 2-methylpentyl, n-hexyl and 2-methylhexyl. Preferred are those having 1 to 5 carbon atoms, particularly those having 1 to 4 carbon atoms, such as methyl, ethyl, propyl, isopropyl and tert-butyl.

Halogen atom means fluorine, chlorine, bromine or iodine.

Lower alkoxy means a straight or branched alkoxy having 1 to 7 carbon atoms, such as methoxy, ethoxy, propoxy, isopropoxy, n-butoxy, isobutoxy, sec-butoxy and tert-butoxy. Preferred are those having 1 to 5 carbon atoms, particularly those having 1 to 4 carbon atoms, such as methoxy and ethoxy.

Lower alkylamino means that wherein an amino group is substituted by the above-mentioned lower alkyl, and is exemplified by methylamino, ethylamino, n-propylamino, isopropylamino, n-butylamino, isobutylamino and tert-butylamino.

Lower dialkylamino means an amino group disubstituted by the above-mentioned lower alkyl, and is exemplified by dimethylamino, diethylamino, di-n-propylamino, diisopropylamino, di-n-butylamino, ethylmethylamino, propylmethylamino, 1-methylethylmethylamino and butylmethylamino.

Lower alkanoyl is a straight or branched alkanoyl having 2 to 8 carbon atoms, such as acetyl, propionyl, butyryl, isobutyryl, valeryl, isovaleryl, pivaloyl, hexanoyl, heptanoyl and octanoyl.

Acyl group of amino acid is a substituent ($H_2N$—CHR—CO—) having a structure wherein the hydroxyl moiety of the carboxyl group of an amino acid such as $H_2N$—CHR—COOH is eliminated, which may be a natural or synthetic amino acid. Specific examples include D-, L- or DL-glycyl, alanyl, valyl, leucyl, isoleucyl, α-aspartyl, β-aspartyl, asparaginyl, α-glutamyl, β-glutamyl, glutaminyl, lysyl, arginyl, histidyl, seryl, threonyl, phenylalanyl, tyrosyl, tryptophyl, cysteinyl, methionyl, prolyl, β-alanyl, homoseryl, sarcosyl, ornithyl, N,N-dimethylglycyl and N,N-dimethylalanyl, with particular preference given to L-valyl, L-leucyl, L-methionyl, L-lysyl, L-glutamyl and L-prolyl.

Aralkyl is a lower alkyl substituted by an aryl such as phenyl, 1-naphthyl or 2-naphthyl, and preferred is phenyl lower alkyl and naphthyl lower alkyl.

N-protecting group is a protecting group conventionally used in the field of amino acid chemistry, and may be any as long as it protects amino group and imino group from various reactions. Examples thereof include substituted or non-substituted lower alkanoyl such as formyl, acetyl, propionyl and trifluoroacetyl, phthaloyl, lower alkoxycarbonyl such as ethoxycarbonyl, tert-butoxycarbonyl (Boc) and tert-amyloxy-carbonyl, substituted or non-substituted aralkyloxycarbonyl such as benzyloxycarbonyl (Cbz) and p-nitrobenzyloxycarbonyl, substituted or non-substituted arylsulfonyl such as benzene-sulfonyl and tosyl, aralkyl such as trityl and benzyl, and methoxymethyl, with particular preference given to ethoxy-carbonyl, tert-butoxycarbonyl, benzyloxycarbonyl and methoxy-methyl.

Carboxyl-protecting group includes, for example, methyl, ethyl, tert-butyl, benzyl, phenacyl, trichloroethyl, p-nitrobenzyl and diphenylmethyl, which form an ester with carboxyl. The carboxyl-protecting group may be any as long as it is a protecting group conventionally used in the field of amino acid chemistry, and is not limited to these exemplified above. Preferred are methyl, ethyl, tert-butyl and benzyl.

Elimination of N-protecting group means a reaction for eliminating a protecting group from a protected amino or imino to reproduce amino or imino.

Elimination of carboxyl-protecting group means a reaction for eliminating a protecting group from a protected carboxyl to reproduce carboxyl.

The pharmaceutically acceptable salt of the object compound [1] is a conventional, non-toxic salt, which is exemplified by salts with organic acid such as formate, acetate, trifluoroacetate, citrate, maleate, tartrate, methanesulfonate, benzenesulfonate and toluenesulfonate; salts with inorganic acid such as hydrochloride, hydrobromide, sulfate and phosphate; alkali metal salts such as sodium salt and potassium salt; alkaline earth metal salts such as calcium salt and magnesium salt; ammonium salt; salts with organic base such as trimethylamine salt, triethylamine salt, pyridine salt, picoline salt, dicyclohexylamine salt, N,N'-dibenzylethylene-diamine salt; and salts with amino acid such as aspartic acid salt, glutamic acid salt and lysine salt, which are not limitative. Particularly preferred are hydrochloride, citrate, maleate, tartrate and methanesulfonate.

Hydroxyl-protecting group is, for example, that which forms an ether with a hydroxyl group, such as methoxymethyl, methoxyethoxymethyl, benzyloxymethyl, tetrahydropyranyl, benzyl, trimethylsilyl and tert-butyldimethylsilyl, that which forms an ester, such as acetyl, pivaloyl and benzoyl, that which forms cyclic acetal or oxazolidine ring, such as isopropylidene, cyclohexylidene and benzilidene, or cyclic carbonate. Any can be used as long as it is conventionally used, and the hydroxyl-protecting group is not limited to these. Preferred are methoxymethyl, benzyloxymethyl, benzyl, trimethylsilyl and isopropylidene.

Optionally substituted oxazolidine ring has the formula

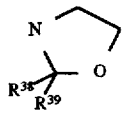

wherein $R^{38}$ and $R^{39}$ are the same or different and each is a hydrogen atom, a lower alkyl or phenyl, or $R^{38}$ and $R^{39}$ may combinedly form a ring having 5 to 7 carbon atoms.

Oxazolidinone ring is expressed by

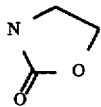

Specific examples of W in the formulas are as follows.

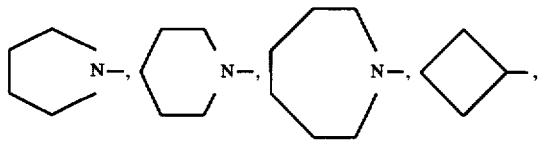

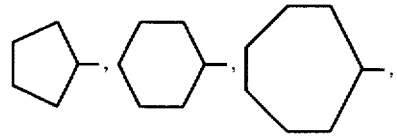

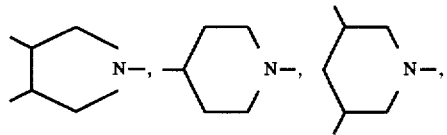

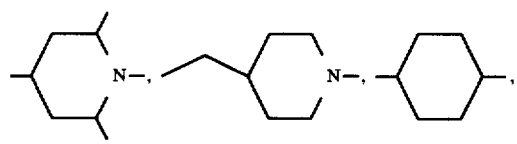

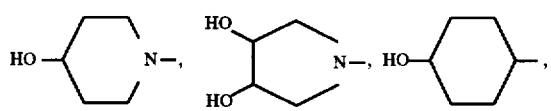

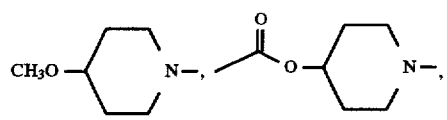

-continued

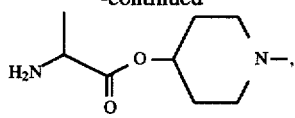

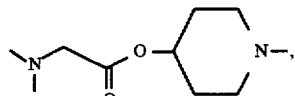

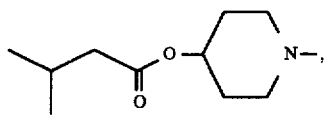

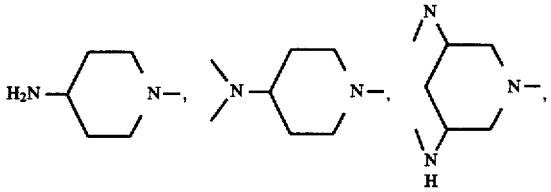

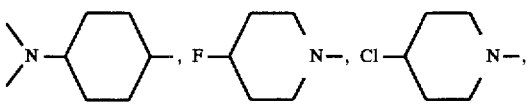

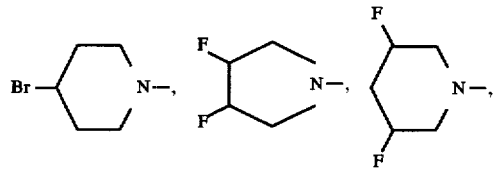

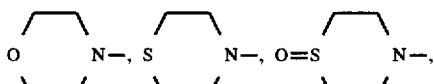

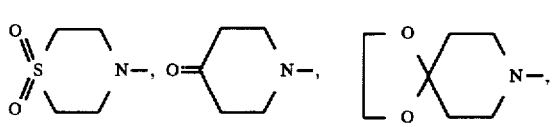

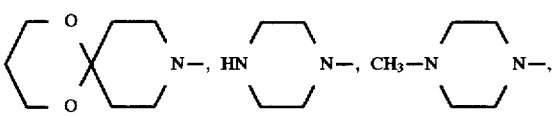

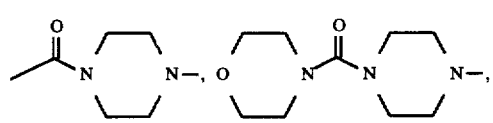

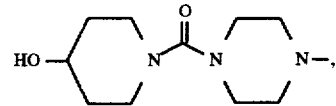

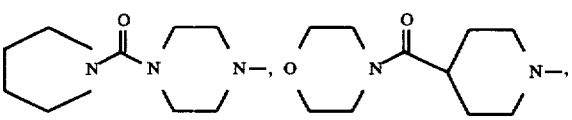

15

-continued

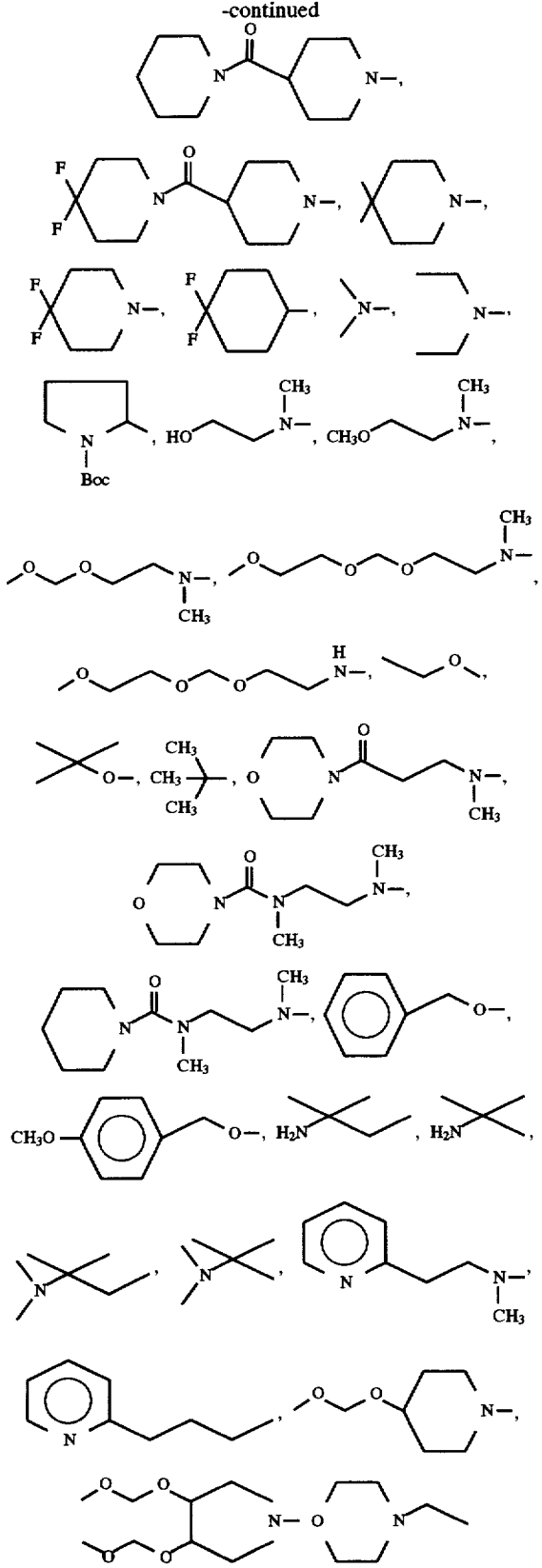

The methods for producing these novel dioxacycloalkane compounds are described in the following.

16

The object compounds [1], salts thereof and intermediates for the production of the object compounds [1] can be produced by the methods to be described in the following. However, the methods for the production of the object compounds [1] and intermediates are not limited to those to be described in the following.

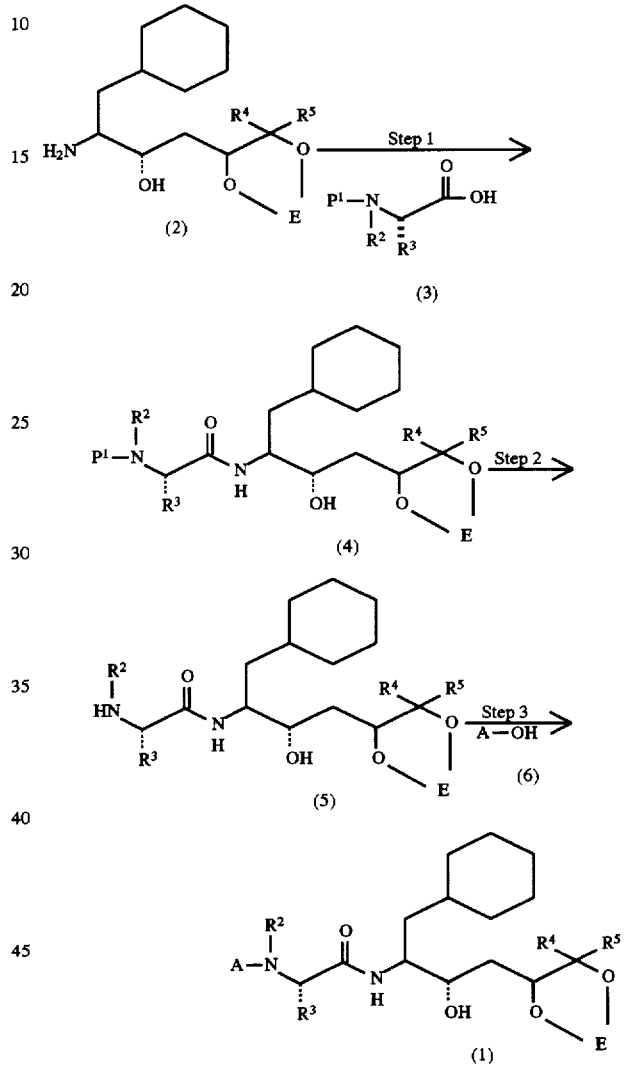

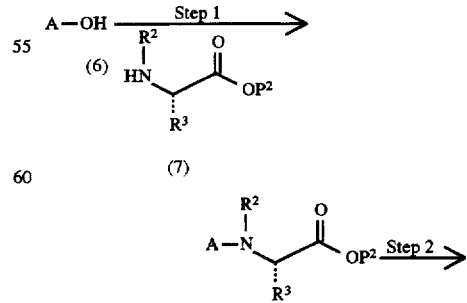

17
-continued
Production Method 2
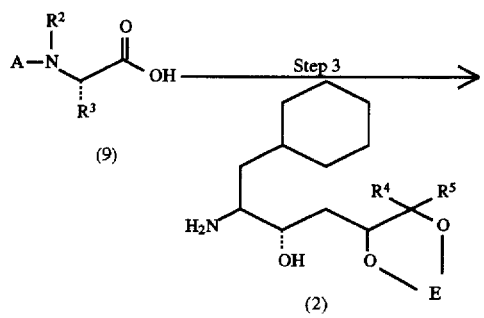
18
-continued
Production Method 2
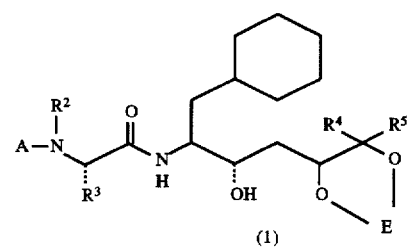
Production Method A
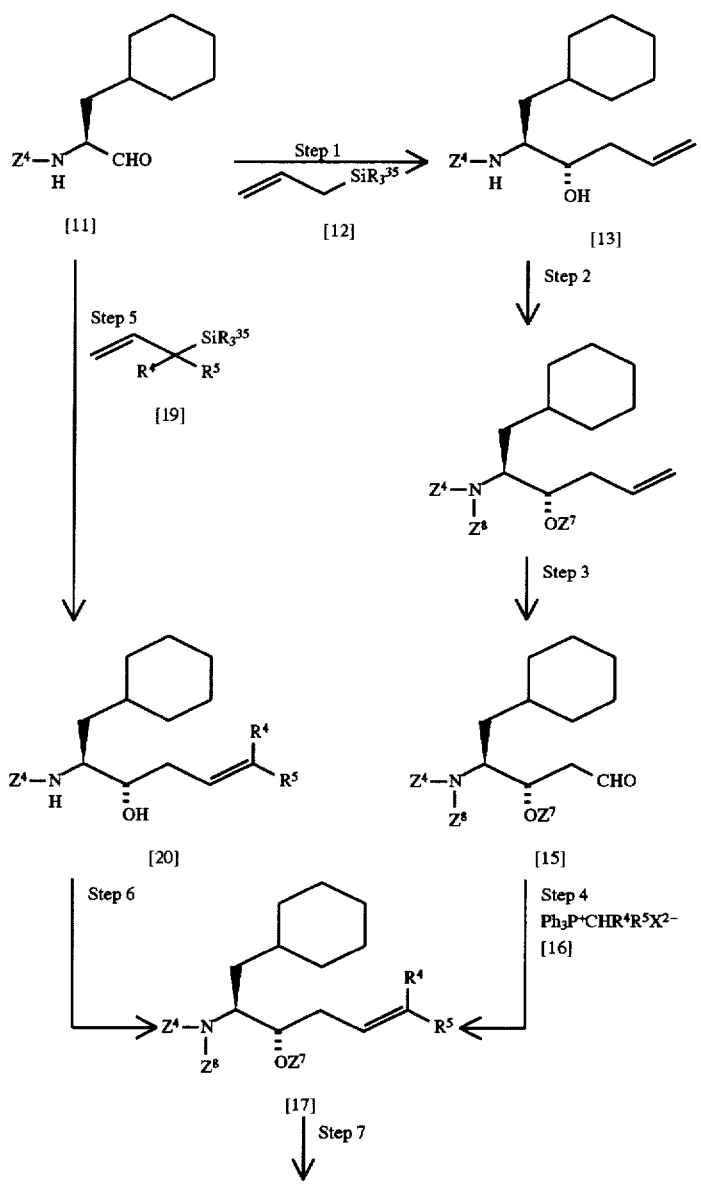

-continued
Production Method A
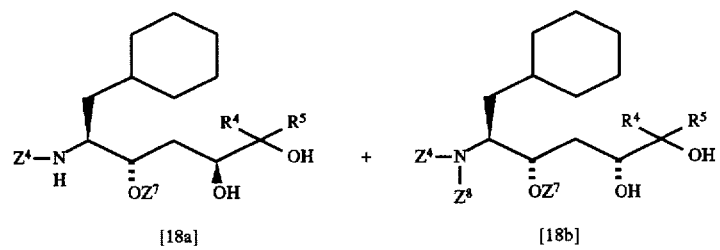
Production Method B
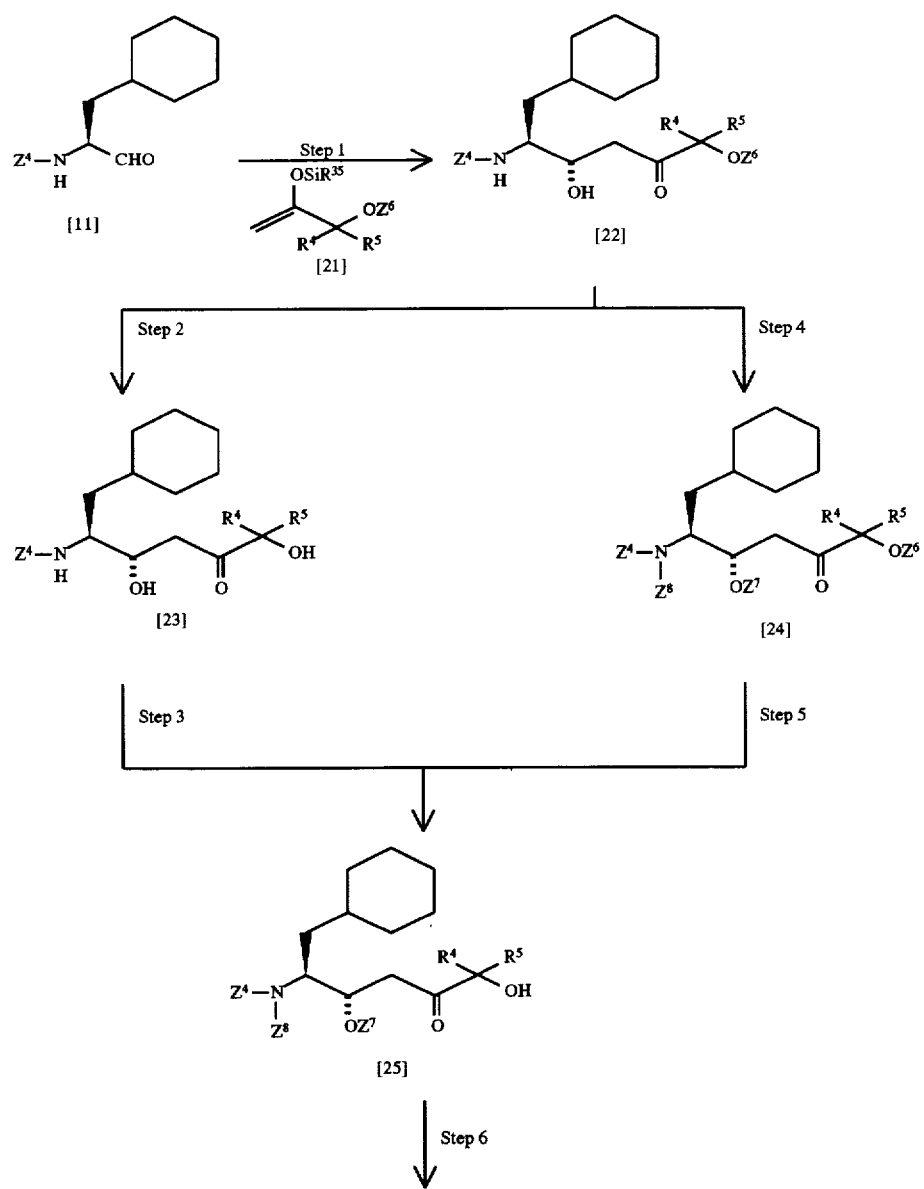

-continued
Production Method B
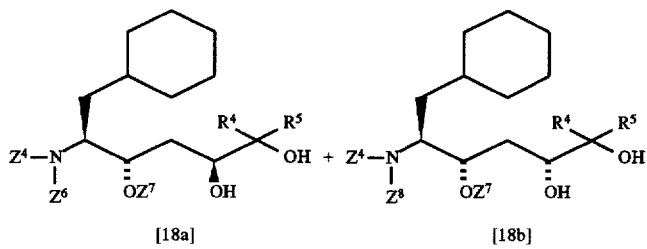
Production Method C
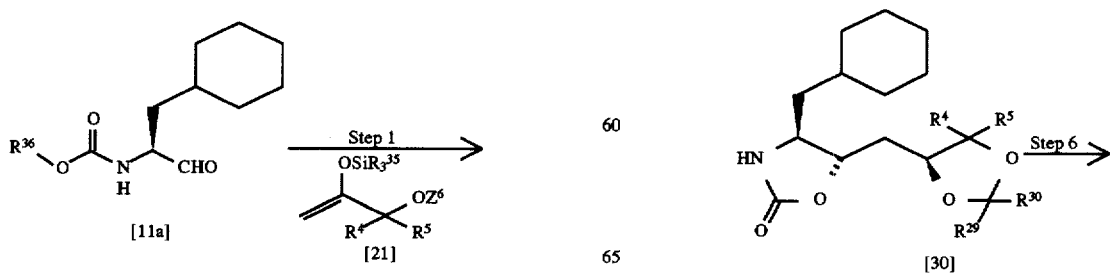
-continued
Production Method D
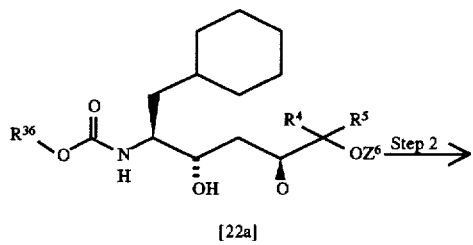
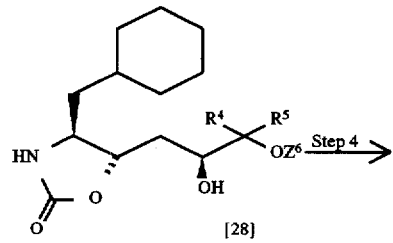

23
-continued
Production Method D

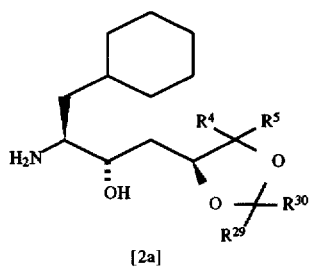

[2a]

Production Method E

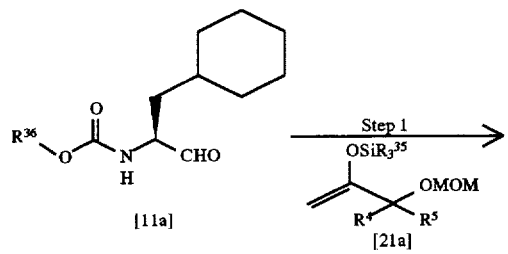

[11a]     [21a]

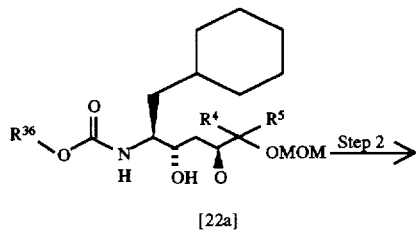

[22a]

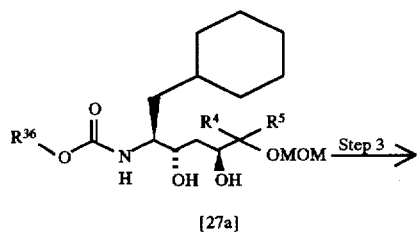

[27a]

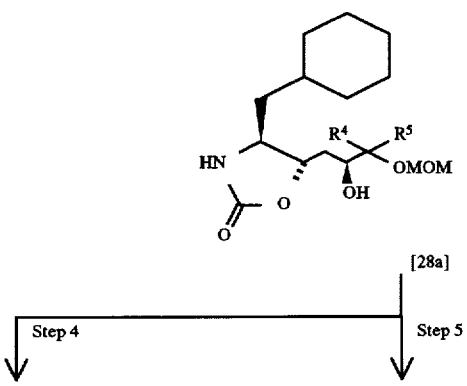

[28a]

Step 4          Step 5

24
-continued
Production Method E

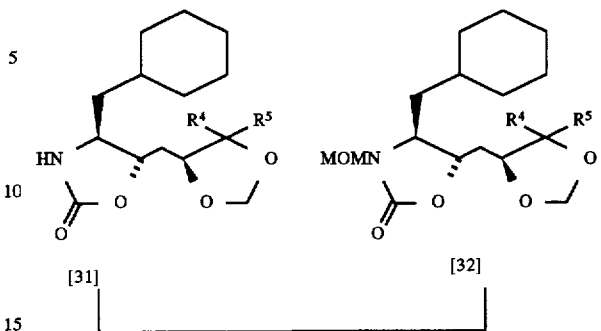

[31]       [32]

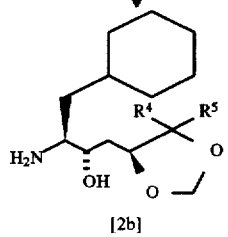

[2b]

wherein A, $R^2$, $R^3$, $R^4$, $R^5$, E, $R^{29}$, $R^{30}$, $R^{35}$, $R^{36}$ and $Z^4$ are as defined above, $P^1$ is an N-protecting group, $P^2$ is a carboxyl-protecting group, $X^2$ is a halogen atom, Ph is phenyl, $Z^7$ is a hydroxyl-protecting group, $Z^8$ is a hydrogen atom or means, together with $Z^7$, an optionally substituted oxazolidine ring or oxazolidinone ring, $Z^6$ is a hydroxyl-protecting group and MOM is methoxymethyl.

The methods for producing the object compounds [1] and intermediates therefor of the present invention are explained in more detail in the following.

Production Method 1

Production of object compound [1]

Step 1

A compound [4] or a salt thereof can be produced by reacting a compound [3], a reactive derivative thereof at the carboxyl group or a salt of the compound [3] or the reactive derivative thereof, with a compound [2], a reactive derivative thereof at the amino group or a salt of the compound [2] or the reactive derivative thereof. This reaction is a so-called peptide forming reaction and can be carried out by a method known per se. Note that $P^1$ of the compound [3] is an N-protecting group such as benzyloxycarbonyl and tert-butoxycarbonyl. The reactive derivative is a derivative obtained by activating a group involved in the reaction, such as carboxyl or amino, by an optional method.

Preferable salts of the compound [4] are those exemplified with regard to the compound [1]. The production of the compound [2] and its analogs is to be described later.

Preferable reactive derivative at carboxyl group of the compound [3] includes, for example, acid halides, acid anhydrides, active amides and active esters. More particularly, they are acid chloride; acid azide; mixed acid anhydride with an acid such as substituted phosphoric acid (e.g. dialkylphosphoric acid, phenylphosphoric acid, diphenyl-phosphoric acid, dibenzylphosphoric acid and halogenated phosphoric acid), dialkylphosphorous acid, sulfurous acid, thiosulfuric acid, sulfuric acid, sulfonic acid (e.g. methane-sulfonic acid), aliphatic carboxylic acid (e.g. acetic acid, propionic acid, butyric acid, isobutyric acid, pivalic acid, pentanoic acid, isopentanoic acid, 2-ethylbutyric acid and trichloroacetic acid) and aromatic carboxylic acid (e.g. benzoic acid); symmetric acid anhydride; active amide with imidazole, 4-substituted imidazole, dimethylpyrazole, triazole or tetrazole; active ester (e.g. cyanomethyl ester, methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, methylphenyl ester, phenylazophenyl ester, phenyl thioester, p-nitrophenyl thioester, p-cresyl thioester, carboxylmethyl thioester, pyranyl ester, pyridyl ester, piperidyl ester and 8-quinolyl thioester), ester with N-hydroxyl compound (e.g. N,N-dimethylhydroxylamine, 1-hydroxy-2-(1H)-pyridone, N-hydroxysuccinimide, N-hydroxyphthalimide and 1-hydroxy-1H-benzotriazole) and the like. These reactive derivatives may be selected appropriately according to the kind of the compound [3] to be used.

Preferable salts of the compound [3] and a reactive derivative thereof include, for example, base salts such as alkali metal salts such as sodium salt and potassium salt, alkaline earth metal salts such as calcium salt and magnesium salt, ammonium salt, salts with organic base (e.g. trimethylamine salt, triethylamine salt, pyridine salt, picoline salt, dicyclohexylamine salt and N,N'-dibenzylethylene diamine salt) and acid addition salts such as inorganic acid addition salt (e.g. hydrochloride, hydrobromide, sulfate and phosphate).

Preferable reactive derivatives at the amino group of the compound [2] include, for example, Schiff base type imino group formed by the reaction of a compound [2] with a carbonyl compound such as aldehyde and ketone, or an enamine tautomer thereof; silyl derivative formed by the reaction of a compound [2] with a silyl compound such as bis(trimethylsilyl)acetamide, mono(trimethylsilyl) acetamide and bis(trimethylsilyl)urea; and derivative formed by the reaction of a compound [2] with phosphorus trichloride or phosgene.

Preferable salts of the compound [2] and a reactive derivative thereof are those exemplified with regard to the compound [4].

The reaction is generally carried out in a conventional solvent such as water, alcohol (e.g. methanol and ethanol), acetone, dioxane, acetonitrile, chloroform, methylene chloride, ethylene chloride, tetrahydrofuran, ethyl acetate, N,N-dimethylformamide and pyridine. Any other organic solvent may be used as long as it does not exert adverse influences on the reaction. These conventional solvents may be used as a mixture with water.

When the compound [3] is used in the form of a free acid or a salt thereof in this reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylamino-cyclohexyl) carbodiimide; N,N'-diethylcarbodiimide; N,N'-diisopropylcarbodiimide; N-ethyl-N'-(3-dimethylaminopropyl)-carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite, ethyl polyphosphate; isopropyl polyphosphate; phosphorus oxychloride (phosphoryl chloride); phosphorus trichloride; diphenylphosphoryl azide; diethyl cyanophosphate; thionyl chloride; oxalyl chloride; lower alkyl haloformate (e.g. ethyl chloroformate and isopropyl chloroformate); triphenylphosphine; 2-ethyl-7-hydroxybenziso-oxazolium salt; 2-ethyl-5-(m-sulfophenyl) isoxazolium hydroxide intramolecular salt; 1-(p-chlorobenzenesulfonyloxy)-6-chloro-1H-benzotriazole; and so-called Vilsmeier Reagent prepared by reacting N,N-dimethylformamide with thionyl chloride, phosgene, trichloromethyl chloroformate, phosphorus oxychloride or the like.

The reaction may be carried out in the presence of an inorganic base or an organic base such as alkali metal hydrogencarbonate, tri(lower)alkylamine, pyridine, N-(lower)-alkylmorpholine and N,N-di(lower) alkylbenzylamine.

While the reaction temperature is not particularly limited, the reaction is carried out from under cooling to under heating.

Step 2

A compound [5] or a salt thereof can be produced by subjecting a compound [4] or a salt thereof to the elimination of N-protecting group.

Preferable salts of the compound [5] are those exemplified for the compound [3].

The elimination is carried out by a conventional method such as hydrolysis and reduction.

The hydrolysis is preferably carried out in the presence of a base or an acid including a Lewis acid.

Preferable base includes, for example, inorganic base and organic base, such as alkali metal (e.g. sodium and potassium), alkaline earth metal (e.g. magnesium and calcium), hydroxide, carbonate or hydrogencarbonate of these metals, hydrazine, trialkylamine (e.g. trimethylamine and triethylamine), picoline, 1,5-diazabicyclo|4.3.0|non-5-ene, 1,4-diazabicyclo[2.2.2] octane and 1,8-diazabicyclo [5.4.0]undec-7-ene. Preferable acids include organic acids such as formic acid, acetic acid, propionic acid, trichloroacetic acid, trifluoroacetic acid and 1-hydroxybenzotriazole, inorganic acids such as hydrochloric acid, hydrobromic acid, sulfuric acid, hydrogenchloride, hydrogenbromide and hydrogenfluoride, and acid addition salt compounds such as pyridine hydrochloride.

An elimination using a Lewis acid such as boron trifluoride is preferably performed in the presence of a cation trapping agent such as anisole and phenol.

The reaction generally proceeds in a solvent such as water, alcohol (e.g. methanol and ethanol), methylene chloride, chloroform, tetrachloromethane and tetrahydrofuran or a mixture thereof. Any other solvent may be used as long as it does not adversely influence the reaction. A liquid base or acid may be used as a solvent. The reaction temperature is not particularly limited and the reaction is generally carried out from under cooling to under heating.

The reduction applicable to the elimination is chemical reduction and catalytic reduction.

Preferable reducing agent to be used for the chemical reduction is exemplified by a combination of a metal such as tin, zinc and iron, and an acid such as formic acid, acetic acid, propionic acid and trifluoroacetic acid.

Preferable reducing agent to be used for the catalytic reduction is exemplified by conventional ones such as platinum catalysts (e.g. platinum black and platinum oxide), palladium catalysts (e.g. palladium black, palladium oxide and palladium-carbon), nickel catalysts (e.g. reduced nickel and Raney nickel), and iron catalysts (e.g. reduced iron and Raney iron).

Reduction is generally carried out in a conventional solvent which does not exert adverse influences on the reaction, such as water, methanol, ethanol, propanol and N,N-dimethylformamide, or a mixture thereof. When the above-mentioned acid to be used for the chemical reduction is a liquid, the acid may be used as a solvent. Examples of the preferable solvent to be used for the catalytic reduction include the above-mentioned solvents, diethyl ether, dioxane and tetrahydrofuran. Any other solvent may be used as long as it does not adversely influence the reaction.

The reaction temperature is not particularly limited and the reaction is generally carried out from under cooling to under heating.

Step 3

The object compound [1] or a salt thereof can be produced by reacting a compound [6], a reactive derivative at the carboxyl group or a salt of the compound or the derivative, with a compound [5], a reactive derivative at the amino group or a salt of the compound or the derivative, to form a peptide bond, followed by elimination of N-protecting group, carboxyl-protecting group, hydroxyl-protecting group and thiol-protecting group, as necessary.

Preferable reactive derivative at the carboxyl group of the compound [6] and salts thereof are those exemplified for the compound [3].

Preferable reactive derivative at the amino group of the compound [5] and salts thereof are those exemplified for the compound [2].

This reaction is a peptide forming reaction and can be carried out in substantially the same manner as in Step 1. Accordingly, the method for the reaction and the conditions therefor are to be determined by reference to the description in Step 1.

For the smooth progress of the aforementioned Steps 1–3, amino, imino, carboxyl, hydroxy and thiol, which are not involved in the reaction, may be protected as necessary. The protection may be done before any of the Steps 1–3. Also, the elimination of these protecting groups may be done after any of the Steps 1–3. The preferable protecting group, and the method for protection and deprotection thereof may be determined according to a known method [T. W. Greene and P. G. M. Wuts, Protective Groups in Organic Synthesis, John Wiley & Sons, N.Y. (1991), and *Pepuchido Gosei no Kiso to Jikken*, Maruzen, Tokyo (1987)].

Production Method 2

Production of object compound [1]

Step 1

A compound [8] or a salt thereof can be produced by reacting a compound [7], a reactive derivative thereof at the amino group or a salt of the compound or the reactive derivative thereof, with a compound [6], a reactive derivative thereof at the carboxyl group or a salt of the compound or the reactive derivative thereof. Note that $P^2$ of the compound [7] is a carboxyl-protecting group such as methyl and benzyl.

The preferable reactive derivative at the amino group of the compound [7] and preferable salts thereof are those exemplified for the compound [2].

The preferable salts of the compound [8] are those exemplified for the compound [1].

This reaction is a peptide forming reaction and can be carried out in substantially the same manner as in Step 1 of the aforementioned Production method 1. Accordingly, the method for the reaction and the conditions therefor are to be determined by reference to the description in Step 1 of Production method 1.

Step 2

A compound [9] or a salt thereof can be produced by subjecting a compound [8] or a salt thereof to the elimination of carboxyl-protecting group $P^2$.

The preferable salts of the compound [9] are those exemplified for the compound [3].

The reaction is carried out by a conventional method such as hydrolysis and reduction.

The hydrolysis is preferably carried out in the presence of a base or an acid.

The preferable bases are, for example, alkali metal such as sodium and potassium, hydroxides and carbonates of these metals.

The preferable acids are, for example, hydrochloric acid, hydrobromic acid, sulfuric acid, hydrogen chloride, hydrogen bromide and hydrogen fluoride.

The hydrolysis generally proceeds in an inert solvent such as water, alcohol (e.g. methanol and ethanol), methylene chloride, chloroform, tetrachloromethane and tetrahydrofuran or a mixture thereof. Any other solvent may be used as long as it does not adversely influence the reaction. A liquid base or acid may be used as a solvent. The temperature of the hydrolysis is not particularly limited and the reaction is generally carried out from under cooling to under heating.

The reductions applicable to the elimination are chemical reduction and catalytic reduction.

These reductions are substantially the same as those for the above-mentioned elimination of the N-protecting group. Accordingly, the reaction conditions such as reducing agent and catalyst are to be determined by reference to the description of chemical reduction and catalytic reduction in Step 2 of Production method 1.

The reactive derivative at the carboxyl group of the compound [9] usable in the next step or a salt thereof can be produced from the compound [8] and a salt thereof, not to mention the compound [9]. For example, elimination of carboxyl-protecting group, when hydrazine or benzyloxycarbonyl hydrazide is used, can be carried out by converting the compound [8] or a salt thereof to an acid azide derivative, which is a reactive derivative of the compound [9] at the carboxyl group, via an acid hydrazide derivative of the compound [9] instead of the compound [9].

The preferable salts of the reactive derivative of the compound [9] are those exemplified for the compound [3].

Step 3

An object compound [1] or a salt thereof can be produced by condensing a compound [2], a reactive derivative thereof at the amino group or a salt of the compound or the reactive derivative, with a compound [9], a reactive derivative thereof at the carboxyl group or a salt of the compound or the reactive derivative, to form a peptide bond, followed by elimination of N-protecting group, hydroxyl-protecting group and thiol-protecting group, as necessary.

Preferable reactive derivative at the carboxyl group of the compound [9] and salts thereof are those exemplified for the compound [3].

This reaction is a peptide forming reaction and can be carried out in substantially the same manner as in Step 1 of the aforementioned Production method 1. Accordingly, the reaction, the method for the reaction and the conditions therefor are to be determined by reference to the description in Step 1 of the aforementioned Production method 1.

For the smooth progress of the aforementioned Steps 1–3, amino, imino, carboxyl, hydroxy and thiol which are not involved in the reaction may be protected as necessary. The protection may be done before any of the Steps 1–3. Also, the elimination of these protecting groups may be done after any of the Steps 1–3. The preferable protecting group, and the method for protection and deprotection thereof may be determined by reference to the description in Step 3 of Production method 1.

Production Method A
Production of intermediates [18a] and [18b]
Step 1

A compound [13] can be produced by reacting a compound [11] with a compound [12] in the presence of a Lewis acid.

Note that $Z^4$ of the compound [11] is an N-protecting group such as tert-butoxycarbonyl and benzyloxycarbonyl, and $R^{35}$ of the compound [12] is a lower alkyl. The Lewis acid to be used is exemplified by tin tetrachloride, titanium tetrachloride and boron trifluoride-ether complex, with preference given to tin tetrachloride. The instant reaction is carried out in a solvent and the solvent to be used may be any as long as it is not involved in the reaction. Preferred are aprotic solvents such as dichloromethane, chloroform and toluene. The reaction temperature is not more than room temperature, and is preferably from −80° C. to 0° C. The instant reaction proceeds with stereoselectivity of the hydroxyl moiety of the compound [13] of S:R=9:1, and recrystallization, separation by chromatography and the like yield an isomerically pure compound [13] (S configuration of the hydroxyl moiety) with ease and at high yields.

Step 2

A compound [14] can be produced by protecting the hydroxyl group of the compound [13].

Note that $Z^7$ of the compound [14] is a hydroxyl-protecting group and $Z^8$ is a hydrogen atom or may form, together with $Z^7$, an optionally substituted oxazolidine ring or an oxazolidinone ring.

In the compound [14], when $Z^8$ is a hydrogen atom, the hydroxyl group of the compound [13] may be protected by a known method [T. W. Greene and P. G. M. Wuts, Protective Groups in Organic Synthesis, John Wiley & Sons, N.Y. (1991)].

When $Z^7$ and $Z^8$ of the compound [14] combinedly form an optionally substituted oxazolidine ring, a compound [13] is reacted with acetone, 2,2-dimethoxypropane, 2-methoxypropene, cyclohexanone, 1,1-dimethoxycyclohexane, acetaldehyde, 1,1-dimethoxyethane, butylaldehyde, benzaldehyde, benzaldehyde dimethyl acetal and the like, using an acid including a Lewis acid as a catalyst. Preferable acid includes, for example, organic acid such as p-toluenesulfonic acid and pyridine p-toluenesulfonate. The reaction is carried out without a solvent or in a solvent which is not involved in the reaction, with preference given to dichloromethane, tetrahydrofuran and toluene. While the reaction temperature is not particularly limited, the reaction generally proceeds from under cooling to under heating.

When $Z^7$ and $Z^8$ of the compound [14] combinedly form an oxazolidinone ring, a compound [13] wherein $Z^4$ is a lower alkoxycarbonyl such as ethoxycarbonyl and tert-butoxycarbonyl or aralkyloxycarbonyl such as benzyloxycarbonyl and p-nitrobenzyloxycarbonyl is subjected to cyclocondensation in the presence of a base. Preferable base includes, for example, hydroxides of alkali metal or alkaline earth metal, such as sodium hydroxide and potassium hydroxide, and metal hydride compounds such as sodium hydride and potassium hydride. When a hydroxide of alkali metal or alkaline earth metal is used as a base, the reaction is generally carried out in a mixed solvent of water and alcohol (e.g. methanol and ethanol), dioxane or the like, and when a metal hydride is used as a base, the reaction is generally carried out in a solvent which does not influence the reaction, such as tetrahydrofuran and N,N-dimethylformamide. While the reaction temperature is not particularly limited, the reaction generally proceeds from under cooling to room temerature.

Step 3

A compound [15] can be produced by oxidation cleavage of the olefin moiety of a compound [14]. The method for the oxidation cleavage may be a known method [Shinjikken Kagaku Koza 15, Sanka to Kangen I-1,2, Maruzen, Tokyo (1976)] such as a method using ozone and a method using osmium tetraoxide-sodium periodate.

Step 4

A compound [17] can be produced by a Wittig reaction wherein a compound [15] and a phosphonium salt [16] are reacted in the presence of a base. Note that $R^4$ and $R^5$ of the compound [16] are as defined above, $X^2$ is a halogen atom and Ph is phenyl. The phosphonium salt [16] can be produced by the reaction of a corresponding alkyl halide and triphenylphosphine. The instant reaction is carried out by a known method [Shinjikken Kagaku Koza 14, Yukikagobutsu no Gosei to Hannou I, Maruzen, Tokyo (1977)].

Step 5

A compound [20] can be produced by reacting a compound [11] and a compound [19] in the presence of a Lewis acid. Note that $R^4$, $R^5$ and $R^{35}$ of the compound [19] are as defined above. This reaction can be carried out in substantially the same manner as in Step 1 of the aforementioned Production method A. Accordingly, the method for the reaction and the conditions therefor are to be determined by reference to the description in Step 1 of the aforementioned Production method A.

Step 6

A compound [17] can be produced by protecting a hydroxyl group of a compound [20]. Note that $Z^7$ and $Z^8$ of the compound [17] are as defined above. This reaction can be carried out in substantially the same manner as in Step 2 of the aforementioned Production method A. Accordingly, the method for the reaction and the conditions therefor are to be determined by reference to the description in Step 2 of the aforementioned Production method A.

Step 7

A compound [18a] and a compound [18b] can be produced by oxidizing the olefin moiety of the compound [17]. The method for the oxidation may be a known method [Shinjikken Kagaku Koza 14, Yukikagobutsu no Gosei to Hannou I, Maruzen, Tokyo (1977)], such as a method using potassium permanganate and a method using osmium tetraoxide and N-methylmorpholine-N-oxide.

Separation of the isomers [18a] and [18b] can be done by the step of recrystallization or chromatography, whereby isomrically pure compounds can be obtained.

Production Method B
Production of intermediates [18a] and [18b]
Step 1

A compound [22] can be produced by reacting a compound [11] and a compound [21] in the presence of a Lewis acid.

Note that $Z^4$ of the compound [11] means an N-protecting group, $R^4$, $R^5$ and $R^{35}$ of the compound [21] are as defined above and $Z^6$ is a hydroxyl-protecting group such as trimethylsilyl and methoxymethyl. Examples of the Lewis acid to be used include tin tetrachloride, titanium tetrachloride and boron trifluoride-ether complex, with preference given to boron trifluoride-ether complex. The instant reaction is carried out in a solvent. While the solvent may be any as long as it is not involved in the reaction, preferred are aprotic solvents such as dichloromethane, chloroform and toluene. The reaction temperature is not more than room temperature, and is preferably from −80° C. to 0° C. The instant reaction proceeds with stereoselectivity of the hydroxyl moiety of the compound [22] of S:R=9:1, and recrystallization, separation by chromatography and the like yield an isomerically pure compound [22] (S configuration of the hydroxyl moiety) with ease and at high yields.

Step 2

A compound [23] can be produced by subjecting a compound [22] to the elimination of a hydroxyl-protecting group $Z^6$. The elimination is carried out by a known method [T. W. Greene and P. G. M. Wuts, Protective Groups in Organic Synthesis, John Wiley & Sons, N.Y. (1991)].

Step 3

A compound [25] can be produced by protecting the hydroxyl group of a compound [23]. Note that $Z^7$ and $Z^8$ of the compound [25] are as defined above. This reaction can be carried out in substantially the same manner as in Step 2 of the aforementioned Production method A. Accordingly, the method for the reaction and the conditions therefor are to be determined by reference to the description in Step 2 of the aforementioned Production method A.

Step 4

A compound [24] can be produced by protecting the hydroxyl group of a compound [22]. Note that $Z^7$ and Z8 of the compound [24] are as defined above. This reaction can be carried out in substantially the same manner as in Step 2 of the aforementioned Production method A. Accordingly, the method for the reaction and the conditions therefor are to be determined by reference to the description in Step 2 of the aforementioned Production method A.

Step 5

A compound [25] can be produced by subjecting a compound [24] to the elimination of a hydroxyl-protecting group $Z^6$. The deprotection is carried out by a known method [T. W. Greene and P. G. M. Wuts, Protective Groups in Organic Synthesis, John Wiley & Sons, N.Y. (1991)].

Step 6

A compound [18a] and a compound [18b] can be produced by reducing the carbonyl group of the compound [25]. The method for reduction applicable to the instant reaction includes chemical reduction and catalytic reduction.

Preferable reducing agent to be used chemically is exemplified by metal hydrides such as sodium borohydride, lithium borohydride, zinc (II) borohydride and lithium aluminum hydride, metals such as lithium, sodium and zinc, aluminum alkoxide, triisobutyl aluminum and diborane.

Preferable catalyst to be used for the catalytic reduction include, for example, those to be used for the catalytic reduction in the above-mentioned Step 2 of Production method 1.

The reduction is generally carried out in a conventional solvent which does not exert adverse influences on the reaction, such as water, methanol, ethanol, propanol, tetrahydrofuran, ether and N,N-dimethylformamide, or a mixture thereof. While the reaction temperature is not particularly limited, the reaction generally proceeds from under cooling to under heating.

Separation of the isomers [18a] and [18b] can be done by the step of recrystallization or chromatography, whereby isomrically pure compounds can be respectively obtained.

Production Method C

Production of intermediate [2]

Step 1

A compound [26] can be produced by reacting a compound [18] with formaldehyde, paraformaldehyde, acetone, dimethoxymethane, 2,2-dimethoxypropane, 2-methoxypropene, cyclohexanone, 1,1-dimethoxycyclohexane, acetaldehyde, 1,1-dimethoxyethane, butylaldehyde, benzaldehyde, benzaldehyde dimethyl acetal or the like, using an acid including a Lewis acid as a catalyst, or by reacting a compound [18] with dibromomethane, diiodemethane, 1,2-dibromoethane, 1,2-diiodoethane, ethylene glycol ditosylate or the like, in the presence of a base. Preferable acid includes, for example, inorganic acid such as sulfuric acid and organic acid such as p-toluenesulfonic acid and pyridine p-toluenesulfonate. Preferable base includes, for example, hydroxides, carbonates or hydrogencarbonates of alkali metal or alkaline earth metal, such as sodium hydroxide and potassium carbonate, and metal hydride compounds such as sodium hydride and potassium hydride. This reaction is generally carried out in a solvent which does not influence the reaction, such as tetrahydrofuran, toluene, dichloromethane and N,N-dimethylformamide. While the reaction temperature is not particularly limited, the reaction generally proceeds from under cooling to under heating.

Step 2

A compound [2] can be produced by elimination of N-protecting group and hydroxyl-protecting group of a compound [26]. The deprotection can be done by simultaneously eliminating the N-protecting group and the hydroxyl-protecting group of the compound [26] under the same conditions, or by sequentially eliminating the protecting groups under different conditions. When sequentially eliminating under different conditions, either the N-protecting group or the hydroxyl-protecting group may be eliminated first. The method for the elimination may be known [T. W. Greene and P. G. M. Wuts, Protective Groups in Organic Synthesis, John Wiley & Sons, N.Y. (1991)]. As a specific example, a compound [26], wherein $Z^4$ is benzyloxycarbonyl and $Z^7$ and $Z^8$ combinedly form the oxazolidine ring, is subjected to ring opening of the oxazolidine ring by hydrolysis under the acidic conditions, followed by reduction to eliminate the benzyloxycarbonyl, whereby a compound [2] is obtained.

Production Method D

Production of intermediate [2a]

Step 1

A compound [22a] can be produced by reacting a compound [11a] with a compound [21] in the presence of a Lewis acid. Note that $R^{36}$ of a compound [11a] is a lower alkyl or benzyl and $R^4$, $R^5$, $R^{35}$ and $Z^6$ of the compound [21] are as defined above. This reaction can be carried out in substantially the same manner as in Step 1 of the aforementioned Production method B. Accordingly, the method for the reaction and the conditions therefor are to be determined by reference to the description in Step 1 of the aforementioned Production method B. The instant reaction proceeds with stereoselectivity of the hydroxyl moiety of the compound [22a] of S:R=9:1, and recrystallization, separation by chromatography and the like yield an isomerically pure compound [22a] (S configuration of the hydroxyl moiety) with ease and at high yields.

Step 2

A compound [27] can be produced by reducing the carbonyl group of a compound [22a] with a boron hydride compound such as sodium borohydride and tetramethylammonium borohydride in the presence of an organic acid such as acetic acid and propionic acid. The reaction proceeds highly stereoselectively and the ratio of the formed (2S,4S, 5S)-5-amino-6-cyclohexyl-2,4-hexanediol derivative which is expressed by [27], and its stereoisomer (2R,4S,5S)-5-amino-6-cyclohexyl-2,4-hexanediol derivative is not less than 9:1.The compound [27] can be obtained as an isomerically pure compound with ease and at high yields by recrystallization, separation by chromatography and the like. The method for the reaction and the conditions therefor are to be determined by reference to a known method, *Journal of American Chemical Society*, vol. 110, 3560-3578 (1988) and WO 9213827.

Step 3

A compound [28] can be produced by cyclocondensation of a compound [27] in the presence of a base. Preferable base includes, for example, hydroxides of alkali metal or alkaline earth metal, such as sodium hydroxide and potassium hydroxide, and metal hydride compounds such as sodium hydride and potassium hydride. This reaction is generally carried out in a mixed solvent of water and alcohol (e.g. methanol and ethanol) or dioxane when a hydroxide of alkali metal or alkaline earth metal is used as a base, and when a metal hydride compound is used as a base, the reaction is carried out in a solvent which does not influence the reaction, such as tetrahydrofuran and N,N-dimethylformamide. While the reaction temperature is not particularly limited, the reaction generally proceeds from under cooling to room temerature.

Step 4

A compound [29] can be produced by subjecting a compound [28] to the elimination of a hydroxyl-protecting group $Z^6$. The deprotection is carried out by a known method [T. W. Greene and P. G. M. Wuts, Protective Groups in Organic Synthesis, John Wiley & Sons, N.Y. (1991)].

Step 5

A compound [30] can be produced by reacting a compound [29] with formaldehyde, paraformaldehyde, acetone, dimethoxymethane, 2,2-dimethoxypropane, 2-methoxypropene, cyclohexanone, 1,1-dimethoxycyclohexane, acetaldehyde, 1,1-dimethoxyethane, butylaldehyde, benzaldehyde, benzaldehyde dimethyl acetal or the like, using an acid incuding a Lewis acid as a catalyst. Preferable acid includes, for example, inorganic acid such as sulfuric acid and organic acid such as p-toluenesulfonic acid and pyridine p-toluenesulfonate. This reaction is generally carried out in a solvent which does not influence the reaction, such as tetrahydrofuran, toluene, dichloromethane and N,N-dimethylformamide. While the reaction temperature is not particularly limited, the reaction generally proceeds from under cooling to under heating. The instant reaction is accelerated by the coexistence of lithium bromide.

Step 6

A compound [2a] can be produced by ring opening of a compound [30] by hydrolysis using a base. Preferable base includes, for example, hydroxides of alkali metal or alkaline earth metal, such as sodium hydroxide, potassium hydroxide and barium hydroxide. This reaction is generally carried out in a mixed solvent of water and alcohol (e.g. methanol and ethanol) or dioxane. The reaction generally proceeds from under cooling to under heating, with preference given to a solvent refluxing temperature where the reaction proceeds speedily.

Production Method E

Production of intermediate [2b]

Step 1

A compound [22b] can be produced by reacting a compound [11a] with a compound [21a] in the presence of a Lewis acid. Note that $R^{36}$ of a compound [11a] is a lower alkyl or benzyl, MOM in the compound [21a] is methoxymethyl, and $R^4$, $R^5$ and $R^{35}$ are as defined above. This reaction can be carried out in substantially the same manner as in Step 1 of the aforementioned Production method B. Accordingly, the method for the reaction and the conditions therefor are to be determined by reference to the description in Step 1 of the aforementioned Production method B. The instant reaction proceeds with stereoselectivity of the hydroxyl moiety of the compound [22b] of S:R=9:1, and recrystallization, separation by chromatography and the like yield an isomerically pure compound [22b] (S configuration of the hydroxyl moiety) with ease and at high yields.

Step 2

A compound [27a] can be produced by reducing the carbonyl group of a compound [22b] with a boron hydride compound such as sodium borohydride and tetramethyl ammonium borohydride in the presence of a lower alkylcarboxylic acid such as acetic acid and propionic acid. The reaction proceeds highly stereoselectively and the ratio of the formed (2S,4S,5S)-5-amino-6-cyclohexyl-1-methoxymethoxy-2,4-hexanediol derivative which is expressed by [27a] and its stereoisomer (2R,4S,5S)-5-amino-6-cyclohexyl-1-methoxymethoxy-2,4-hexanediol derivative is not less than 9:1. The compound [27a] can be obtained as an isomerically pure compound with ease and at high yields by recrystallization, separation by chromatography and the like. The method for the reaction and the conditions therefor are to be determined by reference to a known method, *Journal of American Chemical Society*, vol. 110, 3560–3578 (1988) and WO 9213827.

Step 3

A compound [28a] can be produced by cyclocondensation of a compound [27a] in the presence of a base. Preferable base includes, for example, hydroxides of alkali metal or alkaline earth metal, such as sodium hydroxide and potassium hydroxide, and metal hydride compounds such as sodium hydride and potassium hydride. This reaction is generally carried out in a mixed solvent of water and alcohol (e.g. methanol and ethanol) or dioxane when a hydroxide of alkali metal or alkaline earth metal is used as a base, and when a metal hydride compound is used as a base, the reaction is carried out in a solvent which does not influence the reaction, such as tetrahydrofuran and N,N-dimethylformamide. While the reaction temperature is not particularly limited, the reaction generally proceeds from under cooling to room temperature.

An isomerically pure compound [28a] can be produced with ease and at high yields by recrystallization after the reaction of the instant step, instead of purification in Production method E, Step 1 and Step 2 (compounds [22b] and [27a]).

Step 4

A compound [31] can be produced by cyclocondensation of a compound [28a] in the presence of diphosphorus pentaoxide or a Lewis acid such as a boron trifluoride-ether complex. The reaction is generally carried out in a solvent which does not influence the reaction, such as tetrahydrofuran, toluene and dichloromethane. While the reaction temperature is not particularly limited, the reaction generally proceeds from under cooling to under heating.

Step 5

A compound [32] can be produced by reacting a compound [28a] with dimethoxymethane using an acid including a Lewis acid as a catalyst. Preferable acid includes, for example, inorganic acid such as sulfuric acid and organic acid such as p-toluenesulfonic acid and pyridine p-toluenesulfonate. This reaction is generally carried out in a solvent which does not influence the reaction, such as tetrahydrofuran, toluene, dichloromethane and N,N-dimethylformamide. While the reaction temperature is not particularly limited, the reaction generally proceeds from under cooling to under heating, with preference given to under heating which increases the reaction speed. The instant reaction is accelerated by the coexistence of lithium bromide.

Step 6

A compound [2b] can be produced by ring opening of a compound [31] or [32] by hydrolysis using a base. Preferable base includes, for example, hydroxides of alkali metal or alkaline earth metal, such as sodium hydroxide, potassium hydroxide and barium hydroxide. This reaction is generally carried out in a mixed solvent of water and alcohol (e.g. methanol and ethanol) or dioxane. The reaction temperature is generally from under cooling to under heating, with preference given to a solvent refluxing temperature, at which the reaction proceeds speedily.

The compounds obtained by the aforementioned Production methods can be separated and purified by conventional methods such as pulverizing, recrystallization, column chromatography and reprecipitation.

The compound [1] of the present invention and the intermediate compounds therefor include one or more stereoisomers based on asymmetric carbon. Such isomers and mixtures thereof are encompassed in the scope of the present invention.

The compound [1] of the present invention and the pharmaceutically acceptable salts thereof can be used as a pharmaceutical preparation suitable for oral administration, parenteral administration or external administration, by admixing the compound or a salt thereof as an active ingredient, with organic or inorganic, solid or liquid excipients. Examples of the pharmaceutical preparation include capsule, tablet, sugar-coated tablet, granule, solution, suspension, emulsion and the like. When desired, auxiliaries, stabilizers, lubricants or emulsifiers, buffers and other conventionally employed additives may be contained in these preparations.

While the dose varies depending on age and conditions of patients, a dose of 0.1 mg/individual—ca. 1000 mg/individual per day on average is effective for the treatment of hypertension and heart failure.

In the present invention, the compounds represented by the formulas [II], [III], [IV], [V], [VI] and [VII] are novel and useful as intermediates for the production of the compound [1]. The object compound [1] can be produced from these intermediates by the aforementioned Production methods.

EXAMPLES

The present invention is described in more detail by way of the following Production Examples and Examples. The symbols used in Production Examples, Examples and Tables mean the following.

NMR : nuclear magnetic resonance spectrum
FAB : fast atom bombardment mass spectrometry
AcOEt : ethyl acetate Hex : hexane
CHCl$_3$ : chloroform MeOH : methanol
NH$_4$OH : 28% aqueous ammonia AcOH : acetic acid
Cbz : benzyloxycarbonyl PMSF : phenylmethylsulfonyl fluoride
DMF : N,N-dimethylformamide
PPTS : pyridine p-toluenesulfonate
TMS : trimethylsilyl MOM : methoxymethyl
Bn : benzyl In the following Examples and Production Examples, Rf value of thin layer chromatography was obtained with the use of Pre-coated TLC Plates SILICA GEL 60 F-254 (thickness 0.25 mm) manufactured by Merck; preparative thin layer chromatography was done with the use of Pre-coated SILICA GEL 60 F-254 (thickness 0.25–2 mm) manufactured by Merck; and column chromatography was done with the use of Kieselgel 60 (70-230 mesh or 230-400 mesh) manufactured by Merck.

Production Example 1
(4S,5S)-5-benzyloxycarbonylamino-6-cyclohexyl-4-hydroxy-1-hexene A solution of N-benzyloxycarbonyl-L-cyclohexylalaninal (6.9 g) in dichloromethane (70 ml) was cooled to –40° C. and a solution of tin tetrachloride (3.1 ml) in dichloromethane (20 ml) was dropwise added. After stirring the mixture at –40° C. for 5 minutes, a solution of allyltrimethylsilane (4.2 ml) in dichloromethane (30 ml) was dropwise added, followed by stirring for 30 minutes. The reaction mixture was added to an ice-cooled saturated aqueous solution of NaHCO$_3$ and extracted twice with diethyl ether. The organic layer was washed twice with a saturated aqueous solution of NaHCO$_3$ and once with saturated brine. The layer was dried over MgSO$_4$ and the solvent was distilled away under reduced pressure. The residue was purified by silica gel column chromatography (eluted with AcOEt/Hex= 1/9 v/v) to give 4.4 g of a colorless, oily title compound (see Table 1).

Production Example 2
(4S,5S)-5-allyl-3-benzyloxycarbonyl-4-cyclohexylmethyl-2,2-dimethyl-1,3-oxazolidine 2-Methoxypropene (0.64 ml) and PPTS (834 mg) were added to a solution of the compound (2.2 g) obtained in Production Example 1 in dichloromethane, and the mixture was stirred at room temperature for 1 hour. After adding powdery NaHCO$_3$, the reaction mixture was filtered and the filtrate was concentrated under reduced pressure. Water was added to the residue and the mixture was extracted with diethyl ether. The organic layer was washed with water and saturated brine and dried over MgSO$_4$. The solvent was distilled away under reduced pressure and the residue was purified by silica gel column chromatography (eluted with AcOEt/Hex=5/95 v/v) to give 1.3 g of a colorless, oily title compound (see Table 1).

Production Example 3
(4S,5S)-3-benzyloxycarbonyl-4-cyclohexylmethyl-2,2-dimethyl-1,3-oxazolidine-5-acetaldehyde The compound (2.2 g) obtained in Production Example 2 was dissolved in a mixed solvent of methanol (20 ml) and dichloromethane (40 ml), and the mixture was cooled to –75° C., followed by aeration of ozone through the solution. After the reaction mixture turned blue (1.5 hr), dry nitrogen was aerated to remove excessive ozone. The reaction mixture was dropwise added to a suspension of zinc powder (1.2 g), acetic acid (1.2 ml), methanol (25 ml) and water (25 ml) at –45° C. with a cannula. The temperature of the mixture was raised to room temperature and the mixture was stirred for 30 minutes. The mixture was extracted twice with dichloromethane and washed with a saturated aqueous solution of NaHCO$_3$. The organic layer was dried over MgSO$_4$. The solvent was distilled away under reduced pressure to give 2.3 g of a colorless, oily title compound (see Table 1).

Production Example 4
(4S,5S)-3-benzyloxycarbonyl-4-cyclohexylmethyl-2,2-dimethyl-5-(2-methyl-2-buten-4-yl)-1,3-oxazolidine Triphenylphosphine (13.5 g) and isopropyl iodide (8.5 g) were heated to 180° C. and stirred in an autoclave. The solid obtained 24 hours later was recrystallized from methanol-diethyl ether to give 22 g of yellow-brown crystals. A solution of the crystals (7.98 g) in dry tetrahydrofuran (50 ml) was cooled to 0° C. and n-butyllithium (1.6 M hexane solution, 9.5 ml) was dropwise added. After stirring at 0° C. for 20 minutes, a solution of the compound (2.3 g) obtained in Production Example 3 in dry tetrahydrofuran (50 ml) was dropwise added. After stirring the mixture was at 0° C. for 2 hours, a saturated aqueous solution (80 ml) of NaHCO$_3$ was added, and the mixture was extracted twice with ethyl acetate. The organic layer was sequentially washed with a saturated aqueous solution of NaHCO$_3$, 0.1 N hydrochloric acid, water and saturated brine, and dried over MgSO$_4$. The solvent was distilled away under reduced pressure. The residue was purified by silica gel column chromatography (eluted with AcOEt/Hex=5/95 v/v) to give 1.29 g of a colorless, oily title compound (see Table 1).

Production Example 5
(4S,5S)-5-allyl-4-cyclohexylmethyl-1,3-oxazolidin-2-one

A suspension of sodium hydride (60% in oil, 121 mg) was washed with hexane, suspended in DMF (7 ml) and ice-cooled. A solution of the compound (500 mg) obtained in Production Example 1 in DMF (3 ml) was dropwise added and the mixture was stirred for 30 minutes under ice-cooling. The mixture was added to ice an aqueous solution of 0.1M citric acid (30 ml) and extracted with ethyl acetate (25 ml×2). The organic layer was washed with a saturated aqueous solution of NaHCO$_3$ and saturated brine, and dried over MgSO$_4$. The solvent was distilled away under reduced pressure. The residue was purified by silica gel column chromatography (eluted with AcOEt/Hex=2/8→3/7 v/v) to give 174 mg of colorless, oily title compound (see Table 2).

Production Example 6
(4S,5S)-5-benzyloxycarbonylamino-4-benzyloxylmethoxy-6-cyclohexyl-1-hexene The compound (500 mg) obtained in Production Example 1 was dissolved in dichloromethane (5 ml), and N,N-diisopropylethyl-amine (0.315 ml) and benzyloxymethyl chloride (0.252 ml) were added. After stirring at room temperature for 2.5 hours, N,N-diisopropylethylamine (0.315 ml) and benzyloxymethyl chloride (0.252 ml) were added, and the mixture was stirred at room temperature for 1 hour. Ethyl acetate (20 ml) was added to the reaction mixture, washed with an aqueous solution of 0.1M citric acid (×2), a saturated aqueous solution of NaHCO$_3$ and saturated brine, and dried over MgSO$_4$. The solvent was distilled away under reduced pressure. The residue was purified by silica gel column chromatography (eluted with AcOEt/Hex=1/9 v/v) to give 566 mg of a colorless, oily title compound (see Table 2).

Production Example 7
3-methyl-2,3-bis(trimethylsilyloxy)-1-butene

A solution of 1.6M n-butyllithium/n-hexane solution (100 ml) was dropwise added to a solution of diisopropylamine (22.4 ml) in dry tetrahydrofuran (50 ml) at −10° C., and the mixture was stirred for 1 hour. A solution of 3-hydroxy-3-methyl-2-butanone (8 ml) in dry tetrahydrofuran (50 ml) was dropwise added at −10° C. and the mixture was stirred for 1 hour. Then, trimethylchlorosilane (20.4 ml) was dropwise added at −10° C. After stirring at 4° C overnight, the reaction mixture was filtered with celite and the solid was washed with diethyl ether (500 ml). The combined filtrate was washed with 1N hydrochloric acid (150 ml×2) and a saturated aqueous solution of NaHCO$_3$ (150 ml×2), and dried over MgSO$_4$. The solvent was distilled away under reduced pressure. The residue was distilled under reduced pressure to give 16 g of the title compound (bp=85°–90° C./20 mmHg) as colorless liquid (see Table 2).

Production Example 8
(5S, 6S)-6-benzyloxycarbonylamino-7-cyclohexyl-5-hydroxy-2-methyl-2-trimethylsilyloxy-3-heptanone Molecular sieves 4A was added to a solution of N-benzyloxycarbonyl-L-cyclohexylalaninal (57 g) in dichloromethane (250 ml), and the mixture was stirred at room temperature for 30 minutes, followed by cooling to −20° C. A solution of boron trifluoride-diethyl ether complex (23 ml) in dichloromethane (70 ml) and then a solution of the compound (62 g) obtained in Production Example 7 in dichloromethane (130 ml) were dropwise added and the mixture was stirred at −20° C. for 30 minutes. The reaction mixture was slowly added to ice (200 g)—a saturated aqueous solution (300 ml) of NaHCO$_3$ and stirred. The organic layer was sequentially washed with a saturated aqueous solution (300 ml) of NaHCO$_3$ and saturated brine (300 ml), and dried over MgSO$_4$. The solvent was distilled away under reduced pressure to give a crude product containing the title compound as a main component. A part was purified by silica gel column chromatography to give a colorless, oily title compound (see Table 2).

Production Example 9
(5S,6S)-6-benzyloxycarbonylamino-7-cyclohexyl-2,5-dihydroxy-2-methyl-3-heptanone The crude product obtained in Production Example 8 was dissolved in methanol (675 ml) and 0.1 N hydrochloric acid (75 ml) was added. The mixture was stirred at room temperature for 15 minutes. An aqueous solution of 1N NaOH was added for neutralization and methanol was distilled away under reduced pressure. Water (300 ml) was added to the residual aqueous layer and the mixture was extracted with chloroform (600 ml). The organic layer was sequentially washed with a saturated aqueous solution (300 ml) of NaHCO$_3$ and saturated brine (300 ml), and dried over MgSO$_4$. The solvent was distilled away under reduced pressure to give 61 g of a crude product containing the title compound as a main component (see Table 3).

Production Example 10
(4S,5S)-3-benzyloxycarbonyl-4-cyclohexylmethyl-5-(3-hydroxy-3-methyl-2-oxobutyl)-2,2-dimethyl-1,3-oxazolidine A crude product (59 g) containing the title compound as a main component was obtained from the crude product (57 g) obtained in Production Example 9 by the same method as in Production Example 2 (see Table 3).

Production Example 11
(4S,5S)-3-benzyloxycarbonyl-4-cyclohexylmethyl-5-[(2S)-2,3-dihydroxy-3-methylbutyl]-2,2-dimethyl-1,3-oxazolidine <Method A>

Osmium tetraoxide (49 mM tert-butanol solution, 3 ml) and N-methylmorpholine-N-oxide (1.32 g) were added to a solution of the compound (1.5 g) obtained in Production Example 4 in dry tetrahydrofuran (50 ml). After stirring at room temperature for 4 hours, saturated brine (50 ml) was added to the reaction mixture and the mixture was extracted with ethyl acetate (70 ml×2). The organic layer was washed twice with an aqueous solution of 10% Na$_2$SO$_3$ and once with a saturated aqueous solution of NH$_4$Cl, and dried over MgSO$_4$. The solvent was distilled away under reduced pressure. The residue was recrystallized from ethyl acetate-hexane to give 485 mg of the title compound as white crystals (see Table 3). <Method B>

A solution of the crude product (59 g) obtained in Production Example 10 in methanol (300 ml) was ice-cooled and sodium borohydride (15.4 g) was added. The mixture was stirred under ice-cooling for 1 hour and added with water (150 ml). Methanol was distilled away under reduced pressure and the mixture was extracted with chloroform (300 ml×2). The organic layer was sequentially washed with an aqueous solution of 10% citric acid (300 ml), a saturated aqueous solution of NaHCO₃ (300 ml) and saturated brine (300 ml), and dried over MgSO₄. The solvent was distilled away under reduced pressure. The oily residue was recrystallized from hexane and the resulting crystals were recrystallized from ethyl acetate-hexane to give 7.45 g of the title compound as white crystals (see Table 3).

Production Example 12
(4S,5S)-3-benzyloxycarbonyl-4-cyclohexylmethyl-5-[(2R)-2, 3-dihydroxy-3-methylbutyl]-2,2-dimethyl-1,3-oxazolidine The title compound (340 mg) was obtained by concentration of the recrystallization mother liquor of <Method A> of Producation Example 10 and purification of the residue by silica gel column chromatography (eluted with CHCl₃) (see Table 3).

Production Example 13
(4S,5S)-3-benzyloxycarbonyl-4-cyclohexylmethyl-5-[(5S)-4,4-dimethyl-1,3-dioxolan-5-yl] methyl-2,2-dimethyl-1,3-oxazolidine A suspension of sodium hydride (60% in oil, 2.6 g) was washed with hexane, and a solution of the compound (8 g) obtained in Production Example 11 in DMF (120 ml) was dropwise added under ice-cooling. After stirring under ice-cooling for 1 hour, dibromomethane (4.5 ml) was dropwise added. The mixture was stirred at room temperature for 1.5 hours. The reaction mixture was added to an aqueous solution of 10% citric acid under ice-cooling and stirred and extracted with ethyl acetate (300 ml×2). The organic layer was washed with a saturated aqueous solution (300 ml) of NaHCO₃ and saturated brine (300 ml), and dried over MgSO₄. The solvent was distilled away under reduced pressure to give 9.2 g of a pale-yellow, oily title compound (see Table 4).

Production Example 14
(4S,5S)-3-benzyloxycarbonyl-4-cyclohexylmethyl-5-[(5R)-4,4-dimethyl-1,3-dioxolan-5-yl]methyl-2,2-dimethyl-1,3-oxazolidine The title compound (170 mg) was obtained from the compound (340 mg) obtained in Production Example 12 by the same method as in Production Example 13 (see Table 4).

Production Example 15
(4S)-4-[(2S,3S)-3-benzyloxycarbonylamino-4-cyclohexyl-2-hydroxybutyl]-5,5-dimethyl-1,3-dioxolane p-Toluenesulfonic acid monohydrate (0.64 g) was added to a solution of the compound (9.2 g) obtained in Production Example 13 in methanol (100 ml) and the mixture was stirred at room temperature for 5 hours. The reaction mixture was added to a saturated aqueous solution (200 ml) of NaHCO₃ under ice-cooling and stirred. The resulting solid was filtered and washed with methanol. Methanol was distilled away from the filtrate under reduced pressure and the residual aqueous layer was extracted with chloroform (200 ml×3). The organic layer was washed with saturated brine (200 ml), and dried over MgSO₄. The solvent was distilled away under reduced pressure. The residue was recrystallized from ethyl acetate-hexane to give 4.01 g of the title compound as white crystals (see Table 4).

Production Example 16
(4R)-4-[(2S,3S)-3-benzyloxycarbonylamino-4-cyclohexyl-2-hydroxybutyl]-5,5-dimethyl-1,3-dioxolane The title compound (158 mg) was obtained as a colorless oil from the compound (170 mg) obtained in Production Example 14 by the same method as in Production Example 15 (see Table 4).

Production Example 17
3-methoxymethoxy-3-methyl-2-butanone

A solution of N,N-diisopropylethylamine (131 ml) and chloromethyl methyl ether (57 ml) in dichloromethane (50 ml) was added under ice-cooling to a solution of 3-hydroxy-3-methyl-2-butanone (52.6 ml) in dichloromethane (450 ml) and the mixture was stirred at room temperature overnight. The reaction mixture was washed with an aqueous solution (250 ml×2) of 10% citric acid, a saturated aqueous solution (200 ml) of NaHCO₃ and saturated brine (200 ml), and dried over MgSO₄. The solvent was distilled away under reduced pressure. The residue was distilled under atmospheric pressure to give 53.6 g of the title compound (bp=155°–165° C.) as a colorless liquid (see Table 5).

Production Example 18
3-methyl-3-methoxymethoxy-2-trimethylsilyloxy-1-butene A solution of 1.6M n-butyllithium/n-hexane solution (138 ml) was dropwise added to a solution of diisopropylamine (31 ml) in dry tetrahydrofuran (150 ml) at −10° C. and the mixture was stirred for 50 minutes. A solution of the compound (29.2 g) obtained in Production Example 17 in dry tetrahydrofuran (150 ml) was dropwise added at −10° C. and the mixture was stirred for 50 minutes. Then, trimethylchlorosilane (28 ml) was dropwise added at −10° C. The mixture was stirred at 4° C. overnight and the reaction mixture was filtered with celite and the solid was washed with diethyl ether (250 ml). The combined filtrate was washed with 0.01N hydrochloric acid (200 ml×2), a saturated aqueous solution (200 ml×2) of NaHCO₃ and saturated brine (200 ml), and dried over MgSO₄. The solvent was distilled away under reduced pressure. The residue was distilled under reduced pressure to give 34.4 g of the title compound (bp=85°–90° C./20 mmHg) as a colorless liquid (see Table 5).

Production Example 19
(5S, 6S)-6-benzyloxycarbonylamino-7-cyclohexyl-5-hydroxy-2-methyl-2-methoxymethoxy-3-heptanone Molecular sieves 4A was added to a solution of N-benzyloxycarbonyl-L-cyclohexylalaninal (18 g) in dichloromethane (180 ml), and the mixture was stirred at room temperature for 1 hour, followed by cooling to −20° C. A solution of boron trifluoride-diethyl ether complex (8.41 ml) in dichloromethane (30 ml) and then a solution of the compound (16.3 g) obtained in Production Example 18 in dichloromethane (60 ml) were dropwise added and the mixture was stirred at −20° C. for 20 minutes. The reaction mixture was slowly added to ice-a saturated aqueous solution (200 ml) of NaHCO₃ and stirred. The organic layer was sequentially washed with a saturated aqueous solution (200 ml) of NaHCO₃ and saturated brine (200 ml), and dried over MgSO₄. The solvent was distilled away under reduced pressure to give a crude product (29.5 g) containing the title compound as a main component, as a yellow oil. A part (1.3 g) of the crude product was purified by silica gel column chromatography to give 0.68 g of a colorless, oily title compound (see Table 5).

Production Example 20
(2S,3S,5S)-2-benzyloxycarbonylamino-1-cyclohexyl-6-methyl-6-methoxymethoxy-3,5-heptanediol Tetramethylammonium borohydride (13 g) was added to a mixed solvent of acetic acid (150 ml) and acetonitrile (150 ml) under ice-cooling and the mixture was stirred under ice-cooling for 1 hour. A solution of the crude product (28 g) obtained in Production Example 19 in acetic acid (100 ml)-acetonitrile (100 ml) was dropwise added under ice-cooling and the mixture was stirred at room temperature for 2 hours. The reaction mixture was slowly added to ice-a saturated aqueous solution (500 ml) of $NaHCO_3$ and extracted with dichloromethane (500 ml). The organic layer was sequentially washed with 1N NaOH (400 ml), a saturated aqueous solution (400 ml×2) of $NaHCO_3$ and saturated brine (200 ml), and dried over $MgSO_4$. The solvent was distilled away under reduced pressure to give a crude product (25.7 g) containing the title compound as a main component, as a yellow oil. The crude product (10 g) was purified by silica gel column chromatography (eluted with AcOEt/Hex=55/45) to give 4.87 g of a colorless, oily title compound (see Table 5).

Production Example 21

(4S,5S)-4-cyclohexylmethyl-5-[(2S)-2-hydroxy-3-methyl-3-methoxymethoxybutyl]-1,3-oxazolidin-2-one 2N NaOH (34.3 ml) was added to a solution of the crude product (10 g) obtained in Production Example 20 in methanol (100 ml) and the mixture was stirred at room temperature for 3 hours. Methanol was distilled away under reduced pressure and water (150 ml) was added to the residual aqueous layer, and the mixture was extracted with chloroform (200 ml×2). The organic layer was washed with a saturated aqueous solution (200 ml×2) of $NaHCO_3$ and dried over $MgSO_4$. The solvent was distilled away under reduced pressure. The residue was recrystallized from ethyl acetate-hexane to give 3.2 g of the title compound as white crystals (see Table 6).

Production Example 22

(4S,5S)-4-cyclohexylmethyl-5-[(5S)-4,4-dimethyl-1,3-dioxolan-5-yl]methyl-1,3-oxazolidin-2-one A solution of boron trifluoride-diethyl ether complex (0.038 ml) in dichloromethane (0.5 ml) was added to a solution of the compound (100 mg) obtained in Production Example 21 in dichloromethane (2 ml) under ice-cooling and the mixture was stirred under ice-cooling for 10 minutes. Dichloromethane (10 ml) was added to the reaction mixture and the mixture was washed twice with a saturated aqueous solution of $NaHCO_3$ and once with saturated brine, and dried over $MgSO_4$. The solvent was distilled away under reduced pressure. The residue was purified by preparative thin layer chromatography to give 45 mg of the title compound as a white solid (see Table 6).

Production Example 23

(4S,5S)-4-cyclohexylmethyl-5-[(5S)-4,4-dimethyl-1,3-dioxolan-5-yl]methyl-3-methoxymethyl-1,3-oxazolidin-2-one Lithium bromide (0.36 g), p-toluenesulfonic acid monohydrate (0.36 g) and dimethoxymethane (1.9 ml) were sequentially added to a solution of the compound (1.38 g) obtained in Production Example 21 in DMF (14 ml) and the mixture was refluxed under heating for 3 hours. A saturated aqueous solution (40 ml) of $NaHCO_3$ was added to the reaction mixture under ice-cooling and extracted with ethyl acetate (40 ml×2). The organic layer was washed with a saturated aqueous solution (40 ml×2) of $NaHCO_3$ and dried over $MgSO_4$. The solvent was distilled away under reduced pressure to give 1.43 g of the title compound as a pale-yellow solid (see Table 6).

Production Example 24

(4S)-4-[(2S,3S)-3-amino-4-cyclohexyl-2-hydroxybutyl]-5,5-dimethyl-1,3-dioxolane <Method A>

10% Palladium on activated carbon (0.3 g) was added to a solution of the compound (4.18 g) obtained in Production Example 15 in methanol (50 ml) and the mixture was hydrogenated under atmospheric pressure for 3 hours. The catalyst was filtered away and the solvent was distilled away under reduced pressure to give 3.04 g of the title compound as a colorless oil (see Table 6). <Method B>

The compound (1.22 g) obtained in Production Example 23 was dissolved in a mixed solvent of water (12 ml) and 1,4-dioxane (12 ml) and barium hydroxide 8 hydrate (11.3 g) was added. The mixture was refluxed under heating for 2 days. The temperature of the mixture was cooled to room temerature and water (15 ml) was added. The mixture was extracted with dichloromethane (40 ml×2). The organic layer was dried over $MgSO_4$ and the solvent was distilled away under reduced pressure to give 0.90 g of the title compound as a red oil (see Table 6).

Production Example 25

(4R)-4-[(2S,3S)-3-amino-4-cyclohexyl-2-hydroxybutyl]-5,5-dimethyl-1,3-dioxolane

The title compound (103 mg) was obtained as a colorless oil from the compound (158 mg) obtained in Production Example 16 by the same method as in Production Example 24 <Method A> (see Table 7).

Production Example 26

(4S,5S)-4-cyclohexylmethyl-5-[(2S)-2,3-dihydroxy-3-methylbutyl ]-1,3-oxazolidin-2-one Conc. hydrochloric acid (2 ml) was dropwise added to a solution of the compound (1 g) obtained in Production Example 21 in methanol (20 ml) and the mixture was stirred at room temperature for 1 hour. A saturated aqueous solution of $NaHCO_3$ was added to the reaction mixture for neutralization and the mixture was extracted with chloroform. The organic layer was washed with a saturated aqueous solution of $NaHCO_3$ and dried over $MgSO_4$. The solvent was distilled away under reduced pressure to give 866 mg of the title compound as a white solid (see Table 7).

Production Example 27

(4S,5S)-4-cyclohexylmethyl-5-[(5S)-2,2,4,4-tetramethyl-1,3-dioxolan-5-yl]methyl-1,3-oxazolidin-2-one PPTS (176 mg) and 2-methoxypropene (0.7 ml) were added to a solution of the compound (400 mg) obtained in Production Example 26 in DMF (4 ml) and the mixture was stirred at room temperature for 1 hour. A saturated aqueous solution (20 ml) of $NaHCO_3$ was added to the reaction mixture and stirred. Water was added and the mixture was extracted twice with chloroform. The organic layer was washed with a saturated aqueous solution of $NaHCO_3$ and dried over $MgSO_4$. The solvent was distilled away under reduced pressure to give 447 mg of the title compound as a white solid (see Table 7).

Production Example 28

(4S,5S)-4-cyclohexylmethyl-5-[(5S)-4,4-dimethyl-2-phenyl-1,3-dioxolan-5-yl]methyl-1,3-oxazolidin-2-one Lithium bromide (125 mg), p-toluenesulfonic acid monohydrate (50 mg) and benzaldehyde dimethyl acetal (1.1 ml) were added to a solution of the compound (410 mg) obtained in Production Example 26 in DMF (4 ml) and the mixture was stirred at room temperature for 1.5 hours. A saturated aqueous solution of $NaHCO_3$ was added to the reaction mixture and the mixture was extracted with chloroform (40 ml×2). The organic layer was washed with a saturated aqueous solution of $NaHCO_3$ and dried over $MgSO_4$. The solvent was distilled away under reduced pressure to give 634 mg of the title compound as a white solid (see Table 7).

Production Example 29
(4S)-4-[(2S,3S)-3-amino-4-cyclohexyl-2-hydroxybutyl ]-2,2,5,5-tetramethyl-1,3-dioxolane 2N NaOH (2.05 ml) was added to a solution of the compound (446 mg) obtained in Production Example 27 in ethanol (20 ml) and the mixture was refluxed under heating overnight. The reaction mixture was cooled to room temerature and water was added. The mixture was extracted with chloroform. The organic layer was dried over MgSO₄ and the solvent was distilled away under reduced pressure to give 413 mg of the title compound as a a yellow oil (see Table 8).

Production Example 30
(4S)-4-[(2S,3S)-3-amino-4-cyclohexyl-2-hydroxybutyl ]-5,5-dimethyl-2-phenyl-1,3-dioxolane 2N NaOH (3 ml) was added to a solution of the compound (634 mg) obtained in Production Example 28 in ethanol (20 ml) and the mixture was refluxed under heating overnight. The reaction mixture was cooled to room temerature and water was added. The mixture was extracted with chloroform. The organic layer was dried over MgSO₄ and the solvent was distilled away under reduced pressure to give 450 mg of the title compound as a yellow oil (see Table 8).

Production Example 31
N-piperidinocarbonyl-L-phenylalanine benzyl ester

Triethylamine (10.9 g) and piperidinocarbonyl chloride [16 g, see Synthetic Communications, vol. 17, 1887–1892 (1987)] were sequentially added to a solution of L-phenylalanine benzyl ester (39.6 g) in dichloromethane under ice-cooling and the mixture was stirred at room temperature for 24 hours. Water (250 ml) was added to the reaction mixture and the organic layer was separated. The aqueous layer was extracted with dichloromethane (250 ml). The combined organic layer was washed with 0.1N hydrochloric acid (250 ml×2) and a saturated aqueous solution (250 ml) of NaHCO₃, and dried over MgSO₄. The solvent was distilled away under reduced pressure. The residue was recrystallized from ethyl acetate-hexane to give 29.3 g of the title compound as white crystals (see Table 8).

Production Example 32
N-piperidinocarbonyl-L-phenylalanine

2N NaOH (40.9 ml) was added to a solution of the compound (20 g) obtained in Production Example 31 in methanol (160 ml) and the mixture was stirred at room temperature for 30 minutes. Methanol was distilled away under reduced pressure and water (200 ml) was added. The mixture was washed with dichloromethane (200 ml×4). 6N Hydrochloric acid was added to the aqueous layer to adjust the pH to 1 and the mixture was extracted with dichloromethane (150 ml×3). The organic layer was washed with saturated brine (200 ml) and dried over MgSO₄. The solvent was distilled away under reduced pressure to give 14.8 g of the title compound as a white solid (see Table 8).

Production Example 33
Nα-methyl-Nα-(N-piperidinocarbonyl-L-phenylalanyl)-L-histidine methyl ester 1-Hydroxybenzotriazole monohydrate (1.91 g) and N,N'-dicyclohexylcarbodiimide (2.48 g) were added to a solution of the compound (3.0 g) obtained in Production Example 32 in DMF (20 ml) under ice-cooling, and the mixture was stirred under ice-cooling for 1.5 hours. Then, a solution of Nα-methyl-L-histidine methyl ester (2.0 g, see Japanese Patent Unexamined Publication No. 204860/1991) in DMF (20 ml) was added and the mixture was stirred under ice-cooling for 0.5 hour and at room temperature for 2.5 days. The reaction mixture was filtered and the filtrate was concentrated under reduced pressure. A mixed solution (50 ml) of methanol/water/acetic acid (94/3/3 v/v/v) was added and the mixture was heated at 60° C. for 40 minutes. The reaction mixture was concentrated under reduced pressure, added with a saturated aqueous solution of NaHCO₃ and extracted with chloroform. The organic layer was washed with a saturated aqueous solution of NaHCO₃ and dried over MgSO₄. The solvent was distilled away under reduced pressure. The residue was purified by silica gel column chromatography (eluted with CHCl₃/MeOH=97/3 v/v) to give 2.62 g of the title compound as a white solid (see Table 9).

Production Example 34
Nα-methyl-Nα-(N-piperidinocarbonyl-L-phenylalanyl)-L-histidine hydrazide Hydrazine monohydrate (2.88 ml) was added to a solution of the compound (2.62 g) obtained in Production Example 33 in methanol (30 ml), and the mixture was stirred at room temperature for 7.5 hours. The solvent was distilled away under reduced pressure. Water (30 ml) was added and powdery potassium carbonate was added to adjust the pH to 11 and the mixture was extracted with chloroform (50 ml). The organic layer was dried over MgSO₄ and the solvent was distilled away under reduced pressure to give 2.42 g of the title compound as a white solid (see Table 9).

Production Example 35
(2S)-3-phenyl-2-piperidinocarbonyloxypropionic acid benzyl ester Active charcoal (30 mg) and trichloromethyl chloroformate (1.06 ml) were added to a solution of (2S)-2-hydroxy-3-phenylpropionic acid benzyl ester (3.0 g) in dry tetrahydrofuran (10 ml) and the mixture was stirred at room temperature overnight. A solution of piperidine (3.47 ml) and triethylamine (4.89 ml) in dichloromethane (10 ml) was added and the mixture was stirred at room temperature for 30 minutes. The reaction mixture was filtered and the filtrate was concentrated under reduced pressure. Ethyl acetate (50 ml) was added and the mixture was washed with 0.01N hydrochloric acid, a saturated aqueous solution of NaHCO₃ and saturated brine. The organic layer was dried over MgSO₄ and the solvent was distilled away under reduced pressure. The residue was purified by silica gel column chromatography (eluted with AcOEt/Hex=1/9→2/8 v/v) to give 4.71 g of the title compound as a colorless oil (see Table 9).

Production Example 36
(2S)-3-phenyl-2-piperidinocarbonyloxypropionic acid

10% Palladium on activated carbon (0.5 g) was added to a solution of the compound (4.71 g) obtained in Production Example 35 in methanol (50 ml) and the mixture was hydrogenated under atmospheric pressure for 2 hours. The catalyst was filtered away and the solvent was distilled away under reduced pressure to give 2.90 g of the title compound as a colorless oil (see Table 9).

Production Example 37
(4S)-4-[(2S,3S)-3-(Nα-benzyloxycarbonyl-L-histidyl)amino-4-cyclohexyl-2-hydroxybutyl]-5,5-dimethyl-1,3-dioxolane The title compound (790 mg) was obtained as a white solid from Nα-benzyloxycarbonyl-L-histidine (523 mg) and the compound (490 mg) obtained in Production Example 24 by the same method as in Production Example 33 (see Table 10).

Production Example 38

(4S)-4-[(2S,3S)-4-cyclohexyl-3-(L-histidyl) amino-2-hydroxybutyl]-5,5-dimethyl-1,3-dioxolane The title compound (529 mg) was obtained as a white solid from the compound (742 mg) obtained in Production Example 37 by the same method as in Production Example 24 <Method A> (see Table 10).

Production Example 39

(4S)-4-[(2S,3S)-3-(Nα-benzyloxycarbonyl-Nα-methyl-L-histidyl)-amino-4-cyclohexyl-2-hydroxybutil]-5,5-dimethyl-1,3-dioxolane A solution of Nα-benzyloxycarbonyl-Nα-methyl-L-histidine hydrazide (1.72 g, see Japanese Patent Unexamined Publication No. 204860/1991) in DMF (12 ml) was cooled to −30° C. and a solution (4.07 ml) of 4N HCl-dioxane and isopentyl nitrite (0.873 ml) were added and the mixture was stirred at −30° C. for 1 hour. The reaction mixture was cooled to −50° C. and triethylamine was added for neutralization and then, a solution of the compound (1.47 g) obtained in Production Example 24 in DMF (20 ml) was added. After stirring overnight at 4° C., the reaction mixture was filtered and the solvent in the filtrate was distilled away under reduced pressure. The residue was dissolved in ethyl acetate (50 ml), washed with a saturated aqueous solution (50 ml×2) of NaHCO$_3$ and dried over MgSO$_4$. The solvent was distilled away under reduced pressure. The residue was purified by silica gel column chromatography (eluted with CHCl$_3$/MeOH=97/3→96/4 v/v) to give 1.43 g of the title compound as a white solid (see Table 10).

Production Example 40

(4S)-4-[(2S,3S)-4-cyclohexyl-2-hydroxy-3-(Nα-methyl-L-histidyl) aminobutyl]-5,5-dimethyl-1,3-dioxolane The title compound (1.03 g) was obtained as a white solid from the compound (1.43 g) obtained in Production Example 39 by the same method as in Production Example 24 <Method A> (see Table 10).

Production Example 41

N-(4-methylpiperidino)carbonyl-L-phenylalanine benzyl ester

Trichloromethyl chloroformate (0.44 ml) was added to a solution of triethylamine (1.48 g) in dry tetrahydrofuran (15 ml) under ice-cooling and a solution of L-phenylalanine benzyl ester (1.27 g) in dry tetrahydrofuran (7.5 ml) was dropwise added slowly. Then, a solution of 4-methylpiperidine (1.15 ml) in dry tetrahydrofuran (7.5 ml) was dropwise added. The mixture was stirred at room temperature for 1 hour. The resulting salt was collected by filtration and washed with ethyl acetate (70 ml). The combined filtrate was washed twice with 0.1N hydrochloric acid, twice with a saturated aqueous solution of NaHCO$_3$ and saturated brine, and dried over MgSO$_4$. The solvent was distilled away under reduced pressure. The residue was purified by silica gel column chromatography (eluted with AcOEt/Hex=4/6 v/v) to give 1.86 g of the title compound as a colorless oil (see Table 11).

Production Example 42

N-(4-methylpiperidino)carbonyl-L-phenylalanine

The title compound (0.975 g) was obtained as a white solid from the compound (1.86 g) obtained in Production Example 41 by the same method as in Production Example 36 (see Table 11).

Production Example 43

N-(diethylamino)carbonyl-L-phenylalanine benzyl ester

The title compound (2.44 g) was obtained with the use of diethylaminocarbonyl chloride (6.05 g) and L-phenylalanine benzyl ester (9.90 g) by the same method as in Production Example 31 (see Table 11).

Production Example 44

N-(diethylamino)carbonyl-L-phenylalanine

The title compound (1.76 g) was obtained as a white solid from the compound (2.44 g) obtained in Production Example 43 by the same method as in Production Example 36 (see Table 11).

Production Example 45

N-cyclohexylcarbonyl-L-phenylalanine benzyl ester

The title compound (3.15 g) was obtained with the use of cyclohexylcarbonyl chloride (1.76 g) and L-phenylalanine benzyl ester (3.10 g) by the same method as in Production Example 31 (see Table 12).

Production Example 46

N-cyclohexylcarbonyl-L-phenylalanine

The title compound (2.46 g) was obtained as a white solid from the compound (3.15 g) obtained in Production Example 45 by the same method as in Production Example 36 (see Table 12).

Production Example 47

N-[(2S)-2-(4-methylpiperazinyl)carbonyloxy-3-phenylpropionyl]-S-methyl-L-cysteine methyl ester The title compound (590 mg) was obtained as a white solid with the use of (2S)-2-(4-methylpiperazinyl) carbonyloxy-3-phenylpropionic acid (500 mg) and S-methyl-L-cysteine methyl ester (293 mg) by the same method as in Production Example 33 (see Table 12).

Production Example 48

N-[(2S)-2-(4-methylpiperazinyl)carbonyloxy-3-phenylpropionyl]-S-methyl-L-cysteine The title compound was obtained from the compound (470 mg) obtained in Production Example 47 by the same method as in Production Example 32 (see Table 12).

Example 1

(4S)-4-[(2S,3S)-4-cyclohexyl-2-hydroxy-3-[[Nα-methyl-N α-(N-piperidinocarbonyl-L-phenylalanyl)-L-histidyl] amino]butyl]-5,5-dimethyl-1,3-dioxolane The compound (326 mg) obtained in Production Example 34 was dissolved in DMF (5 ml) and a solution (0.608 ml) of 4N HCl-dioxane and isopentyl nitrite (0.120 ml) were added at −30° C. After stirring at −30 °C. for 1 hour, the mixture was cooled to −70° C. and triethylamine was added for neutralization. A solution of the compound (200 mg) obtained in Production Example 24 in DMF (5 ml) was added at −70° C. and the mixture was stirred at 4° C. overnight. The solvent was distilled away under reduced pressure. The residue was dissolved in ethyl acetate (30 ml) and washed with a saturated aqueous solution (30 ml×2) of NaHCO$_3$, and dried over MgSO$_4$. The solvent was distilled away under reduced pressure. The residue was purified by silica gel column chromatography (eluted with CHCl$_3$/MeOH=95/5 v/v) to give 362 mg of the title compound as a white solid (see Table 13).

Example 2

(4R)-4-[(2S,3S)-4-cyclohexyl-2-hydroxy-3-[[Nα-methyl-N α-(N-piperidinocarbonyl-L-phenylalanyl)-L-histidyl] amino]butyl]-5,5-dimethyl-1,3-dioxolane The title compound (65 mg) was obtained as a white solid from the compound (50 mg) obtained in Production Example 25 by the same method as in Example 1 (see Table 13).

Example 3
(4S)-4-[(2S,3S)-4-cyclohexyl-2-hydroxy-3-[[Nα-[(2S)-3-phenyl-2-piperidinocarbonyloxypropionyl]-L-histidyl]amino]butyl]-5,5-dimethyl-1,3-dioxolane 1-Hydroxybenzotriazole monohydrate (112 mg) and N,N'-dicyclohexylcarbodiimide (145 mg) were added to a solution of the compound (177 mg) obtained in Production Example 36 in DMF (3 ml) under ice-cooling, and the mixture was stirred under ice-cooling for 1 hour. Then, the compound (260 mg) obtained in Production Example 38 was added and the mixture was stirred under ice-cooling for 0.5 hour and at room temperature overnight. The reaction mixture was filtered and the filtrate was concentrated under reduced pressure. A mixed solution (6 ml) of methanol/water/acetic acid (94/3/3 v/v/v) was added and the mixture was heated at 60° C. for 40 minutes. The reaction mixture was concentrated under reduced pressure, added with a saturated aqueous solution of NaHCO₃ and extracted with ethyl acetate. The organic layer was washed with a saturated aqueous solution of NaHCO₃ and dried over MgSO₄. The solvent was distilled away under reduced pressure. The residue was purified by silica gel column chromatography (eluted with CHCl₃/MeOH=97/3 v/v) to give 287 mg of the title compound as a white solid (see Table 13).

Example 4
(4S)-4-[(2S,3S)-4-cyclohexyl-2-hydroxy-3-[[N α-(N-piperidino-carbonyl-L-phenylalanyl)-L-histidyl]amino]butyl ]-5,5-dimethyl-1,3-dioxolane The title compound (220 mg) was obtained as a pale-yellow solid from the compound (150 mg) obtained in Production Example 32 and the compound (220 mg) obtained in Production Example 38 by the same method as in Example 3 (see Table 13).

Example 5
(4S)-4-[(2S,3S)-4-cyclohexyl-2-hydroxy-3-[[S-methyl-N-[(2S)-3-phenyl-2-(4-methylpiperazinyl)carbonyloxypropionyl ]-L-cysteinyl]amino]butyl]-5,5-dimethyl-1,3-dioxolane The title compound (79 mg) was obtained as a pale-yellow solid from the compound (455 mg) obtained in Production Example 48 and the compound (200 mg) obtained in Production Example 24 by the same method as in Example 3 (see Table 14).

Example 6
(4S)-4-[(2S,3S)-4-cyclohexyl-2-hydroxy-3-[[Nα-methyl-N α-(N-piperidinosulfonyl-L-phenylalanyl)-L-histidyl]amino]butyl ]-5,5-dimethyl-1,3-dioxolane The title compound (169 mg) was obtained as a white solid from N-piperidinosulfonyl-L-phenylalanine (182 mg, see Japanese Patent Unexamined Publication No. 86870/1991) and the compound (190 mg) obtained in Production Example 40 by the same method as in Example 3 (see Table 14).

Example 7
(4S)-4-[(2S,3S)-4-cyclohexyl-2-hydroxy-3-[N α-(indole-2-carbonyl)-L-histidyl]amino]butyl]-5,5-dimethyl-1,3-dioxolane The title compound (192 mg) was obtained as a pale-yellow solid from indole-2-carboxylic acid (87 mg) and the compound (200 mg) obtained in Production Example 38 by the same method as in Example 3 (see Table 14).

Example 8
(4S)-4-[(2S,3S)-4-cyclohexyl-2-hydroxy-3-[[N α-methyl-Nα-(N-cyclohexylcarbonyl-L-phenylalanyl)-L-histidyl]amino]butyl]-5,5-dimethyl-1,3-dioxolane The title compound (25 mg) was obtained as a white solid from the compound (33 mg) obtained in Production Example 46 and the compound (50 mg) obtained in Production Example 40 by the same method as in Example 3 (see Table 14).

Example 9
(4S)-4-[(2S,3S)-4-cyclohexyl-2-hydroxy-3-[[Nα-methyl-N α-[N-(4-methylpiperidino)carbonyl-L-phenylalanyl]-L-histidyl ]-amino]butyl]-5,5-dimethyl-1,3-dioxolane The title compound (165 mg) was obtained as a white solid from the compound (142 mg) obtained in Production Example 42 and the compound (200 mg) obtained in Production Example 40 by the same method as in Example 3 (see Table 15).

Example 10
(4S)-4-[(2S,3S)-4-cyclohexyl-2-hydroxy-3-[[Nα-methyl-N α-[N-(diethylamino)carbonyl-L-phenylalanyl]-L-histidyl]amino]butyl]-5,5-dimethyl-1,3-dioxolane The title compound (222 mg) was obtained as a white solid from the compound (125 mg) obtained in Production Example 44 and the compound (200 mg) obtained in Production Example 40 by the same method as in Example 3 (see Table 15).

Example 11
(4S)-4-[(2S,3S)-4-cyclohexyl-2-hydroxy-3-[[Nα-methyl-N α-(N-piperidinocarbonyl-L-phenylalanyl)-L-histidyl]amino]butyl]-2,2,5,5-tetramethyl-1,3-dioxolane The title compound (720 mg) was obtained as a white solid from the compound (611 mg) obtained in Production Example 34 and the compound (413 mg) obtained in Production Example 29 by the same method as in Example 1 (see Table 15).

Example 12
(4S)-4-[(2S,3S)-4-cyclohexyl-2-hydroxy-3-[[Nα-methyl-N α-(N-piperidinocarbonyl-L-phenylalanyl)-L-histidyl]amino]butyl]-5,5-dimethyl-2-phenyl-1,3-dioxolane The title compound (320 mg) was obtained as a white solid from the compound (574 mg) obtained in Production Example 34 and the compound (452 mg) obtained in Production Example 30 by the same method as in Example 1 (see Table 15).

Example 13
(4S)-4-[(2S,3S)-4-cyclohexyl-2-hydroxy-3-[[Nα-methyl-N α-(N-piperidinocarbonyl-L-phenylalanyl)-L-histidyl]amino]butyl]-5,5-dimethyl-1,3-dioxolane hydrochloride The compound (300 mg) obtained in Example 1 was dissolved in a mixed solution of ethanol (0.27 ml) and ethyl acetate (5.13 ml) and a solution (2.09 ml) of 0.2N HCl-ethyl acetate was dropwise added. After stirring overnight at room temperature, crystals were collected by filtration and dried under reduced pressure to give 160 mg of the title compound as white crystals (see Table 16).

Example 14
(4S)-4-[(2S,3S)-4-cyclohexyl-2-hydroxy-3-[[Nα-methyl-N α-(N-piperidinocarbonyl-L-phenylalanyl)-L-histidyl]amino]butyl]-5,5-dimethyl-1,3-dioxolane citrate The compound (300 mg) obtained in Example 1 was dissolved in ethyl acetate (3 ml) and a solution of citric acid monohydrate (92.7 mg) in ethyl acetate (5 ml) was dropwise added. After stirring at room temperature for 15 minutes, crystals were collected by filtration and dried under reduced pressure to give 257 mg of the title compound as white crystals (see Table 16).

Example 15
(4S)-4-[(2S,3S)-4-cyclohexyl-2-hydroxy-3-[[Nα-methyl-N α-(N-piperidinocarbonyl-L-phenylalanyl)-L-histidyl]amino]butyl]-5,5-dimethyl-1,3-dioxolane L-tartrate The compound (300 mg) obtained in Example 1 was dissolved in ethyl acetate (4.5 ml) and a solution of L-tartaric acid (66 mg) in ethyl acetate (5 ml) and ethanol (0.5 ml) was dropwise added. After stirring overnight at room temperature, crystals were collected by filtration and dried under reduced pressure to give 251 mg of the title compound as white crystals (see Table 16).

Example 16
(4S)-4-[(2S,3S)-4-cyclohexyl-2-hydroxy-3-[[Nα-methyl-N α-(N-piperidinocarbonyl-L-phenylalanyl)-L-histidyl]amino]butyl]-5,5-dimethyl-1,3-dioxolane methanesulfonate The compound (310 mg) obtained in Example 1 was dissolved in ethyl acetate (7 ml) and a solution of methanesulfonic acid (44 mg) in ethyl acetate (5 ml) and ethanol (0.25 ml) was dropwise added. After stirring at room temperature for 3 hours, crystals were collected by filtration and dried under reduced pressure to give 292 mg of the title compound as white crystals (see Table 16).

Example 17
(4S)-4-[(2S,3S)-4-cyclohexyl-2-hydroxy-3-[[Nα-methyl-N α-(N-piperidinocarbonyl-L-phenylalanyl)-L-histidyl]amino]butyl]-5,5-dimethyl-1,3-dioxolane maleate The compound (778 mg) obtained in Example 1 was dissolved in ethyl acetate (10 ml) and a solution of maleic acid (132 mg) in ethyl acetate (15.5 ml) and ethanol (1.55 ml) was dropwise added. After stirring overnight at room temperature, crystals were collected by filtration and dried under reduced pressure to give 723 mg of the title compound as white crystals (see Table 17).

The structural formulas and physical properties of the compounds with respect to the above-mentioned Production Examples and Examples specifically described in the present Specification are shown in Tables 1–17.

TABLE 1

| Compound | Structural formula | Rf value (solvent) | MS | $^1$H—NMR (solvent) |
|---|---|---|---|---|
| Production Example 1 | | 0.43 (AcOEt/Hex = 2/8 v/v developed twice) | | 3.60(m,1H),3.75(m,1H), 5.12(m,4H),5.81(m,1H) (CDCl$_3$) |
| Production Example 2 | | 0.74 (AcOEt/Hex = 2/8 v/v) | | 2.35(m,2H),3.7–4.0(m,2H), 5.13(m,4H),5.78(m,2H) (CDCl$_3$) |
| Production Example 3 | | 0.07 (AcOEt/Hex = 1/9 v/v) | | 2.72(m,2H),3.80(m,1H), 4.42(m,1H),5.13(m,4H) 9.79(s,1H) (CDCl$_3$) |

TABLE 1-continued

| Compound | Structural formula | Rf value (solvent) | MS | ¹H—NMR (solvent) |
|---|---|---|---|---|
| Production Example 4 | 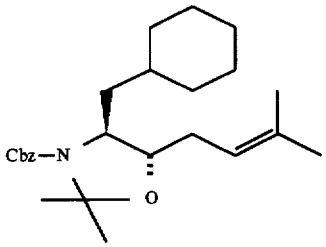 | 0.51 (AcOEt/Hex = 1/9 v/v) | | 2.28(t,2H),3.7–4.0(m,2H), 5.14(m,3H) (CDCl₃) |

TABLE 2

| Compound | Structural formula | Rf value (solvent) | MS | $^1$H—NMR (solvent) |
|---|---|---|---|---|
| Production Example 5 | | 0.40 (AcOEt/Hex = 4/6 v/v) | | 2.46(m,2H),3.58(m,1H), 4.19(m,1H),5.20(m,2H) (CDCl₃) |
| Production Example 6 | | 0.69 (AcOEt/Hex = 3/7 v/v) | | 2.32(m,2H),3.64(m,1H), 3.90(m,1H) (CDCl₃) |
| Production Example 7 | | | | 0.14(s,9H),0.21(s,9H), 1.32(s,6H),4.00(s,1H) 4.43(s,1H) (CDCl₃) |
| Production Example 8 | | 0.61 (AcOEt/Hex = 2/8 v/v developed twice) | | 0.15(s,9H),2.84(m,2H), 3.17(m,1H),3.71(m,1H), 3.98(m,1H),5.11(m,2H) (CDCl₃) |

TABLE 3

| Compound | Structural formula | Rf value (solvent) | MS | $^1$H—NMR (solvent) |
|---|---|---|---|---|
| Production Example 9 | 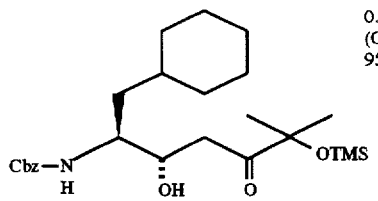 | 0.42 (CHCl₃/MeOH = 95/5 v/v) | | 2.74(m,2H),3.72(m,1H), 4.07(m,1H),5.11(s,2H) (CDCl₃) |

TABLE 3-continued

| Compound | Structural formula | Rf value (solvent) | MS | ¹H—NMR (solvent) |
|---|---|---|---|---|
| Production Example 10 | (structure: Cbz-N(Boc)-CH(CH₂-cyclohexyl)-CH-CH₂-C(=O)-C(CH₃)₂-OH) | 0.33 (AcOEt/Hex = 3/7 v/v) | | 3.52(m,1H),3.82(m,1H), 4.41(m,1H),5.13(m,2H) (CDCl₃) |
| Production Example 11 | (structure: Cbz-N(Boc)-CH(CH₂-cyclohexyl)-CH-CH₂-CH(OH)-C(CH₃)₂-OH) | 0.09 (AcOEt/Hex = 2/8 v/v developed twice) | | 3.65–3.90(m,2H), 4.20(m,1H),5.14(m,2H) (CDCl₃) |
| Production Example 12 | (structure: Cbz-N(Boc)-CH(CH₂-cyclohexyl)-CH-CH₂-CH(OH)-C(CH₃)₂-OH) | 0.14 (AcOEt/Hex = 2/8 v/v developed twice) | | 3.61(m,1H),3.79(m,1H), 4.12(m,1H),5.13(m,2H) (CDCl₃) |

TABLE 4

| Compound | Structural formula | Rf value (solvent) | MS | ¹H—NMR (solvent) |
|---|---|---|---|---|
| Production Example 13 | (structure with acetonide) | 0.65 (AcOEt/Hex = 3/7 v/v) | | 3.73(m,1H),3.86(m,1H), 4.11(m,1H), 4.85–5.25(m,4H) (CDCl₃) |
| Production Example 14 | (structure with acetonide) | 0.80 (AcOEt/Hex = 3/7 v/v) | | 3.49(m,1H),3.85(m,1H) (CDCl₃) |

TABLE 4-continued

| Compound | Structural formula | Rf value (solvent) | MS | $^1$H—NMR (solvent) |
|---|---|---|---|---|
| Production Example 15 | Cbz—NH—CH(CH$_2$-cyclohexyl)—CH(OH)—CH$_2$—CH(O-)—C(CH$_3$)$_3$ | 0.47 (CHCl$_3$/MeOH/NH$_4$OH = 95/5/0.5 v/v/v) | | 3.71(m,2H),3.84(m,1H), 4.80–5.20(m,4H) (CDCl$_3$) |
| Production Example 16 | Cbz—NH—CH(CH$_2$-cyclohexyl)—CH(OH)—CH$_2$—CH(O-)—C(CH$_3$)$_3$ | 0.44 (AcOEt/Hex = 3/7 v/v) | | |

TABLE 5

| Compound | Structural formula | Rf value (solvent) | MS | $^1$H—NMR (solvent) |
|---|---|---|---|---|
| Production Example 17 | (CH$_3$)$_3$C—C(=O)—... OMOM | | | 1.35(s,6H),2.22(s,3H), 3.39(s,3H),4.70(s,2H) (CDCl$_3$) |
| Production Example 18 | CH$_2$=C(OTMS)—C(CH$_3$)$_2$—OMOM | | | 0.22(s,9H),1.35(s,6H), 3.37(s,3H),4.15(s,1H), 4.38(s,1H),4.69(s,2H) (CDCl$_3$) |
| Production Example 19 | Cbz—NH—CH(CH$_2$-cyclohexyl)—CH(OH)—CH$_2$—C(=O)—C(CH$_3$)$_2$—OMOM | 0.43 (AcOEt/Hex = 3/7 v/v developed twice) | | 2.80(m,2H),3.33(s,3H), 3.71(m,1H),4.02(m,1H) 4.67(s,2H),5.11(s,2H) (CDCl$_3$) |
| Production Example 20 | Cbz—NH—CH(CH$_2$-cyclohexyl)—CH(OH)—CH$_2$—CH(OH)—C(CH$_3$)$_2$—OMOM | 0.18 (AcOEt/Hex = 5/5 v/v) | | 3.37(s,3H),3.68(m,2H), 3.89(m,1H),4.71(m,2H), 5.11(s,2H) (CDCl$_3$) |

TABLE 6

| Compound | Structural formula | Rf value (solvent) | MS | ¹H—NMR (solvent) |
|---|---|---|---|---|
| Production Example 21 | (structure) | 0.14 (AcOEt/Hex = 5/5 v/v) | | 3.10(m,1H),3.39(s,3H), 3.57(m,1H),3.70(m,1H), 4.47(m,1H),4.73(m,2H), 5.19(s,1H) (CDCl₃) |
| Production Example 22 | (structure) | 0.37 (AcOEt/Hex = 5/5 v/v) | | 3.61(m,1H),3.75(m,1H), 4.36(m,1H),4.91(s,1H), 5.04(s,1H),5.42(s,1H) (CDCl₃) |
| Production Example 23 | (structure) | 0.53 (AcOEt/Hex = 5/5 v/v | | 3.34(s,3H),3.63(m,1H), 3.79(m,1H),4.38(m,1H) 4.92(s,1H),5.06(s,1H) (CDCl₃) |
| Production Example 24 | (structure) | 0.09 (CHCl₃/MeOH/NH₄OH = 95/5/0.5 v/v/v) | | 2.71(m,1H),3.48(m,1H), 4.92(s,1H),5.05(s,1H) (CDCl₃) |

TABLE 7

| Compound | Structural formula | Rf value (solvent) | MS | ¹H—NMR (solvent) |
|---|---|---|---|---|
| Production Example 25 | (structure) | | | |

TABLE 7-continued

| Compound | Structural formula | Rf value (solvent) | MS | $^1$H—NMR (solvent) |
|---|---|---|---|---|
| Production Example 26 | 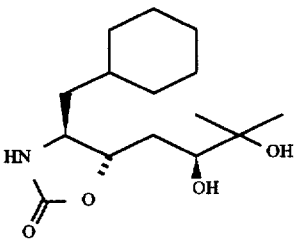 | 0.38 (CHCl$_3$/MeOH/NH$_4$OH = 90/10/1 v/v/v) | | 3.57(m,1H),3.70(m,1H), 4.46(m,1H),5.19(s,1H) (CDCl$_3$) |
| Production Example 27 | 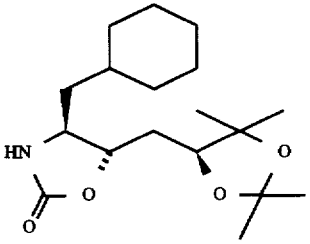 | 0.72 (CHCl$_3$/MeOH/NH$_4$OH = 90/10/1 v/v/v) | | 3.64(m,1H),3.92(m,1H), 4.34(m,1H),5.17(s,1H) (CDCl$_3$) |
| Production Example 28 | 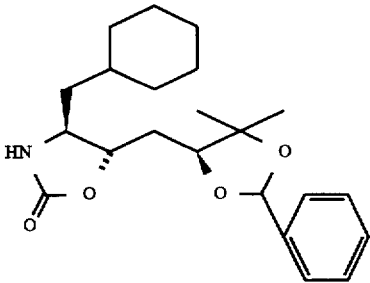 | | | 3.61(m,1H),4.01(m,1H), 4.39(m,1H), 5.85&5.99(s,1H, stereoisomer) (CDCl$_3$) |

TABLE 8

| Compound | Structural formula | Rf value (solvent) | MS | $^1$H—NMR (solvent) |
|---|---|---|---|---|
| Production Example 29 | 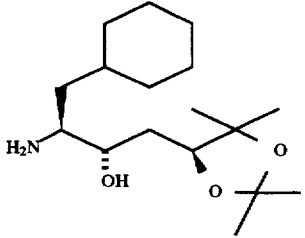 | | | 2.75(m,1H),3.46(m,1H), 4.00(m,1H) (CDCl$_3$) |
| Production Example 30 | 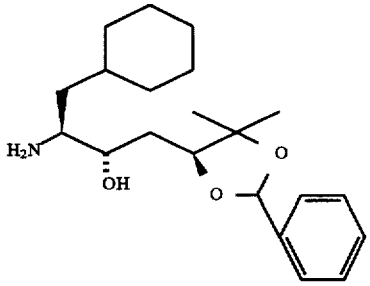 | | | 2.75(m,1H),3.52(m,1H), 4.04&4.13(m,1H, stereoisomer) 5.89&6.02(s,1H, stereoisomer) (CDCl$_3$) |

TABLE 8-continued

| Compound | Structural formula | Rf value (solvent) | MS | ¹H—NMR (solvent) |
|---|---|---|---|---|
| Production Example 31 | [piperidine-N-C(O)-NH-CH(CH₂Ph)-COOBn] | 0.46 (AcOEt/Hex = 5/5 v/v) | | 1.4–1.8(m,6H), 3.0–3.5(m,6H), 4.84(m,2H) (CDCl₃) |
| Production Example 32 | [piperidine-N-C(O)-NH-CH(CH₂Ph)-COOH] | | | 1.3–1.7(m,6H), 3.0–3.4(m,6H), 4.54(m,1H),4.82(d,1H, J = 6Hz) (CDCl₃) |

TABLE 9

| Compound | Structural formula | Rf value (solvent) | MS | ¹H—NMR (solvent) |
|---|---|---|---|---|
| Production Example 33 | [piperidine-N-C(O)-NH-CH(CH₂Ph)-C(O)-N(CH₃)-CH(CH₂-imidazole)-CO₂CH₃] | 0.44 (CHCl₃/MeOH/NH₄OH = 90/10/1 v/v/v) | | 2.77(s,3H),3.70(s,3H), 4.86(m,1H),5.07(m,1H), 5.29(m,1H),6.86(s,1H), 7.44(s,1H) (CDCl₃) |
| Production Example 34 | [piperidine-N-C(O)-NH-CH(CH₂Ph)-C(O)-N(CH₃)-CH(CH₂-imidazole)-CONHNH₂] | 0.44 (CHCl₃/MeOH/NH₄OH = 85/15/1 v/v/v) | | |
| Production Example 35 | [piperidine-N-C(O)-O-CH(CH₂Ph)-COOBn] | 0.44 (AcOEt/Hex = 3/7 v/v) | | 3.13(m,2H),3.37(m,4H), 5.0–5.3(m,3H) (CDCl₃) |

TABLE 9-continued
| Compound | Structural formula | Rf value (solvent) | MS | ¹H—NMR (solvent) |
|---|---|---|---|---|
| Production Example 36 | 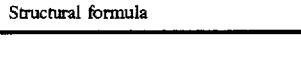 | | | |
TABLE 10
| Compound | Structural formula | Rf value (solvent) | MS | ¹H—NMR (solvent) |
|---|---|---|---|---|
| Production Example 37 | | 0.36 (CHCl₃/MeOH = 9/1 v/v) | | 3.95(m,1H),4.39(m,1H), 4.90(s,1H),5.02(s,1H), 5.11(m,1H),7.53(s,1H) (CDCl₃) |
| Production Example 38 | | | | 3.65(m,1H),3.79(m,2H), 4.00(m,1H),6.95(s,1H), 7.94(s,1H) (CD₃OD) |
| Production Example 39 | | 0.56 (CHCl₃/MeOH = 9/1 v/v) | | 3.31(m,1H),3.75(m,2H), 3.98(m,1H),4.8-5.2(m,5H) (CDCl₃) |

TABLE 10-continued

| Compound | Structural formula | Rf value (solvent) | MS | $^1$H—NMR (solvent) |
|---|---|---|---|---|
| Production Example 40 |  | 0.19 (CHCl$_3$/MeOH/NH$_4$OH = 90/10/1 v/v/v) | | 3.98(m,1H),4.89(s,1H), 5.01(s,1H),6.95(s,1H), 7.67(s,1H) (CDCl$_3$) |

TABLE 11

| Compound | Structural formula | Rf value (solvent) | MS | $^1$H—NMR (solvent) |
|---|---|---|---|---|
| Production Example 41 | | 0.53 (AcOEt/Hex = 5/5 v/v) | | 3.11(m,2H),4.84(m,2H), 5.14(m,2H) (CDCl$_3$) |
| Production Example 42 | | | | 3.20(m,2H),4.54(m,1H), 4.88(d,1H,J = 6Hz) (CDCl$_3$) |
| Production Example 43 | | 0.44 (AcOEt/Hex = 5/5 v/v) | | 1.06(t,6H,J = 7Hz), 3.12(m,2H), 4.72(d,1H,J = 7Hz), 4.86(m,1H) (CDCl$_3$) |
| Production Example 44 | | | | |

TABLE 12
| Compound | Structural formula | Rf value (solvent) | MS | ¹H—NMR (solvent) |
|---|---|---|---|---|
| Production Example 45 | 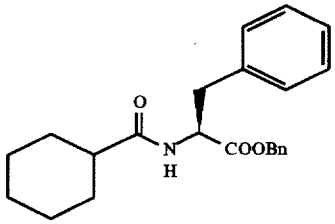 | 0.82 (AcOEt/Hex = 5/5 v/v) | | 3.12(m,2H),4.92(m,1H), 5.14(m,2H),5.85(d,1H, J = 7Hz) (CDCl$_3$) |
| Production Example 46 | 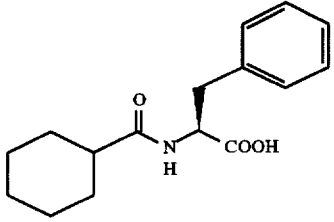 | | | 2.08(m,1H),3.18(m,2H), 6.05(d,1H,J = 7Hz) (CDCl$_3$) |
| Production Example 47 | 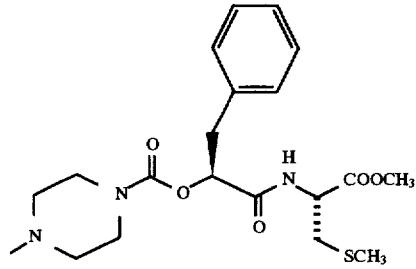 | 0.69 (CHCl$_3$/MeOH/NH$_4$OH = 85/15/1 v/v/v) | | 1.92(s,3H),2.29(s,3H), 3.48(m,4H),4.76(m,1H), 5.41(m,1H),6.84(d,1H, J = 7Hz) (CDCl$_3$) |
| Production Example 48 | 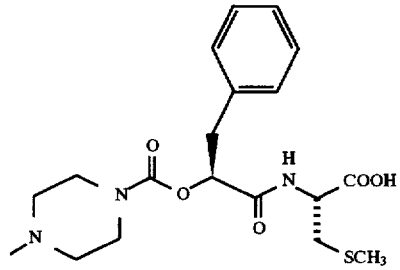 | | | |

TABLE 13

| Compound | Structural formula | Rf value (solvent) | MS | $^1$H—NMR (solvent) |
|---|---|---|---|---|
| Example 1 | | 0.74 (CHCl$_3$/MeOH/NH$_4$OH = 85/15/1 v/v/v) | FAB (M + H)$^+$ = 681 | 3.75(m,2H),4.05(m,1H), 4.70–5.10(m,4H), 6.69&6.75(m,1H, rotational isomer) (CDCl$_3$) |
| Example 2 | | 0.68 (CHCl$_3$/MeOH/NH$_4$OH = 85/15/1 v/v/v) | FAB (M + H)$^+$ = 681 | 3.70(m,2H),4.10(m,1H), 4.75–5.10(m,4H), 6.68(m,1H) (CDCl$_3$) |

TABLE 13-continued
| Compound | Structural formula | Rf value (solvent) | MS | $^1$H—NMR (solvent) |
|---|---|---|---|---|
| Example 3 | 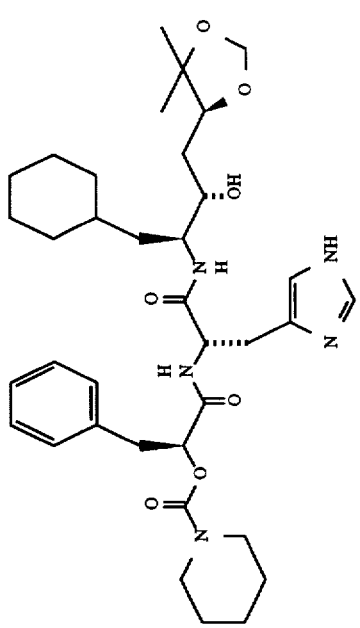 | 0.60 (CHCl$_3$/MeOH = 9/1 v/v) | | 3.80(m,1H),3.90(m,1H), 4.59(m,1H),5.02(s,1H), 6.80(s,1H),7.47(s,1H) (CDCl$_3$) |
| Example 4 | 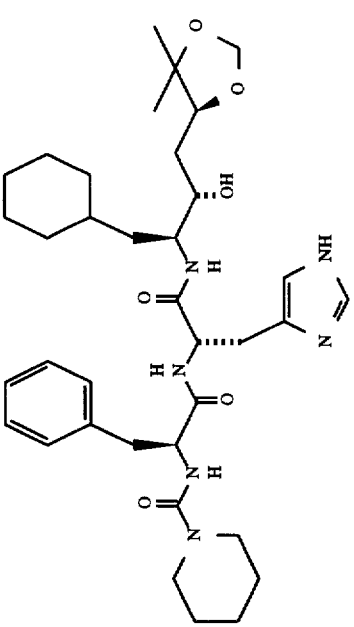 | 0.43 (CHCl$_3$/MeOH = 9/1 v/v) | | 3.70(m,1H),3.81(m,1H), 3.92(m,1H),4.14(m,1H), 4.64(m,1H),4.89(s,1H), 7.48(s,1H) (CDCl$_3$) |

TABLE 14

| Compound | Structural formula | Rf value (solvent) | MS | ¹H—NMR (solvent) |
|---|---|---|---|---|
| Example 5 | | 0.46 (CHCl₃/MeOH = 9/1 v/v) | FAB (M + H)⁺ = 663 | 2.03(s,3H),3.79(m,2H), 3.95(m,1H),4.50(m,1H) (CDCl₃) |
| Example 6 | | 0.32 (CHCl₃/MeOH/NH₄OH = 90/10/1 v/v/v) | FAB (M + H)⁺ = 717 | 3.76(m,1H),4.00(m,1H), 4.30(m,1H),4.88(s,1H), 5.02(s,1H) (CDCl₃) |

TABLE 14-continued

| Compound | Structural formula | Rf value (solvent) | MS | $^1$H—NMR (solvent) |
|---|---|---|---|---|
| Example 7 | | 0.27 (CHCl₃/MeOH/NH₄OH = 90/10/1 v/v/v) | FAB (M + H)⁺ = 552 | 3.20(m,2H),3.78(m,2H), 4.00(m,1H),4.81(m,1H), 4.88(s,1H),5.02(s,1H), 9.41(s,1H) (CDCl₃) |
| Example 8 | | 0.49 (CHCl₃/MeOH = 9/1 v/v) | FAB (M + H)⁺ = 680 | 3.78(m,2H),4.05(m,1H), 4.75–5.10(m,4H), 6.69&6.81(s,1H, rotational isomer) (CDCl₃) |

TABLE 15

| Compound | Structural formula | Rf value (solvent) | MS | ¹H-NMR (solvent) |
|---|---|---|---|---|
| Example 9 | | 0.38 (CHCl₃/MeOH = 9/1 v/v) | FAB (M+H)⁺= 695 | 4.05(m,1H), 4.70–5.10(m,4H), 6.69(s,1H) (CDCl₃) |
| Example 10 | | 0.41 (CHCl₃/MeOH = 9/1 v/v) | FAB (M+H)⁺= 669 | 3.75(m,2H),4.08(m,1H), 4.60–5.10(m,4H), 6.71(br s,1H) (CDCl₃) |

TABLE 15-continued
| Compound | Structural formula | Rf value (solvent) | MS | $^1$H—NMR (solvent) |
|---|---|---|---|---|
| Example 11 | 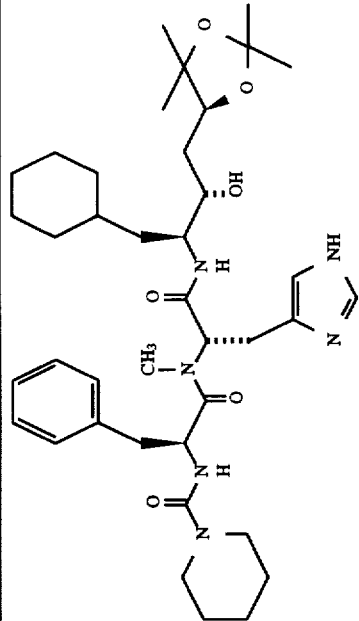 | 0.40 (CHCl$_3$/MeOH/NH$_4$OH = 90/10/1 v/v/v) | FAB (M + H)$^+$ = 709 | 3.71(m,1H), 3.90–4.20(m,2H), 4.65–5.00(m,2H), 6.70(s,1H) (CDCl$_3$) |
| Example 12 | 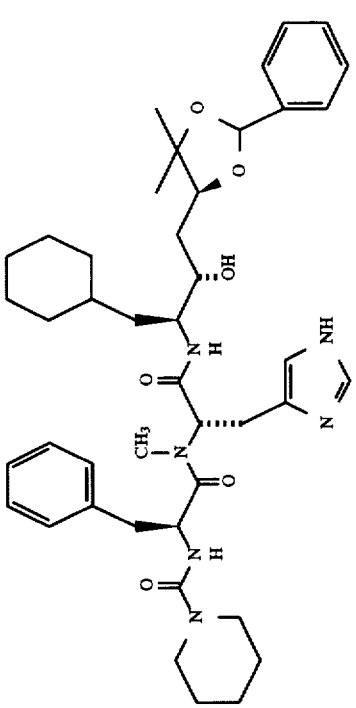 | 0.44 (CHCl$_3$/MeOH/NH$_4$OH = 90/10/1 v/v/v) | FAB (M + H)$^+$ = 757 | 4.06(m,2H),5.43(m,1H), 5.80&5.96(s,1H, stereoisomer) 6.68(s,1H) (CDCl$_3$) |

TABLE 16
| Compound | Structural formula | Rf value (solvent) | MS | ¹H-NMR (solvent) |
|---|---|---|---|---|
| Example 13 | 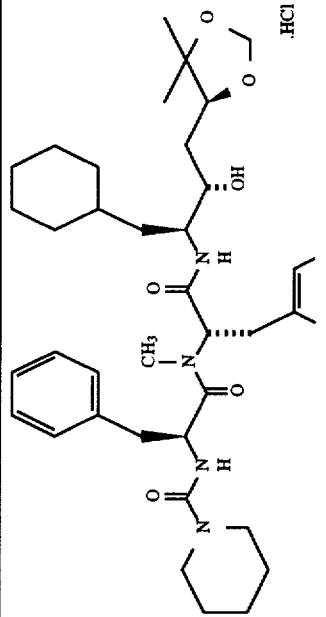 | | | 3.91&4.01(m,1H, rotational isomer) 5.09&5.22(m,1H, rotational isomer) 8.73(m,1H) (CD₃OD) |
| Example 14 | 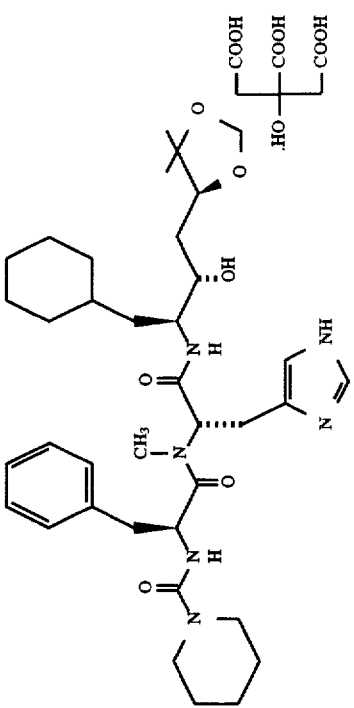 | | | 3.74(m,2H),3.95(m,1H), 5.16(m,1H), 8.19&8.46(s,1H, rotational isomer) (CD₃OD) |

TABLE 16-continued
| Compound | Structural formula | Rf value (solvent) | MS | ¹H-NMR (solvent) |
|---|---|---|---|---|
| Example 15 | 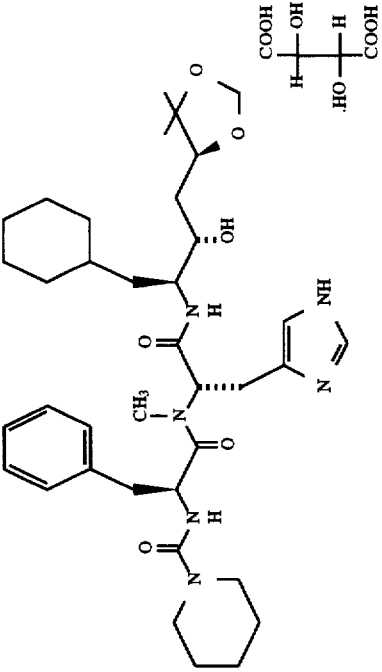 | | | 3.75(m,2H),3.96(m,1H), 4.51(s,2H), 8.11&8.40(s,1H, rotational isomer) (CD₃OD) |
| Example 16 | 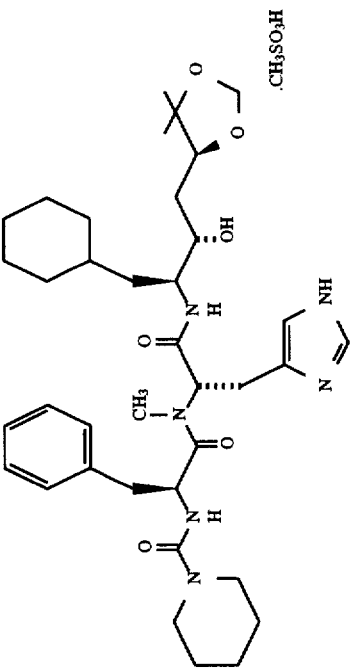 | | | 2.73(s,5H),3.09(s,1H), 3.90&4.01(m,1H, rotational isomer) 8.80(m,1H) (CD₃OD) |

TABLE 17

| Compound | Structural formula | Rf value (solvent) | MS | Compound ¹H-NMR (solvent) |
|---|---|---|---|---|
| Example 17 | (structure) 20 | | | 3.92&4.02(m,1H, rotational isomer) 5.10&5.21(m,1H, rotational isomer),6.29(s,1H), 8.61&8.70(s,1H, rotational isomer) (CD₃OD) |

It should be understood that the present invention is not limited to these Examples and, for example, the compounds shown in Tables 18–21 are also encompassed in the present invention.

TABLE 18

| Compound | Structural formula |
|---|---|
| 18 | (structure) |
| 19 | (structure) |

TABLE 18-continued
| Compound | Structural formula |
| --- | --- |
| 20 | 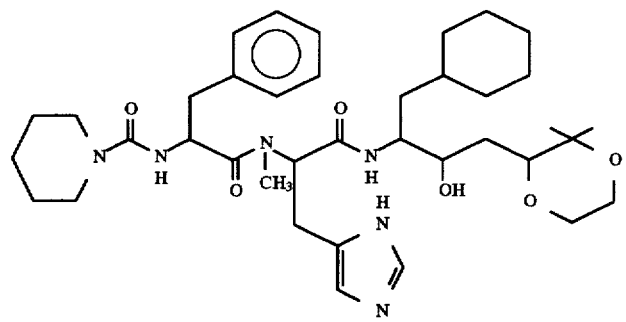 |
| 21 | 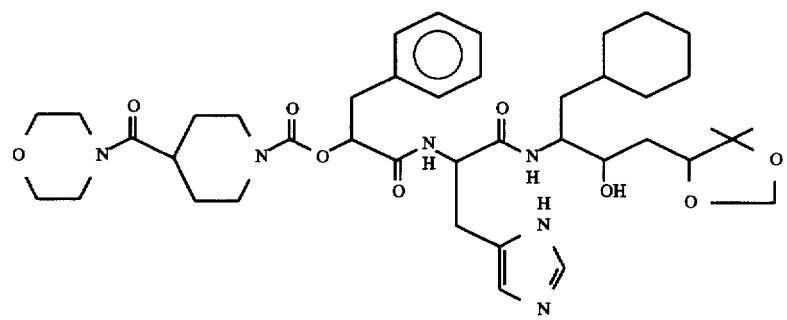 |
| 22 | 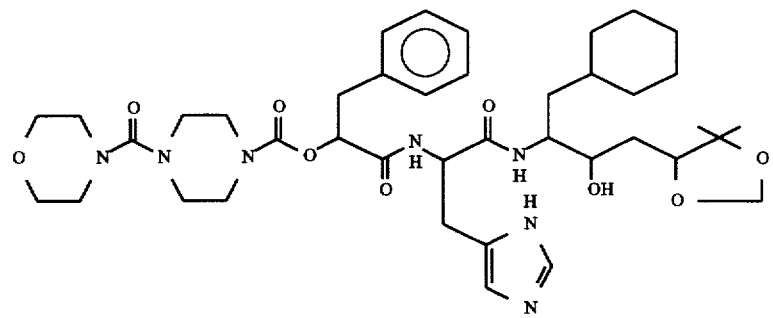 |
| 23 | 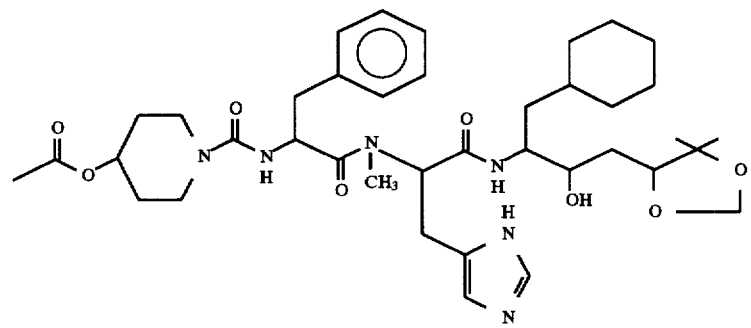 |

TABLE 18-continued
| Compound | Structural formula |
|---|---|
| 24 | 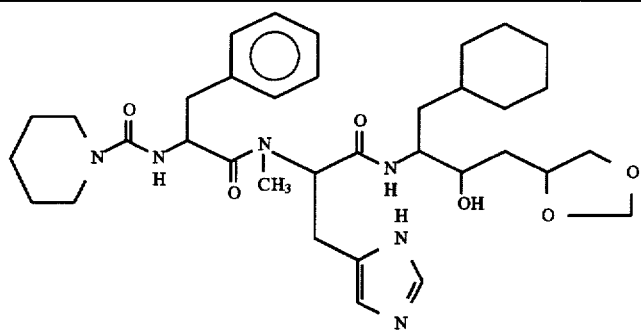 |
| 25 | 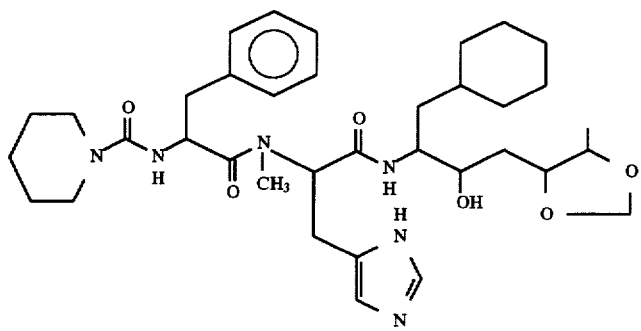 |
TABLE 19
| Compound | Structural formula |
|---|---|
| 26 | 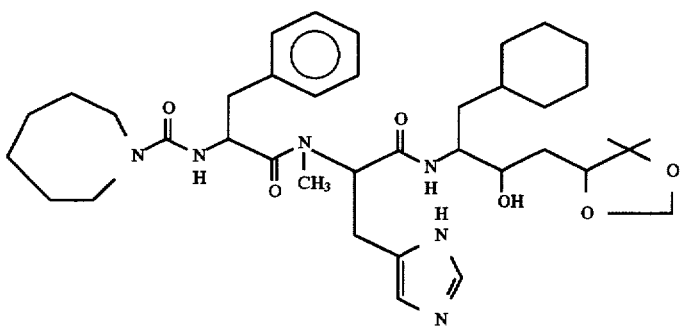 |
| 27 | 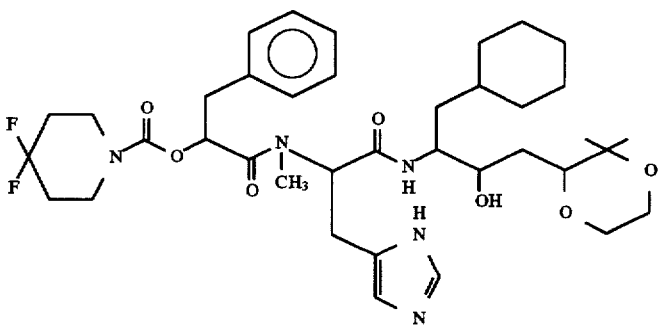 |

TABLE 19-continued
| Compound | Structural formula |
|---|---|
| 28 | 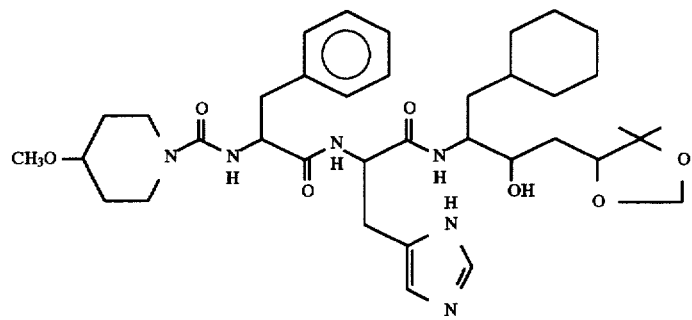 |
| 29 | 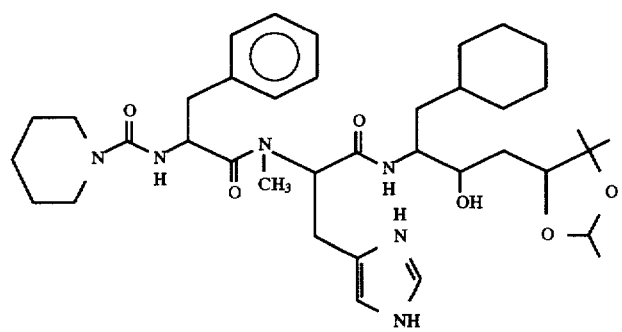 |
| 30 | 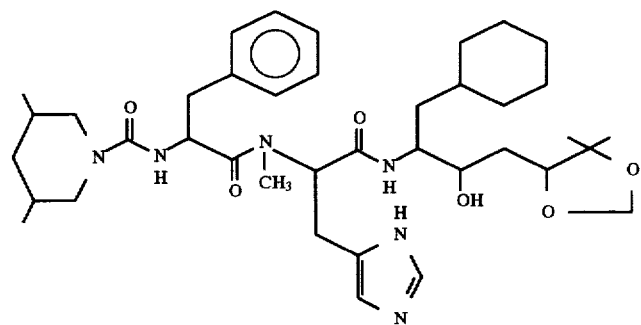 |
| 31 | 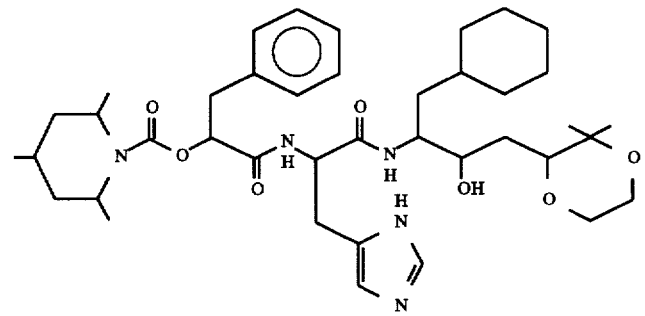 |

TABLE 19-continued
| Compound | Structural formula |
|---|---|
| 32 | 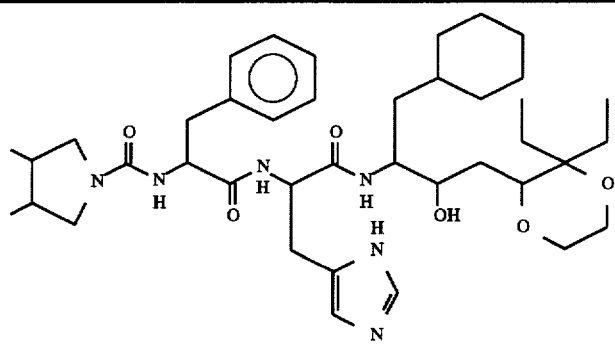 |
| 33 | 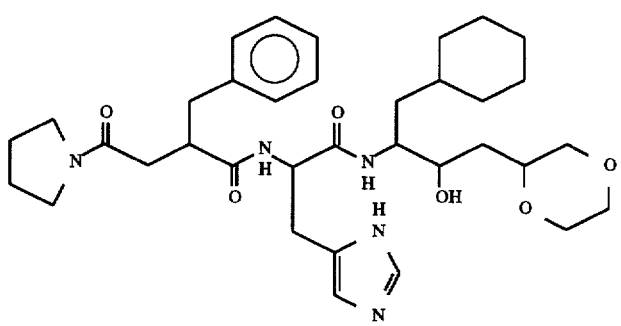 |
TABLE 20
| Compound | Structural formula |
|---|---|
| 34 | 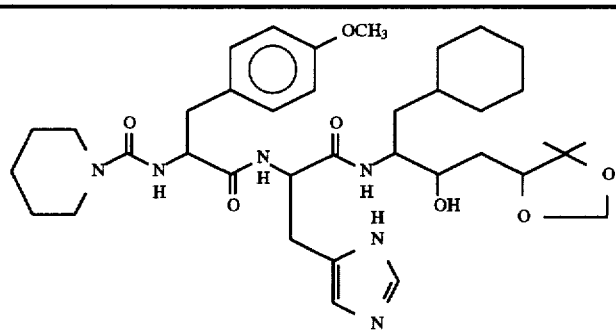 |
| 35 | 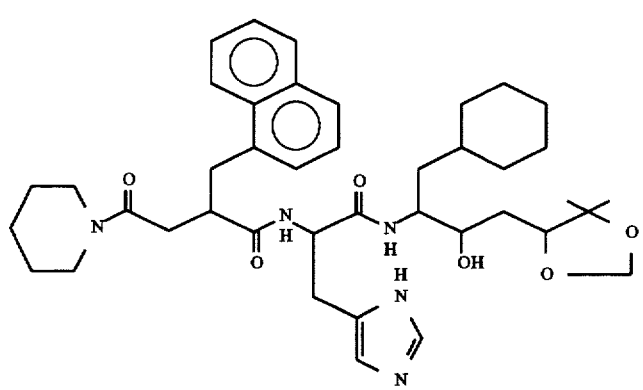 |

TABLE 20-continued
| Compound | Structural formula |
|---|---|
| 36 | 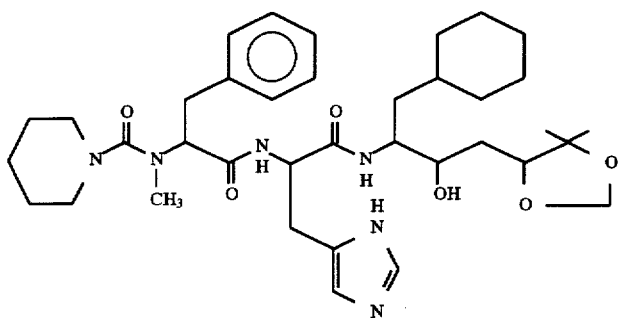 |
| 37 | 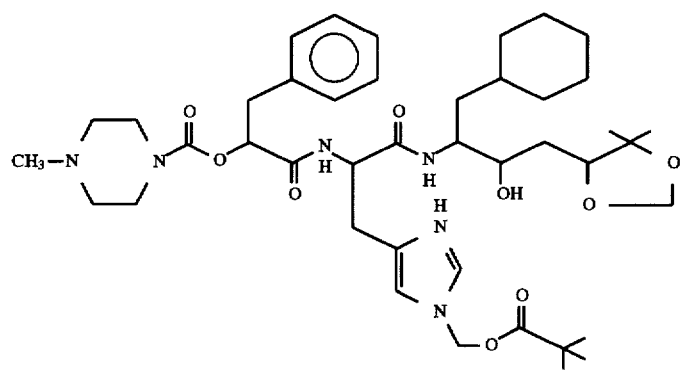 |
| 38 | 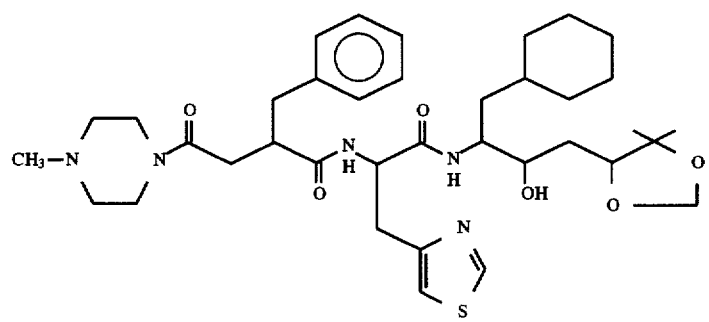 |
| 39 | 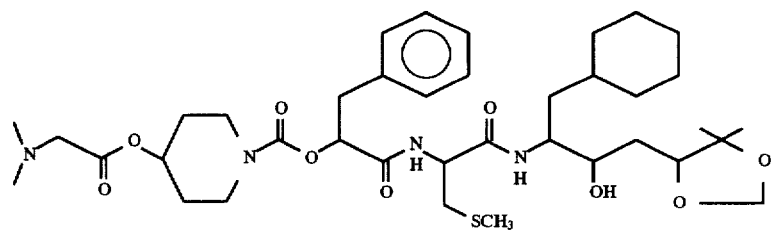 |
| 40 | 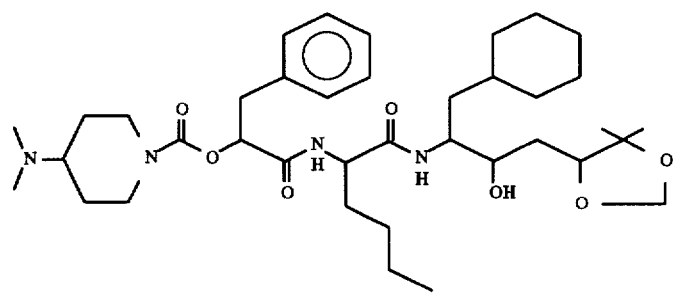 |

TABLE 20-continued

| Compound | Structural formula |
|---|---|
| 41 | |

TABLE 21

| Compound | Structural formula |
|---|---|
| 42 | |
| 43 | |
| 44 | |

TABLE 21-continued
| Compound | Structural formula |
|---|---|
| 45 | 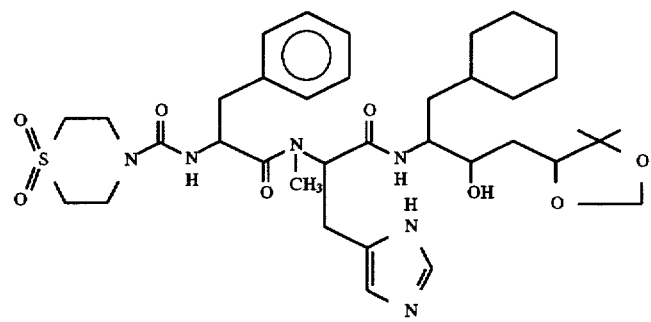 |
| 46 | 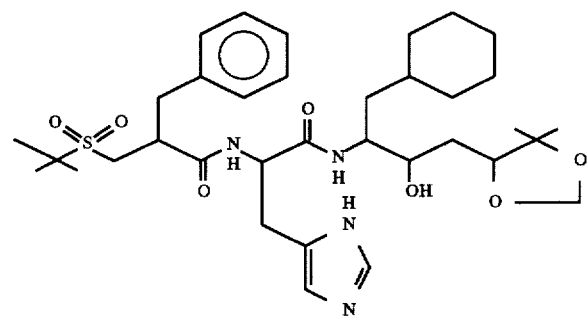 |
| 47 | 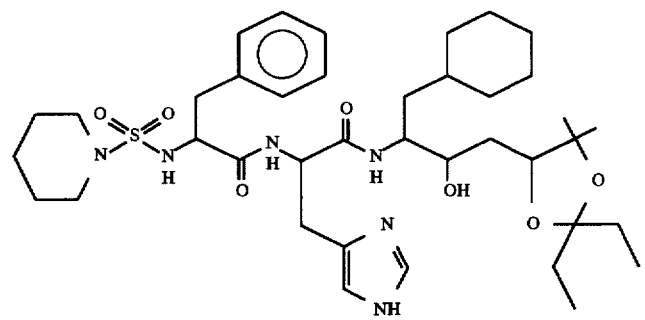 |
| 48 | 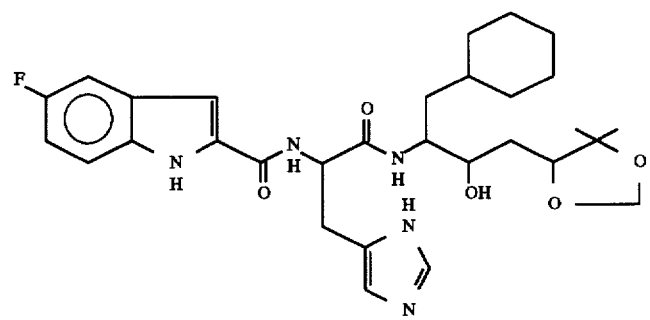 |

TABLE 21-continued

| Compound | Structural formula |
|---|---|
| 49 | 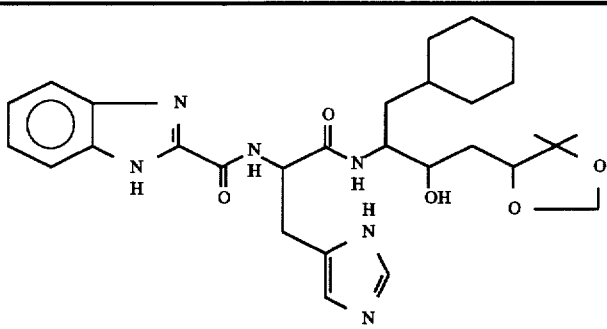 |

In the following, the test results of the inhibitory action of the dioxacycloalkane compound of the above-mentioned formula [1] of the present invention, on the renin activity in human plasma and the hypotensive action on nonanesthetized marmosets under salt intake control are shown.

Experimental Example 1
Inhibitory action on renin activity in human plasma

Human plasma (200 μl), a pH adjusting solution (20 μl), PMSF (10 μl), and a solution (10 μl) of the dioxacycloalkane compound of the present invention in dimethyl sulfoxide or dimethyl sulfoxide (10 μl) as a control were placed in plastic tubes for RIA. Two sets of these were prepared and one set of them was incubated at 37° C. for 1 hour and the other was incubated at 4° C. for 1 hour.

After incubation, the amount of angiotensin I was quantitatively assayed by the radio immunoassay method. The renin activity in plasma was calculated by subtracting the amount of angiotensin I in the reaction mixture incubated at 4° C. from that in the reaction mixture incubated at 37° C. Percent inhibitory activity was calculated from the following formula $$\text{Inhibitory activity} = \frac{\text{Control value} - \text{Value with compound of the invention}}{\text{Control value}} \times 100$$

The molar concentration necessary for 50% inhibition of activity ($IC_{50}$) was determined from the inhibitory activity value obtained by the above calculating formula. [RENIN RIABEADS KIT (Dinabot Ltd.) was used for the measurement.]

The results are shown in Table 22.

TABLE 22

Inhibitory action on renin activity in human plasma

| Compound | $IC_{50}$ ($1 \times 10^{-9}$ M) |
|---|---|
| Example 1 | 0.9 |
| Example 2 | 21 |
| Example 3 | 7 |
| Example 4 | 1.8 |
| Example 5 | 14 |
| Example 6 | 11 |
| Example 9 | 3.0 |
| Example 10 | 7.8 |
| Example 11 | 13 |
| Example 12 | 4 |

Experimental Example 2
Hypotensive action on non-anesthetized marmosets under salt intake control Non-anesthetized marmosets (weighing 310–370 g) raised on a low salt diet (containing 0.02% salt, 1/10 of the normal diet) for a week were orally administered with the compound (10 mg/kg) of Example 1 dissolved in 0.1 M citric acid, at the ratio of 2 ml/kg. The blood pressure was measured with the lapse of time before and after the administration by the tail-cuff method, and the hypotensive action was calculated in percentage relative to the value measured before the administration. The results are shown in Table 23.

TABLE 23

Hypotensive action on non-anesthetized marmosets under salt intake control

| Test compound | Dose (mg/kg, po) | Hypotensive action (%) | | | | |
|---|---|---|---|---|---|---|
| | | 0.5 hr later | 1 hr later | 3 hrs later | 5 hrs later | 7 hrs later |
| Example 1 | 10 | 10 | 12 | 10 | 10 | 3 |

As is evident from the results of Table 23, the pharmacological action of the compound of the present invention as evaluated in vivo was a remarkable hypotensive action with superior duration.

Effects of the Invention

The novel dioxacycloalkane compound of the above-mentioned formula [1] of the present invention shows a strong inhibitory activity against renin and continuous hypotensive action by oral administration. Accordingly, the object compound [1] of the present invention is expected to be usable as a hypotensive agent or a therapeutic agent for heart failure, which can be administered orally and is superior in duration of the action.

The compounds of the aforementioned formulas [II], [III], [IV], [V], [VI] and [VII] of the present invention are useful as intermediates for the production of the object compound [1] of the present invention.

We claim:

1. A dioxacycloalkane compound of the formula [1]

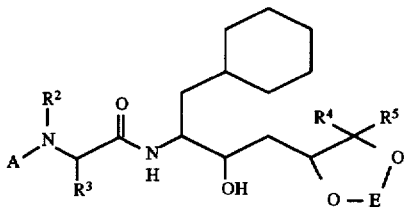

wherein A is

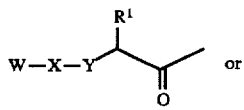 or

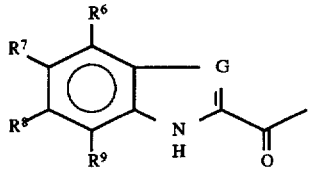

wherein W is

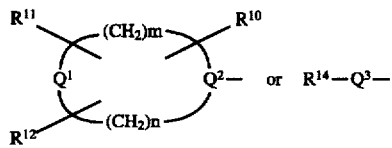 or $R^{14}-Q^3-$ wherein $R^{10}$, $R^{11}$ and $R^{12}$ are the same or different and each is a hydrogen atom, a lower-alkyl, a halogen atom, amino, a lower alkylamino, a lower dialkylamino or $-O-R^{15}$ wherein $R^{15}$ is a hydrogen atom, a lower alkyl, a lower alkanoyl or an acyl group of amino acid, m and n are each independently an integer of 0–5, the total of which is 1 to 5, $Q^1$ is $-CH_2-$, $-O-$, $-S-$, $-SO-$, $-SO_2-$,

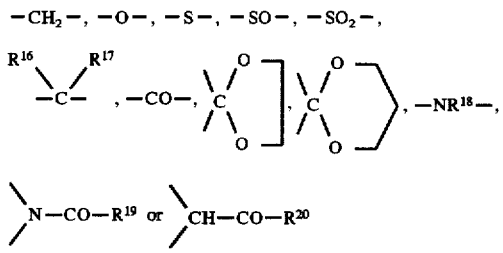

wherein $R^{16}$ and $R^{17}$ are the same or different and each is a lower alkyl or a halogen atom, $R^{18}$ is a hydrogen atom or a lower alkyl, $R^{19}$ and $R^{20}$ are each a lower alkyl or

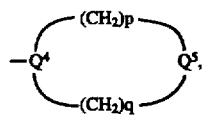

wherein $Q^4$ is 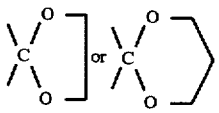 and $Q^5$ is $-CH_2-$, $-O-$, $-S-$, $-SO-$, $-SO_2-$, $-CO-$, $-CHF-$, $-CF_2-$, $-NR^{21}-$, $\diagdown CH-O-R^{22}$,

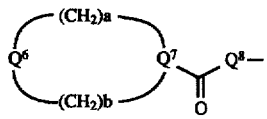

wherein $R^{21}$ and $R^{22}$ are each a hydrogen atom or a lower alkyl, p and q are each independently an integer of 1–4, the total of which does not exceed 5, $Q^2$ is $\diagdown CH-$ or $\diagdown N-$, $Q^3$ is $-\underset{\underset{}{}}{N}-$, $-O-$ or $-\underset{\underset{R^{23}}{|}}{\overset{\overset{R^{13}}{|}}{C}}-$ wherein $R^{13}$ is a hydrogen atom or a lower alkyl, $R^{23}$ is a hydrogen atom or a lower alkyl, and $R^{14}$ is a hydrogen atom, amino, a lower alkylamino, a lower dialkylamino, hydroxy, a lower alkoxy, methoxymethoxy, methoxyethoxymethoxy, a lower alkyl optionally substituted by a group of the formula wherein $Q^6$ is the same as the above-mentioned $Q^5$, $Q^7$ is the same as the above-mentioned $Q^4$, $Q^8$ is $-CH_2-$ or $-NR^{24}-$ wherein $R^{24}$ is a hydrogen atom or a lower alkyl, and a and b are each independently an integer of 1–4, the total of which does not exceed 5, or a benzyl optionally substituted by a lower alkoxy, X is $-CO-$ or $-SO_2-$, Y is $-CH_2-$, $-O-$ or $-NR^{25}-$ wherein $R^{25}$ is a hydrogen atom or a lower alkyl, $R^1$ is an aralkyl optionally substituted by a lower alkoxy, $R^6$, $R^7$, $R^8$ and $R^9$ are the same or different and each is a hydrogen atom, a halogen atom, hydroxy or a lower alkoxy, and G is $-N=$ or $-CH=$;

$R^2$ is a hydrogen atom or a lower alkyl;

$R^3$ is $-(CH_2)d-SR^{26}$ wherein d is an integer of 1–5 and $R^{26}$ is a hydrogen atom or a lower alkyl, a lower alkyl,

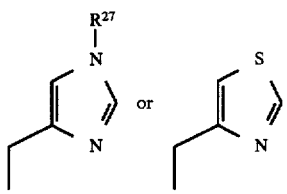 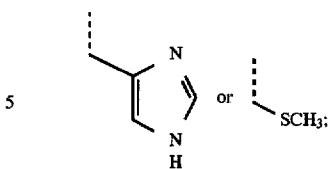

wherein $R^{27}$ is a hydrogen atom, a lower alkyl or —CH$_2$O—CO—$R^{28}$ wherein $R^{28}$ is a lower alkyl or a lower alkoxy;

$R^4$ and $R^5$ are the same or different and each is a hydrogen atom or a lower alkyl; and E is —C($R^{29}$)($R^{30}$) or —CH$_2$CH$_2$— wherein $R^{29}$ and $R^{30}$ are the same or different and each is a hydrogen atom, a lower alkyl or a phenyl, or $R^{29}$ and $R^{30}$ may combinedly form a ring having 5 to 7 carbon atoms, or a pharmaceutically acceptable salt thereof.

2. The dioxacycloalkane compound of claim 1, which is represented by the formula

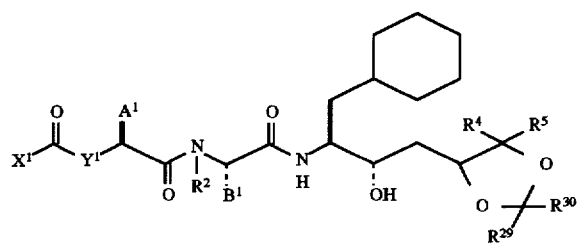

wherein $X^1$ is

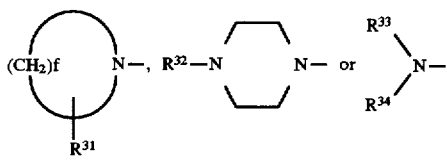

wherein $R^{31}$ is a hydrogen atom or a lower alkyl, $R^{32}$ is a hydrogen atom or a lower alkyl, $R^{33}$ and $R^{34}$ are the same or different and each is a hydrogen atom or a lower alkyl, and f is an integer of 4–6;

$Y^1$ is —CH$_2$—, —O— or —NH—;

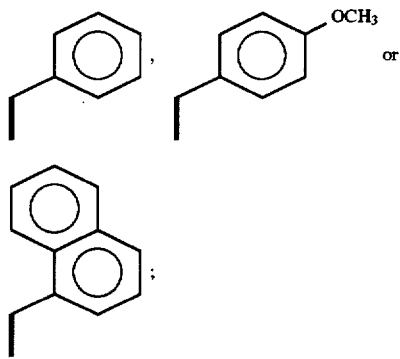

$R^2$, $R^4$, $R^5$, $R^{29}$ and $R^{30}$ are as defined in claim 1, or a pharmaceutically acceptable salt thereof.

3. The dioxacycloalkane compound of claim 1, which is a member selected from the group consisting of (1) (4S)-4-[(2S,3S)-4-cyclohexyl-2-hydroxy-3-[[Nα-methyl-N α-(N-piperidinocarbonyl-L-phenylalanyl)-L-histidyl]amino]-butyl]-5,5-dimethyl-1,3-dioxolane, (2) (4R)-4-[(2S,3S)-4-cyclohexyl-2-hydroxy-3-[[Nα-methyl-N α-(N-piperidinocarbonyl-L-phenylalanyl)-L-histidyl]amino]-butyl]-5,5-dimethyl-1,3-dioxolane, (3) (4S)-4-[(2S,3S)-4-cyclohexyl-2-hydroxy-3-[[Nα-[(2S)-3-phenyl-2-piperidinocarbonyloxypropionyl]-L-histidyl]amino]-butyl]-5,5-dimethyl-1,3-dioxolane, (4) (4S)-4-[(2S,3S)-4-cyclohexyl-2-hydroxy-3-[[Nα-(N-piperidino-carbonyl-L-phenylalanyl)-L-histidyl]amino] butyl]-5,5-dimethyl-1,3-dioxolane, (5) (4S)-4-[(2S,3S)-4-cyclohexyl-2-hydroxy-3-[[S-methyl-N-[(2S)-3-phenyl-2-(4-methylpiperazinyl) carbonyloxypropionyl ]-L-cysteinyl]amino]butyl]-5,5-dimethyl-1,3-dioxolane, (6) (4S)-4-[(2S,3S)-4-cyclohexyl-2-hydroxy-3-[[Nα-methyl-N α-(N-piperidinosulfonyl-L-phenylalanyl)-L-histidyl]amino]-butyl]-5,5-dimethyl-1,3-dioxolane, (7) (4S)-4-[(2S,3S)-4-cyclohexyl-2-hydroxy-3-[[N α-(indole-2-carbonyl)-L-histidyl]amino]butyl]-5,5-dimethyl-1,3-dioxolane, (8) (4S)-4-[(2S,3S)-4-cyclohexyl-2-hydroxy-3-[[Nα-methyl-N α-(N-cyclohexylcarbonyl-L-phenylalanyl)-L-histidyl]amino]-butyl]-5,5-dimethyl-1,3-dioxolane, (9) (4S)-4-[(2S,3S)-4-cyclohexyl-2-hydroxy-3-[[Nα-methyl-N α-[N-(4-methylpiperidino)carbonyl-L-phenylalanyl]-L-histidyl]-amino]butyl]-5,5-dimethyl-1,3-dioxolane,

(10) (4S)-4-[(2S,3S)-4-cyclohexyl-2-hydroxy-3-[[Nα-methyl-N α-[N-(diethylamino)carbonyl-L-phenylalanyl]-L-histidyl]amino]-butyl]-5,5-dimethyl-1,3-dioxolane,

(11) (4S)-4-[(2S,3S)-4-cyclohexyl-2-hydroxy-3-[[Nα-methyl-N α-(N-piperidinocarbonyl-L-phenylalanyl)-L-histidyl]amino]-butyl]-2,2,5,5-tetramethyl-1,3-dioxolane, and

(12) (4S)-4-[(2S,3S)-4-cyclohexyl-2-hydroxy-3-[[Nα-methyl-N α-(N-piperidinocarbonyl-L-phenylalanyl)-L-histidyl]amino]-butyl]-5,5-dimethyl-2-phenyl-1,3-dioxolane, or a pharmaceutically acceptable salt thereof.

4. A composition for inhibiting renin, comprising a pharmaceutically suitable carrier and the dioxacycloalkane compound of claim 1 or a pharmaceutically acceptable salt thereof in an amount effective for inhibiting renin.

5. A composition for inhibiting renin, comprising a pharmaceutically suitable carrier and the dioxacycloalkane compound of claim 2 or a pharmaceutically acceptable salt thereof in an amount effective for inhibiting renin.

6. A composition for inhibiting renin, comprising a pharmaceutically suitable carrier and the dioxacycloalkane compound of claim 3 or a pharmaceutically acceptable salt thereof in an amount effective for inhibiting renin.

7. A method for stereoselectively producing a compound of the formula

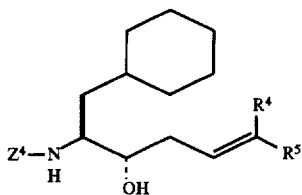

wherein $Z^4$ is an N-protecting group and $R^4$ and $R^5$ are the same or different and each is a hydrogen atom or a lower alkyl, comprising reacting an aldehyde of the formula

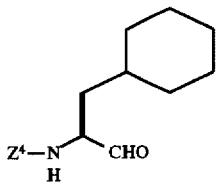

wherein $Z^4$ is as defined above, with an allylsilane compound of the formula

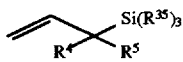

wherein $R^{35}$ is a lower alkyl and $R^4$ and $R^5$ are as defined above, in the presence of a Lewis acid.

8. A compound of the formula

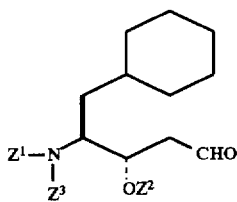

[III]

wherein $Z^1$ is a hydrogen atom or an N-protecting group, $Z^2$ is a hydrogen atom or a hydroxyl-protecting group, $Z^3$ is a hydrogen atom or may form, together with $Z^2$, an optionally substituted oxazolidine ring or an oxazolidinone ring.

9. A compound of the formula

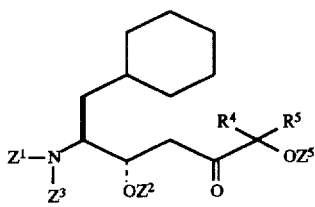

[IV]

wherein Z is a hydrogen atom or an N-protecting group, $Z^2$ is a hydrogen atom or a hydroxyl-protecting group, $Z^3$ is a hydrogen atom or may form, together with $Z^2$, an optionally substituted oxazolidine ring or an oxazolidinone ring, $R^4$ and $R^5$ are the same or different and each is a hydrogen atom or a lower alkyl, and $Z^5$ is a hydrogen atom or a hydroxyl-protecting group.

10. A method for stereoselectively producing the compound of claim 9 which is represented by the formula

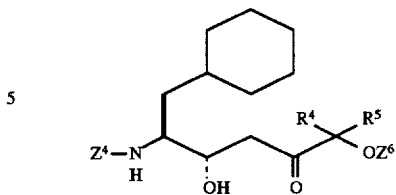

wherein $R^4$ and $R^5$ are the same or different and each is a hydrogen atom or a lower alkyl, $Z^4$ is an N-protecting group and $Z^6$ is a hydroxyl-protecting group, comprising reacting an aldehyde of the formula

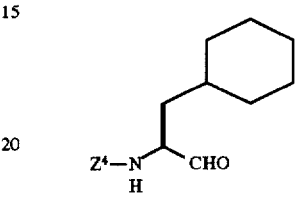

wherein Z4 is as defined above, with a silylenol ether compound of the formula

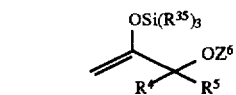

wherein $R^{35}$ is a lower alkyl, and $R^4$, $R^5$ and $Z^6$ are as defined above, in the presence of a Lewis acid.

11. A compound of the formula

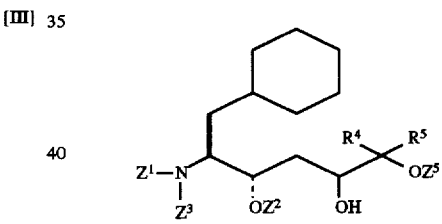

[V]

wherein Z is a hydrogen atom or an N-protecting group, $Z^2$ is a hydrogen atom or a hydroxyl-protecting group, $Z^3$ is a hydrogen atom or may form, together with $Z^2$, an optionally substituted oxazolidine ring or an oxazolidinone ring, $R^4$ and $R^5$ are the same or different and each is a hydrogen atom or a lower alkyl, and $Z^5$ is a hydrogen atom or a hydroxyl-protecting group.

12. A compound of the formula

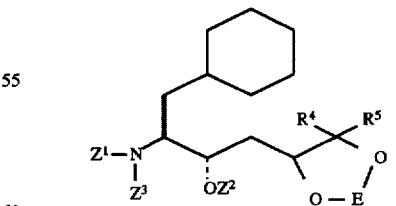

[VI]

wherein $Z^1$ is a hydrogen atom or an N-protecting group, $Z^2$ is a hydrogen atom or a hydroxyl-protecting group, $Z^3$ is a hydrogen atom or may form, together with $Z^2$, an optionally substituted oxazolidine ring or an oxazolidinone ring, $R^4$ and $R^5$ are the same or different and each is a hydrogen atom or a lower alkyl, E is —C($R^{29}$) ($R^{30}$)— or —CH$_2$CH$_2$— wherein $R^{29}$ and $R^{30}$ are the same or different and each is a hydrogen atom, a lower alkyl or a phenyl, or $R^{29}$ and $R^{30}$ may combinedly form a ring having 5 to 7 carbon atoms.

13. A method for stereoselectively producing a compound of the formula

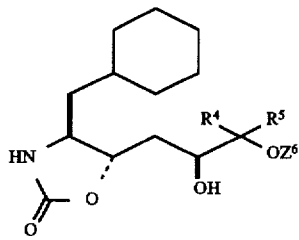

wherein $R^4$ and $R^5$ are the same or different and each is a hydrogen atom or a lower alkyl, and $Z^6$ is a hydroxyl-protecting group, comprising reducing a compound of the formula

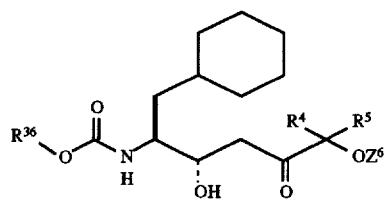

wherein $R^4$, $R^5$ and $Z^6$ are as defined above, and $R^{36}$ is a lower alkyl or a benzyl, using a boron hydride compound in the presence of a lower alkylcarboxylic acid to give a compound of the formula

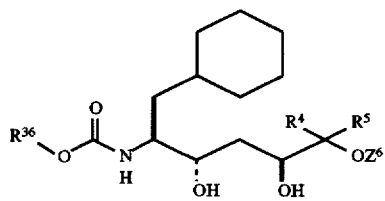

wherein $R^4$, $R^5$, $R^{36}$ and $Z^6$ are as defined above, followed by cyclocondensation in the presence of a base.

14. A method for producing a compound of the formula

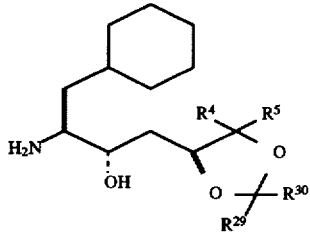

wherein $R^4$ and $R^5$ are the same or different and each is a hydrogen atom or a lower alkyl, and $R^{29}$ and $R^{30}$ are the same or different and each is a hydrogen atom, a lower alkyl or a phenyl, or $R^{29}$ and $R^{30}$ may combinedly form a ring having 5 to 7 carbon atoms, comprising acetalization of a compound of the formula

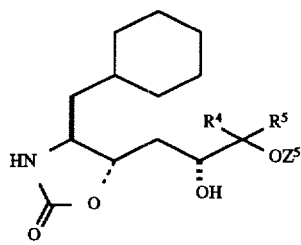

wherein $R^4$ and $R^5$ are as defined above, and $Z^5$ is a hydrogen atom or a hydroxyl-protecting group, using an acid including a Lewis acid as a catalyst to give a compound of the formula

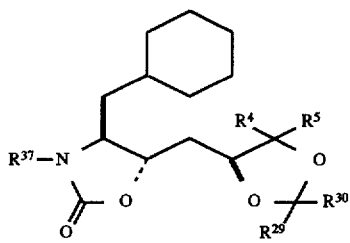

wherein $R^4$, $R^5$, $R^{29}$ and $R^{30}$ are as defined above, and $R^{37}$ is a hydrogen atom or methoxymethyl, followed by hydrolysis under the basic conditions.

15. A method for producing a compound of the formula

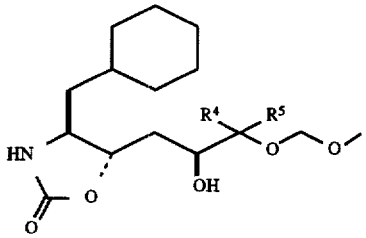

wherein $R^4$ and $R^5$ are the same or different and each is a hydrogen atom or a lower alkyl, comprising reacting an aldehyde of the formula

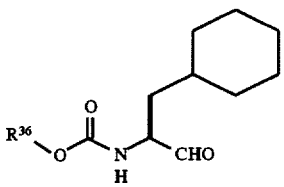

wherein $R^{36}$ is a lower alkyl or a benzyl, with a silylenol ether compound of the formula

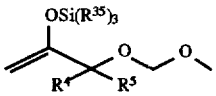

wherein $R^4$ and $R^5$ are as defined above, and $R^{35}$ is a lower alkyl, in the presence of a Lewis acid to stereoselectively produce a compound of the formula

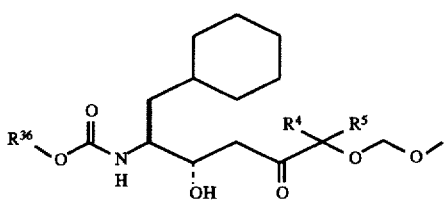

wherein $R^4$, $R^5$ and $R^{36}$ are as defined above, and reducing the obtained compound using a boron hydride compound in the presence of a lower alkylcarboxylic acid to stereoselectively produce a compound of the formula

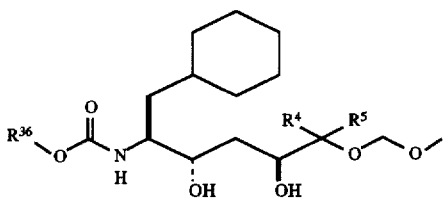

wherein $R^4$, $R^5$ and $R^{36}$ are as defined above, followed by cyclocondensation in the presence of a base.

16. A method for producing a compound of the formula

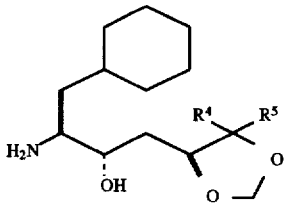

wherein $R^4$ and $R^5$ are the same or different and each is a hydrogen atom or a lower alkyl, comprising cyclocondensation of a compound of the formula

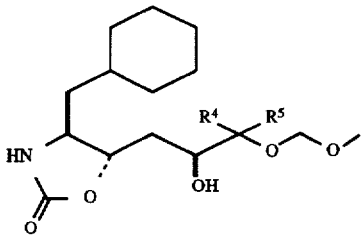

wherein $R^4$ and $R^5$ are as defined above, in the presence of an acid or diphosphorus pentaoxide, or reacting the compound with dimethoxymethane using an acid as a catalyst to give a compound of the formula

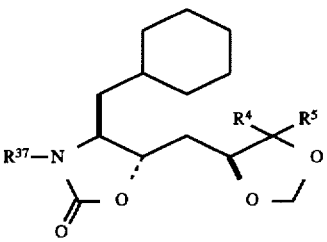

wherein $R^4$ and $R^5$ are as defined above, and $R^{37}$ is a hydrogen atom or methoxymethyl, followed by hydrolysis under the basic conditions.

17. A compound of the formula

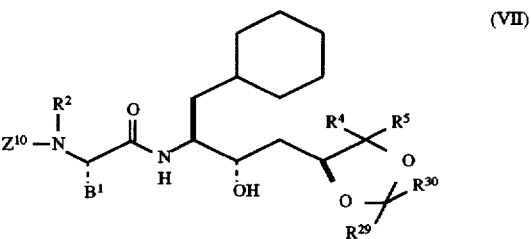

(VII)

wherein $Z^{10}$ is a hydrogen atom or an N-protecting group, $R^2$ is a hydrogen atom or a lower alkyl;

$R^4$ and $R^5$ are the same or different and each is a hydrogen atom or a lower alkyl;

$R^{29}$ and $R^{30}$ are the same or different and each is a hydrogen atom, a lower alkyl or a phenyl, or $R^{29}$ and $R^{30}$ may combinedly form a ring having 5 to 7 carbon atoms; and

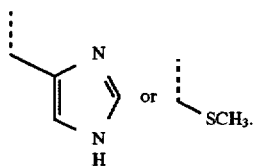

* * * * *